US008013003B2

(12) United States Patent
Street et al.

(10) Patent No.: US 8,013,003 B2
(45) Date of Patent: Sep. 6, 2011

(54) DI-SUBSTITUTED AMIDES FOR ENHANCING GLUTAMATERGIC SYNAPTIC RESPONSES

(75) Inventors: Leslie Street, Laguna Niguel, CA (US); Rudolf Mueller, Foothill Ranch, CA (US); Steven Lee, West Covina, CA (US)

(73) Assignee: Cortex Pharmaceuticals, Inc., Irvine, CA (US)

( * ) Notice: Subject to any disclaimer, the term of this patent is extended or adjusted under 35 U.S.C. 154(b) by 0 days.

(21) Appl. No.: 12/451,515

(22) PCT Filed: May 16, 2008

(86) PCT No.: PCT/US2008/006271
§ 371 (c)(1),
(2), (4) Date: Jan. 14, 2010

(87) PCT Pub. No.: WO2008/143963
PCT Pub. Date: Nov. 27, 2008

(65) Prior Publication Data
US 2010/0120764 A1    May 13, 2010

Related U.S. Application Data

(60) Provisional application No. 60/930,633, filed on May 17, 2007, provisional application No. 60/958,069, filed on Jul. 2, 2007.

(51) Int. Cl.
*C07D 413/00* (2006.01)
*A01N 43/82* (2006.01)
(52) U.S. Cl. ......................... 514/364; 548/126
(58) Field of Classification Search .................. None
See application file for complete search history.

(56) References Cited

U.S. PATENT DOCUMENTS

| | | | |
|---|---|---|---|
| 3,723,436 | A | 3/1973 | Hollstein et al. |
| 4,797,482 | A | 1/1989 | Constansa et al. |
| 5,650,409 | A | 7/1997 | Rogers et al. |
| 5,736,543 | A | 4/1998 | Rogers et al. |
| 5,747,492 | A | 5/1998 | Lynch et al. |
| 5,783,587 | A | 7/1998 | Rogers et al. |
| 5,962,447 | A | 10/1999 | Rogers et al. |
| 6,030,968 | A | 2/2000 | Gall et al. |
| 6,303,542 | B1 | 10/2001 | Li et al. |
| 2002/0055508 | A1* | 5/2002 | Rogers et al. |
| 2003/0153752 | A1* | 8/2003 | Hirst et al. |
| 2005/0026952 | A1* | 2/2005 | Mathias |
| 2005/0148603 | A1* | 7/2005 | Jimenez et al. |
| 2010/0041647 | A1 | 2/2010 | Mueller et al. |
| 2010/0137295 | A1 | 6/2010 | Cordi et al. |

FOREIGN PATENT DOCUMENTS

| | | |
|---|---|---|
| DE | 2012094 | 9/1971 |
| WO | WO9402475 | 2/1994 |
| WO | 9736907 | 10/1997 |
| WO | 9933469 | 7/1999 |
| WO | WO9942456 | 8/1999 |
| WO | 03099299 A1 | 12/2003 |
| WO | 2008085505 A1 | 7/2008 |
| WO | 2008085506 A1 | 7/2008 |
| WO | 2009023126 A2 | 2/2009 |
| WO | 2009038752 A2 | 3/2009 |

OTHER PUBLICATIONS

Chawla et al., "Challenges in Polymorphism of Pharmaceuticals", CRIPS vol. 5, No. 1, Jan.-Mar. 2004 (4 Pages.*
Newman et al., "Solid-state analysis of the active pharmaceutical ingredient in drug products", DDT vol. 8, No. 19, Oct. 2003, p. 898-905.*
Ishibashi et al., caplus an 1989:544092.*
http://www.chemdrug.com/database/10_3_gbflimrcjilwki.html, 2010.
Gouaux et al.,Structure and function of AMPA receptors. J. Physiol. 2003, 554, 249-253.
Gueyrard et al. A new and rapid access to homochiral 2,3-dihydro-oxazolo[2,3-b]quinazolin-5-ones, Tetrahedron: Assymmetry 2001, 12, 337-340. Murray et al. LY503430, a novel AMPA receptor potentiator with functional, neuroprotective and neurotrophic effects in rodent models of Parkinson's disease. J. Pharmacol. Exp. Ther. 2003, 306, 752-762.
Russell, Increased AMPA Receptor Function in Slices Containing the Prefrontal Cortex of Spontaneously Hypertensive Rats. Metabolic Brain Disease, 2001, 16, 143-149.
Pontarelli, New drug that enhances glutamate transmission in brain being evaluated for fragile X. printed Apr. 10, 2008 from Http://www.innovations-report.com/html/reports/medicine_health/report-12386.html.
Ren. Ampakines alleviate respiratory depression in rats. American Journal of Respiratory and Critical Care Medicine 2006, 174, 1384-1391.
Monaghan et al., in Brain Research 324:160 164 (1984).
Arai and Lynch, Brain Research 598:173 184 (1992).

(Continued)

*Primary Examiner* — Sun Jae Loewe
(74) *Attorney, Agent, or Firm* — Henry D. Coleman; R. Neil Sudol; William J. Sapone

(57) ABSTRACT

This invention relates to compounds, pharmaceutical compositions and methods for use in the prevention and treatment of cerebral insufficiency, including enhancement of receptor functioning in synapses in brain networks responsible for basic and higher order behaviors. These brain networks, which are involved in regulation of breathing, and cognitive abilities related to memory impairment, such as is observed in a variety of dementias, in imbalances in neuronal activity between different brain regions, as is suggested in disorders such as Parkinson's disease, schizophrenia, respiratory depression, sleep apneas, attention deficit hyperactivity disorder and affective or mood disorders, and in disorders wherein a deficiency in neurotrophic factors is implicated, as well as in disorders of respiration such as overdose of an alcohol, an opiate, an opioid, a barbiturate, an anesthetic, or a nerve toxin, or where the respiratory depression results form a medical condition such as central sleep apnea, stroke-induced central sleep apnea, obstructive sleep apnea, congenital hypoventilation syndrome, obesity hypoventilation syndrome, sudden infant death syndrome, Rett syndrome, spinal cord injury, traumatic brain injury, Cheney-Stokes respiration, Ondines curse, Prader-Willi's syndrome and drowning. In a particular aspect, the invention relates to compounds useful for treatment of such conditions, and methods of using these compounds for such treatment.

21 Claims, No Drawings

OTHER PUBLICATIONS

Granger et al., Synapse 15:326 329 (1993).
Staubli et al., PNAS 91:777-781 (1994).
Arai et al., Brain Res. 638:343 346 (1994).
Staubli et al., PNAS 91:11158-11162 (1994).
Shors et al., Neurosci. Let. 186:153 156 (1995).
Larson et al., J. Neurosci. 15:8023 8030 (1995).
Granger et al., Synapse 22:332 337 (1996).
Arai et al., JPET 278:627 638 (1996).
Lynch et al., Internat. Clin. Psychopharm. 11: 13 19 (1996).
Lynch et al., Exp. Neurology 145:89-92 (1997).
Ingvar et al., Exp. Neurology 146:553-559 (1997).
Hampson, et al., J. Neurosci. 18:2748-2763 (1998).
Porrino et al., PLoS Biol 3(9):1-14 (2006).
del Cerro and Lynch, Neuroscience 49: 1 6 (1992).
Whitlock et al., Science 313:1093-1097 (2006).
Pastalkova, et al., Science 313:1141-1144 (2006).
Rex, et al., J. Neurophysiol. 96:677-685 (2006).
Lauterborn, et al., J. Neurosci. 20:8-21 (2000).
Lauterborn, et al., JPET 307:297-305 (2003).
Mackowiak, et al., Neuropharmacology 43:1-10 (2002).
O'Neill, et al., Eur. J. Pharmacol. 486:163-174 (2004).
Kent, et al., Mol. Psychiatry 10:939-943 (2005).
Riikonen, et al., J. Child Neurol. 18:693-697 (2003).
Chang, et al., Neuron 49:341-348 (2006).
Ito et al., J. Physiol. 424:533 543 (1990).
Staubli et al., Psychobiology 18:377 381 (1990).
Xiao et al., Hippocampus 1:373 380 (1991).
Guenzi and Zanetti, J. Chromatogr. 530:397 406 (1990).
Himori, et al., Pharmacology Biochemistry and Behavior 47:219-225 (1994).
Pizzi et al., J. Neurochem. 61:683-689 (1993).
Nakamura and Shirane, Eur. J. Pharmacol. 380: 81-89 (1999).
Spignoli and Pepeu, Pharmacol. Biochem. Behav. 27:491-495 (1987).
Hall and Von Voigtlander, Neuropharmacology 26:1573-1579(1987).
Kessler et al., Brain Res. 560: 337 341 (1991).
Staubli et al., Hippocampus 2: 4958 (1992).
Sirvio et al., Neuroscience 74: 1025-1035 (1996).
Chapter 7, Neuroscience, edited by Dale Purves, Sinauer Associates, Inc., Sunderland, MA 1997.
Diagnostic and Statistical Manual of Mental Disorders, Fourth Edition (DSM IV), pp. 317-391, 2010.
Diagnostic and Statistical Manual of Mental Disorders, Fourth Edition (DSM IV) Sections 293.81, 293.82, 295.10, 295.20, 295.30, 295.40, 295.60, 295.70, 295.90, 297.1, 297.3, 298.8, 2010.

* cited by examiner

DI-SUBSTITUTED AMIDES FOR ENHANCING GLUTAMATERGIC SYNAPTIC RESPONSES

RELATED APPLICATIONS

This patent application claims the benefit of priority of provisional application nos. U.S. 60/930,633, filed May 17, 2007 and U.S. 60/958,069, filed Jul. 2, 2007, both of identical title to the present application, each of which applications is incorporated by reference in its entirety herein.

FIELD OF THE INVENTION

This invention relates to compounds, pharmaceutical compositions and methods for use in the prevention and treatment of cerebral insufficiency, including enhancement of receptor functioning in synapses in brain networks responsible for various behaviors. These brain networks are involved in basic functions such as breathing, to more complex functions such as memory and cognition. Imbalances in neuronal activities between different brain regions may lead to a number of disorders, including psychiatric and neurological disorders, including memory impairment, Parkinson's disease, schizophrenia, attention deficit and affective or mood disorders, respiratory depression and in disorders wherein a deficiency in neurotrophic factors is implicated. In a particular aspect, the invention relates to compounds useful for treatment of such conditions, and methods of using these compounds for such treatment.

BACKGROUND OF THE INVENTION

The release of glutamate at synapses at many sites in mammalian forebrain stimulates two classes of postsynaptic ionotropic glutamate receptors. These classes are usually referred to as AMPA and N-methyl-D-aspartic acid (NMDA) receptors. AMPA receptors mediate a voltage independent fast excitatory post-synaptic current (the fast EPSC), whereas NMDA receptors generate a voltage-dependent, slow excitatory current. Studies carried out in slices of hippocampus or cortex, indicate that the AMPA receptor mediated fast EPSC is generally the dominant component by far at most glutamatergic synapses, and activation of AMPA receptors is usually a prerequisite for NMDA receptors activation. AMPA receptors are expressed throughout the central nervous system. These receptors are found in high concentrations in the superficial layers of neocortex, in each of the major synaptic zones of hippocampus, and in the striatal complex, as reported by Monaghan et al., in *Brain Research* 324:160-164 (1984). Studies in animals and humans indicate that these structures organize complex perceptual-motor processes and provide the substrates for higher-order behaviors. Thus, AMPA receptors mediate transmission in those brain networks responsible for a host of cognitive activities. In addition, AMPA receptors are expressed in brain regions that regulate the inspiratory drive responsible for control of breathing (Paarmann et al, *Journal of Neurochemistry,* 74: 1335-1345 (2000).

For the reasons set forth above, drugs that modulate and thereby enhance the functioning of AMPA receptors could have significant benefits for intellectual performance as well as reversal of respiratory depression induced by pharmacological agents such as opioids and opiates, or other means. Such drugs should also facilitate memory encoding. Experimental studies, such as those reported by Arai and Lynch, *Brain Research* 598:173-184 (1992), indicate that increasing the size of AMPA receptor-mediated synaptic response(s) enhances the induction of long-term potentiation (LTP). LTP is a stable increase in the strength of synaptic contacts that follows repetitive physiological activity of a type known to occur in the brain during learning.

Compounds that enhance the functioning of the AMPA subtype of glutamate receptors facilitate the induction of LTP and the acquisition of learned tasks as measured by a number of paradigms. See, for example, Granger et al., *Synapse* 15:326-329 (1993); Staubli et al., *PNAS* 91:777-781 (1994); Arai et al., Brain Res. 638:343-346 (1994); Staubli et al., *PNAS* 91:11158-11162 (1994); Shors et al., *Neurosci. Let.* 186:153-156 (1995); Larson et al., *J. Neurosci.* 15:8023-8030 (1995); Granger et al., *Synapse* 22:332-337 (1996); Arai et al., *JPET* 278:627-638 (1996); Lynch et al., *Internat. Clin. Psychopharm.* 11:13-19 (1996); Lynch et al., *Exp. Neurology* 145:89-92 (1997); Ingvar et al., *Exp. Neurology* 146:553-559 (1997); Hampson, et al., *J. Neurosci.* 18:2748-2763 (1998); Porrino et al., *PLoS Biol* 3(9): 1-14 (2006) and Lynch and Rogers, U.S. Pat. No. 5,747,492. There is a considerable body of evidence showing that LTP is the substrate of memory. For example, compounds that block LTP interfere with memory formation in animals, and certain drugs that disrupt learning in humans antagonize the stabilization of LTP, as reported by del Cerro and Lynch, *Neuroscience* 49: 1-6 (1992). Learning a simple task induces LTP in hippocampus that occludes LTP generated by high frequency stimulation (Whitlock et al., Science 313:1093-1097 (2006)) and a mechanism that maintains LTP sustains spatial memory (Pastalkova, et al., Science 313:1141-1144 (2006)). Of significant importance to the field of learning is the finding that in vivo treatments with a positive AMPA-type glutamate receptor modulator restores stabilization of basal dendritic LTP in middle-aged animals (Rex, et al., *J. Neurophysiol.* 96:677-685 (2006)).

Drugs that enhance the functioning of the AMPA receptor can effectively reverse opioid- and barbiturate-induced respiratory depression without reversing the analgesic response (Ren et al, *American Journal of Respiratory and Critical Care Medicine,* 174: 1384-1391 (2006). Therefore these drugs may be useful in preventing or reversing opioid-induced respiratory depression and for alleviating other forms of respiratory depression including sedative use and sleep apnea. Excitatory synaptic transmission provides a major pathway by which neurotrophic factors are increased within specific brain regions. As such, potentiation of AMPA receptor function by modulators has been found to increase levels of neurotrophins, particularly brain derived neurotrophic factor, or BDNF. See, for example, Lauterborn, et al., *J. Neurosci.* 20:8-21 (2000); Gall, et al., U.S. Pat. No. 6,030,968; Lauterborn, et al., JPET 307:297-305 (2003); and Mackowiak, et al., *Neuropharmacology* 43:1-10 (2002). Other studies have linked BDNF levels to a number of neurological disorders, such as Parkinson's disease, Attention Deficit Hyperactivity Disorder (ADHD), autism, Fragile-X Syndrome, and Rett Syndrome (RTT). See, for example, O'Neill, et al., *Eur. J. Pharmacol.* 486:163-174 (2004); Kent, et al., *Mol. Psychiatry.* 10:939-943 (2005); Riikonen, et al., *J. Child Neurol.* 18:693-697 (2003) and Chang, et al., *Neuron* 49:341-348 (2006). Thus, AMPA receptor potentiators may be useful for the treatment of these, as well as other, neurological diseases that are the result of a glutamatergic imbalance or a deficit in neurotrophic factors.

A prototype for a compound that selectively facilitates the AMPA receptor has been described by Ito et al., *J. Physiol.* 424:533-543 (1990). These authors found that the nootropic drug aniracetam (N-anisoyl-2-pyrrolidinone) increases currents mediated by brain AMPA receptors expressed in Xenopus oocytes without affecting responses by γ-aminobutyric acid (GABA), kainic acid (KA), or NMDA receptors. Infusion of aniracetam into slices of hippocampus was also shown to substantially increase the size of fast synaptic potentials without altering resting membrane properties. It has since been confirmed that aniracetam enhances synaptic responses at several sites in hippocampus, and that it has no effect on NMDA-receptor mediated potentials (Staubli et al., *Psychobiology* 18:377-381 (1990) and Xiao et al., *Hippocampus* 1:373-380 (1991)).

Aniracetam has been found to have an extremely rapid onset and washout, and can be applied repeatedly with no apparent lasting effects, which are desirable features for behaviorally-relevant drugs. Aniracetam does present several disadvantages, however. The peripheral administration of aniracetam is not likely to influence brain receptors. The drug works only at high concentrations (approx. 1000 μM), and about 80% of the drug is converted to anisoyl-GABA following peripheral administration in humans (Guenzi and Zanetti, *J. Chromatogr.* 530:397-406 (1990)). The metabolite, anisoyl-GABA, has been found to have less activity than aniracetam. In addition to these issues, aniracetam has putative effects on a plethora of other neurotransmitter and enzymatic targets in the brain, which makes uncertain the mechanism of any claimed therapeutic drug effect. See, for example, Himori, et al., *Pharmacology Biochemistry and Behavior* 47:219-225 (1994); Pizzi et al., *J. Neurochem.* 61:683-689 (1993); Nakamura and Shirane, *Eur. J. Pharmacol.* 380: 81-89 (1999); Spignoli and Pepeu, *Pharmacol. Biochem. Behav.* 27:491-495 (1987); Hall and Von Voigtlander, *Neuropharmacology* 26:1573-1579 (1987); and Yoshimoto et al., *J. Pharmacobiodyn.* 10:730-735 (1987).

A class of AMPA receptor-enhancing compounds that does not display the low potency and inherent instability characteristic of aniracetam has been described (Lynch and Rogers, U.S. Pat. No. 5,747,492). These compounds, termed "Ampakines"[R], can be substituted benzamides which include, for example, 6-(piperidin-1-ylcarbonyl)quinoxaline (CX516; Ampalex[R]). Typically, they are chemically more stable than aniracetam and show improved bio-availability. CX516 is active in animal tests used to detect efficacious drugs for the treatment of memory disorders, schizophrenia, and depression. In three separate clinical trials, CX516 showed evidence for efficacy in improving various forms of human memory (Lynch et al., *Internat. Clin. Psychopharm.* 11:13-19 (1996); Lynch et al., *Exp. Neurology* 145:89-92 (1997); Ingvar et al., *Exp. Neurology* 146:553-559 (1997)).

Another class of Ampakines, benzoxazines, has been discovered to have very high activity in in vitro and in vivo models for assessing the probability of producing cognition enhancement (Rogers and Lynch; U.S. Pat. No. 5,736,543). The substituted benzoxazines are rigid benzamide analogues with different receptor modulating properties from the flexible benzamide, CX516.

Certain substituted 2.1.3 benzoxadiazole compounds have been found to be significantly and surprisingly more potent in animal models of attention deficit hyperactivity disorder (ADHD), schizophrenia and cognition than previously disclosed compounds in US 2002/0055508 and US 2002/0099050. This new class of N,N-disubstituted amides (I) display significant activity for enhancing AMPA mediated glutamateric synaptic responses.

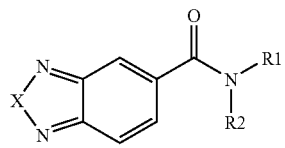

SUMMARY OF THE INVENTION

The present invention includes, in one aspect, a compound as shown by structure I, and described in Section II of the Detailed Description, which follows. Administration of compounds of this class has been found to enhance AMPA mediated glutamatergic synaptic responses and significantly improve the behavior of rodents in the d-amphetamine stimulated locomotion assay. This behavioral assay has proven useful in assessing the efficacy of neuroleptic drugs for the treatment of schizophrenia and ADHD. The compounds are significantly and surprisingly more potent than previously described compounds in increasing glutamatergic synaptic responses in vivo. This activity translates into pharmaceutical compounds and corresponding methods of use, including treatment methods, which utilize significantly lower concentrations of the present compounds compared to prior art compositions. In addition, compounds within the present invention demonstrate improved pharmacokinetic properties compared with previously described compounds and have good oral bioavailability.

The ability of the compounds of the invention to increase AMPA receptor-mediated responses makes the compounds useful for a variety of purposes. These include facilitating the learning of behaviors dependent upon glutamate receptors, treating conditions in which AMPA receptors, or synapses utilizing these receptors, are reduced in numbers or efficiency, and enhancing excitatory synaptic activity in order to restore an imbalance between brain sub-regions or increase the levels of neurotrophic factors.

In another aspect, the invention includes a method for the treatment of a mammalian subject suffering from a hypoglutamatergic condition, or from a deficiency in the number or strength of excitatory synapses, or in the number of AMPA receptors, such that memory or other cognitive functions are impaired. Such conditions may also cause a cortical/striatal imbalance, leading to schizophrenia or schizophreniform behavior.

In another aspect, the invention includes a method for reducing or inhibiting respiratory depression in a subject having respiratory depression, comprising administering to the subject an amount of a compound of the invention, the amount being sufficient to reduce or inhibit respiratory depression. In one embodiment of the invention, the subject is a human. In another embodiment, the subject is a mammal. Also claimed is a method for reducing or inhibiting respiratory depression comprising administering to the subject an amount of a compound of the invention in combination with an opioid analgesic; examples of such opiates include but are not limited to, alfentanil and fentanyl.

In another aspect, the invention includes a method for reducing or inhibiting breathing-related sleep disorders or sleep apnea in a subject having sleep apnea, comprising administering to the subject an amount of a compound of the invention, the amount being sufficient to reduce or inhibit the breathing related sleep disorder.

According to the methods, such a subject is treated with an effective amount of a compound as shown by structure I, and described in Section II of the Detailed Description, following, in a pharmaceutically acceptable carrier. These and other objects and features of the invention will become more fully apparent when the following detailed description of the invention is read in conjunction with the accompanying drawings.

DETAILED DESCRIPTION OF THE INVENTION

I. Definitions

The terms below have the following meanings unless indicated otherwise. Other terms not specifically defined herein which are used to describe the present invention have the same meaning given to those terms within the context of their use by those skilled in the art.

The term "alkyl" is used herein to refer to a fully saturated monovalent radical containing carbon and hydrogen, and which may be a straight chain, branched or cyclic. Examples of alkyl groups are methyl, ethyl, n-butyl, n-heptyl, isopropyl, 2-methylpropyl.

The symbol

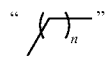

is used to describe an alkylene group where the junction between the two lines represents a methylene ($CH_2$) group and n is an integer from 0 to 7. The integer of n=0 is used to indicate that the methylene group is non-existent.

The term "cycloalkyl" is used herein to refer to a fully saturated monovalent radical containing up to 8 carbons and hydrogen in a ring. Examples of cycloalkyl groups are cyclopropyl, cyclobutyl, cyclopentyl, cyclohexyl and cycloheptyl. The term cycloalkyl, when used in context, may also refer to a cycloalkyl group which contains a heteroatom B group (heterocycle).

The term "bicycloalkyl" is used herein to refer to a fully saturated monovalent radical containing up to 10 carbons and hydrogen in a bicyclic ring. Examples of bicycloalkyl groups are bicyclo[2.2.2]octyl, bicyclo[2.2.1]heptyl, bicyclo[2.2.3] nonyl and bicylo[3.2.1]octyl.

The term "azabicycloalkyl" is used herein to refer to a fully saturated monovalent radical containing up to 10 carbons and hydrogen and 1 nitrogen atom in a bicyclic ring. Examples of azabicycloalkyl groups a include 1-azabicyclo[2.2.2]octyl, 2-azabicyclo[2.2.2]octyl, 1-azabicyclo[2.2.1]heptyl, 2-azabicyclo[2.2.1]heptyl and 1-azabicylo[3.2.1]octyl.

The term "alkenyl" is used herein to refer to a monovalent radical containing carbon and hydrogen that contains one or two sites of un-saturation, and which may be a straight chain, branched or cyclic. Examples of alkenyl groups are ethenyl, n-butenyl, n-heptenyl, isopropenyl, cyclopentenyl, cyclopentenylethyl and cyclohexenyl.

The term "substituted" with reference to "substituted alkyl" groups (including cycloalkyl and bicycloalkyl groups), "substituted alkenyl" groups and "substituted alkynyl" groups, among other related substituted groups (e.g., carboxyalkyl, sulfonylalkyl), refers to one or more functional groups (containing from 1-8 carbon atoms, 1-7 carbon atoms, 1-6 carbon atoms, 1-3 carbon atoms, 2-8 carbon atoms, 2-7 carbon atoms, 2-6 carbon atoms, 3-8 carbon atoms, etc. depending upon the substituent) which are used as a substitute for H, such as alkyl containing from 1-8 carbon atoms including cycloalkyl containing from 3-7 carbon atoms, aryl, substituted aryl, acyl, halogen (i.e., alkyl halos, e.g., $CF_3$), amido, thioamido cyano, nitro, alkynyl, azido, hydroxy, alkoxy, alkoxyalkyl, amino, alkyl and dialkyl-amino, acylamino, acyloxy, aryloxy, aryloxyalkyl, carboxyalkyl, carboxamido, thio, thioethers, both saturated and unsaturated cyclic hydrocarbons, heterocycles and the like, or as otherwise described herein (see the term "substituted" hereinbelow).

The term "aryl" refers to a substituted or unsubstituted monovalent aromatic radical having a single ring (e.g., phenyl) or multiple condensed rings (e.g., naphthyl). Other examples include heterocyclic aromatic ring groups having one or more nitrogen, oxygen, or sulfur atoms in the ring, such as oxazolyl, isoxazolyl, pyrazolyl, thiazolyl, thiadiazolyl, tetrazolyl, pyridazinyl, pyrimidyl, benzofuryl, benzothienyl, benzimidazolyl, benzoxazolyl, benzothiazolyl, quinolyl, isoquinolyl, imidazolyl, furyl, pyrrolyl, pyridyl, thienyl and indolyl. Thus, the term "aryl" subsumes the term "heteroaryl" as such terms are used in context.

The term "substituted" as used in the term "substituted aryl, substituted aromatic, substituted heteroaryl, or substituted heteroaromatic", herein signifies that one or more substituents may be present, said substituents being selected from atoms and groups, which when present do not prevent the compound from functioning as a potentiator of AMPA receptor function. Examples of substituents that may be present in a substituted aromatic or heteroaromatic group include, but are not limited to, groups such as ($C_1$-$C_7$) alkyl, ($C_1$-$C_7$) acyl, aryl, heteroaryl, substituted aryl and heteroaryl, halogen, cyano, nitro, amido (optionally substituted with one or two $C_1$-$C_7$ alkyl groups), thioamido (optionally substituted with one or two $C_1$-$C_7$ alkyl groups), azido, ($C_2$-$C_7$) alkynyl, ($C_1$-$C_7$) alkylhalos (e.g., $CF_3$), hydroxy, ($C_1$-$C_7$) alkoxy, ($C_2$-$C_8$) alkoxyalkyl, amino, ($C_1$-$C_7$) alkyl and dialkyl amino, ($C_1$-$C_7$) acylamino, ($C_1$-$C_7$) acyloxy, aryloxy, ($C_1$-$C_7$) aryloxyalkyl, ($C_1$-$C_7$) carboxyalkyl, carboxamido, thio, ($C_1$-$C_7$) thioethers, both saturated and unsaturated ($C_3$-$C_8$) cyclic hydrocarbons, ($C_3$-$C_8$) heterocycles and the like. It is noted that each of the substituents disclosed herein may themselves be substituted.

"Heterocycle" or "heterocyclic" refers to a carbocyclic ring wherein one or more carbon atoms have been replaced with one or more heteroatoms (up to 6 atoms, up to 4 atoms, 1, 2 or 3 atoms) such as nitrogen, oxygen or sulfur. Examples of heterocycles include, but are not limited to, piperidine, pyrrolidine, morpholine, thiomorpholine, piperazine, tetrahydrofuran, tetrahydropyran, 2-pyrrolidinone, δ-valerolactam, δ-valerolactone and 2-ketopiperazine.

The term "substituted heterocycle" refers to a heterocycle as just described that contains one or more functional groups such as lower alkyl, acyl, aryl, cyano, halogen, amido, thioamido, azido, hydroxy, alkoxy, alkoxyalkyl, amino, alkyl and dialkyl-amino, acylamino, acyloxy, aryloxy, aryloxyalkyl, carboxyalkyl, carboxamido, thio, thioethers, both saturated and unsaturated cyclic hydrocarbons, heterocycles and the like, as otherwise described herein.

The term "compound" is used herein to refer to any specific chemical compound disclosed herein. Within its use in context, the term generally refers to a single compound, but in certain instances may also refer to stereoisomers and/or optical isomers (including enantiopure compounds, enantiomerically enriched compounds and racemic mixtures) of disclosed compounds.

The term "effective amount" refers to the amount of a selected compound of formula I that is used within the context of its intended use to effect an intended result, for example, to enhance glutamatergic synaptic response by increasing AMPA receptor activity. The precise amount used will vary depending upon the particular compound selected and its intended use, the age and weight of the subject, route of administration, and so forth, including the duration of its use, but may be easily determined by routine experimentation. In the case of the treatment of a condition or disease state, an effective amount is that amount which is used to effectively treat the particular condition or disease state.

The term "pharmaceutically acceptable carrier" refers to a carrier or excipient which is not unacceptably toxic to the subject to which it is administered. Pharmaceutically acceptable excipients are described at length by E. W. Martin, in "Remington's Pharmaceutical Sciences."

A "pharmaceutically acceptable salt" of an amine compound, such as those contemplated in the current invention, is an ammonium salt having as counter ion an inorganic anion such as chloride, bromide, iodide, sulfate, sulfite, nitrate, nitrite, phosphate, and the like, or an organic anion such as acetate, malonate, pyruvate, propionate, fumarate, cinnamate, tosylate, and the like.

The term "patient" or "subject" is used throughout the specification to describe an animal, generally a mammalian animal, including a human, to whom treatment or use with the compounds or compositions according to the present invention is provided. For treatment or use with/or of those conditions or disease states which are specific for a specific animal (especially, for example, a human subject or patient), the term patient or subject refers to that particular animal.

The term "sensory motor problems" is used to describe a problem which arises in a patient or subject from the inability to integrate external information derived from the five known senses in such a way as to direct appropriate physical responses involving movement and action.

The term "cognitive task" or "cognitive function" is used to describe an endeavor or process by a patient or subject that involves thought or knowing. The diverse functions of the association cortices of the parietal, temporal and frontal lobes, which account for approximately 75% of all human brain tissue, are responsible for much of the information processing that goes on between sensory input and motor output. The diverse functions of the association cortices are often referred to as cognition, which literally means the process by which we come to know the world. Selectively attending to a particular stimulus, recognizing and identifying these relevant stimulus features and planning and experiencing the response are some of the processes or abilities mediated by the human brain which are related to cognition.

The term "brain network" is used to describe different anatomical regions of the brain that communicate with one another via the synaptic activity of neuronal cells.

The term "AMPA receptor" refers to an aggregate of proteins found in some membranes, is which allows positive ions to cross the membrane in response to the binding of glutamate or AMPA (DL-$\alpha$-amino-3-hydroxy-5-methyl-4-isoxazolepropionic acid), but not NMDA.

The term "excitatory synapse" is used to describe a cell-cell junction at which release of a chemical messenger by one cell causes depolarization of the external membrane of the other cell. An excitatory synapse describes a postsynaptic neuron which has a reversal potential that is more positive than the threshold potential and consequently, in such a synapse, a neurotransmitter increases the probability that an excitatory post synaptic potential will result (a neuron will fire producing an action potential). Reversal potentials and threshold potentials determine postsynaptic excitation and inhibition. If the reversal potential for a post synaptic potential ("PSP") is more positive than the action potential threshold, the effect of a transmitter is excitatory and produces an excitatory post synaptic potential ("EPSP") and the firing of an action potential by the neuron. If the reversal potential for a post synaptic potential is more negative than the action potential threshold, the transmitter is inhibitory and may generate inhibitory post synaptic potentials (IPSP), thus reducing the likelihood that a synapse will fire an action potential. The general rule for postsynaptic action is: if the reversal potential is more positive than threshold, excitation results; inhibition occurs if the reversal potential is more negative than threshold. See, for example, Chapter 7, *NEUROSCIENCE*, edited by Dale Purves, Sinauer Associates, Inc., Sunderland, Mass. 1997.

The term "motor task" is used to describe an endeavor taken by a patient or subject that involves movement or action.

The term "perceptual task" is used to describe an act by a patient or subject of devoting attention to sensory inputs.

The term "synaptic response" is used to describe biophysical reactions in one cell as a to consequence of the release of chemical messengers by another cell with which it is in close contact.

The term "hypoglutamatergic condition" is used to describe a state or condition in which transmission mediated by glutamate (or related excitatory amino acids) is reduced to below normal levels. Transmission consists of the release of glutamate, binding to post synaptic receptors, and the opening of channels integral to those receptors. The end point of the hypoglutamatergic condition is reduced excitatory post synaptic current. It can arise from any of the three above noted phases of transmission. Conditions or disease states which are considered hypoglutamatergic conditions and which can be treated using the compounds, compositions and methods according to the present invention include, for example, loss of memory, dementia, depression, attention disorders, sexual dysfunction, movement disorders, including Parkinson's disease, schizophrenia or schizophreniform behavior, memory and learning disorders, including those disorders which result from aging, trauma, stroke and neurodegenerative disorders, such as those associated with drug-induced states, neurotoxic agents, Alzheimer's disease and aging, respiratory depression and sleep apnea. These conditions are readily recognized and diagnosed by those of ordinary skill in the art.

The term "cortico-striatal imbalance" is used to describe a state in which the balance of neuronal activities in the interconnected cortex and underlying striatal complex deviates from that normally found. 'Activity' can be assessed by electrical recording or molecular biological techniques. Imbalance can be established by applying these measures to the two structures or by functional (behavioral or physiological) criteria.

The term "affective disorder" or "mood disorder" describes the condition when sadness or elation is overly intense and continues beyond the expected impact of a stressful life event, or arises endogenously. As used herein, the term "effective disorder" embraces all types of mood disorders as described in, for example, *Diagnostic and Statistical Manual of Mental Disorders*, Fourth Edition (DSM IV), pages 317-391.

The term "schizophrenia" is used to describe a condition which is a common type of psychosis, characterized by a disorder in the thinking processes, such as delusions and hallucinations, and extensive withdrawal of the individual's interest from other people and the outside world, and the investment of it in his or her own. Schizophrenia is now considered a group of mental disorders rather than a single entity, and distinction is made between reactive and process schizophrenias. As used herein, the term schizophrenia or "schizophreniform" embraces all types of schizophrenia, including ambulatory schizophrenia, catatonic schizophrenia, hebephrenic schizophrenia, latent schizophrenia, process schizophrenia, pseudoneurotic schizophrenia, reactive schizophrenia, simple schizophrenia, and related psychotic disorders which are similar to schizophrenia, but which are not necessarily diagnosed as schizophrenia per se. Schizophrenia and other psychotic disorders may be diagnosed using guidelines established in, for example, *Diagnostic and Statistical Manual of Mental Disorders*, Fourth Edition (DSM IV) Sections 293.81, 293.82, 295.10, 295.20, 295.30, 295.40, 295.60, 295.70, 295.90, 297.1, 297.3, 298.8.

The term "brain function" is used to describe the combined tasks of perceiving, integrating, filtering and responding to external stimuli and internal motivational processes.

The term "impaired" is used to describe a function working at a level that is less than normal. Impaired functions can be significantly impacted such that a function is barely being carried out, is virtually non-existent or is working in a fashion that is significantly less than normal. Impaired functions may also be sub-optimal. The impairment of function will vary in severity from patient to patient and the condition to be treated.

The term "respiratory depression" as used herein refers to a variety of conditions characterized by reduced respiratory frequency and inspiratory drive to cranial and spinal motor neurons. Specifically, respiratory depression refers to conditions where the medullary neural network associated with respiratory rhythm generating activity does not respond to accumulating levels of $PCO_2$ (or decreasing levels of $PO_2$) in the blood and subsequently under stimulates motorneurons controlling lung musculature.

The term "sleep apnea" as used herein refers to breathing-related sleep disorders of which there are two types: central and obstructive. Central Sleep Apnea is defined as a neurological condition causing cessation of all respiratory effort during sleep, usually with decreases in blood oxygen saturation, if the brainstem center controlling breathing shuts down there's no respiratory effort and no breathing. The person is aroused from sleep by an automatic breathing reflex, so may end up getting very little sleep at all. Obstructive sleep apnea is characterized by repetitive pauses in breathing during sleep due to the obstruction and/or collapse of the upper airway and followed by an awakening to breathe. Respiratory effort continues during the episodes of apnea.

The term "pro-drug" as used herein refers to a metabolically labile derivative that is pharmacologically inactive in the parent form but that is rapidly metabolized in human or animal plasma to a pharmacologically active form. Examples of pro-drugs as used herein include but in no way are limited to, where applicable, ester derivatives of hydroxyl containing moieties or amide derivatives of amine containing moieties, such esters or amides include, but are not limited to those formed from substituted or un-substituted natural or un-natural amino acids.

The term "co-administration" or "combination therapy" is used to describe a therapy in which at least two active compounds in effective amounts are used to treat a disease state or condition as otherwise described herein at the same time. Although the term co-administration preferably includes the administration of two active compounds to the patient at the same time, it is not necessary that the compounds be administered to the patient at the same time, although effective amounts of the individual compounds will be present in the patient at the same time.

II. Compounds of the Present Invention

The present invention is directed, in one aspect, to compounds having the property of enhancing AMPA receptor function. These are compounds having the structure I, below:

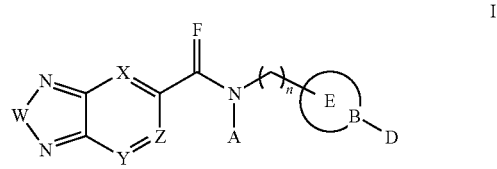

wherein:
W is oxygen, sulfur or CH═CH;
X, Y and Z are independently selected from the group consisting of —N, or —CR, wherein:
R is H, —Br, —Cl, —F, —CN, —$NO_2$, —$OR^1$, —$SR^1$, —$NR^1_2$, —$C_1$-$C_6$ branched or un-branched alkyl, which may be un-substituted or substituted,
wherein:
$R^1$ is H, —$C_1$-$C_6$ branched or un-branched alkyl which, may be un-substituted or substituted, F═O or S,
A is H, or —$C_1$-$C_6$ branched or un-branched alkyl, which may be un-substituted or substituted, —$C_2$-$C_6$ branched or un-branched alkenyl, which may be un-substituted or substituted, —$C_2$-$C_6$ branched or un-branched alkynyl, which may be un-substituted or substituted, —$C_3$-$C_7$ cycloalkyl which may be un-substituted or substituted, —$C_3$-$C_7$ alkylcycloalkyl which may be un-substituted or substituted, aryl or heterocycle which may be un-substituted or substituted, alkylaryl which may be un-substituted or substituted, alkylheterocycle which may be un-substituted or substituted
n=0, 1, 2, 3, 4, 5, or 6;

is a —$C_3$-$C_7$ cycloalkyl, which may be un-substituted or substituted, a —$C_4$-$C_7$ azacycloalkyl, which may be un-substituted or substituted, a $C_7$-$C_{10}$ bicycloalkyl which may be un-substituted or substituted, a —$C_7$-$C_{10}$ azabicycloalkyl which may be un-substituted or substituted, aryl which may be un-substituted or substituted or a heterocycle which may be un-substituted or substituted;
B is C═, C—$R^a$, O, N, S, C═O, S═O or $SO_2$;
$R^a$ is H, a halogen (preferably F), OH, O-alkyl, cyano, or a —$C_1$-$C_6$ alkyl group which is un-substituted or substituted and which optionally, forms a $C_3$-$C_7$ cycloalkyl group with D; and D is absent when B is O, S, S═O, C═O or $SO_2$, or if present, is bonded to B when B is C═, —C—$R^a$ or N, and is H, a halogen (preferably F), $OR^b$, a —$C_1$-$C_6$ branched or un-branched alkyl, which may be un-substituted or substituted and which optionally, forms a $C_3$-$C_7$ cycloalkyl group with $R^a$, a —$C_2$-$C_6$ branched or un-branched alkenyl, which may be un-substituted or substituted, a —$C_2$-$C_6$ branched or un-branched alkynyl, which may be un-substituted or substituted, a —$C_3$-$C_7$ cycloalkyl which may be un-substituted or substituted, an aryl which may be un-substituted or substituted, a heterocycle which may be un-substituted or substituted, a —$C_2$-$C_7$ carboxyalkyl which may be un-substituted or substituted, a carboxyaryl which may be un-substituted or substituted, a carboxyheteroaryl which may be un-substituted or substituted, a —$C_1$-$C_7$ sulfonylalkyl which may be un-substituted or substituted, a sulfonylaryl which may be un-substituted or substituted or a sulfonylheteroaryl which may be un-substituted or substituted, or when B is —C—$R^a$, $R^a$ and D optionally form a =N—$R^c$ or a =N—$OR^c$ group with B, wherein $R^c$ is H or an unsubstituted or substituted $C_1$-$C_7$ alkyl group, or when B is —C—$R^a$, $R^a$ and D optionally form a =N—$R^c$ or a =N—$OR^c$ group with B, wherein $R^c$ is H or an unsubstituted or substituted $C_1$-$C_7$ alkyl group; and $R^b$ is H, a —$C_1$-$C_7$ alkyl group which may be branched or un-branched, un-substituted or substituted or a —$C_2$-$C_7$ acyl group which may be un-substituted or substituted;

or a pharmaceutically acceptable salt, solvate, pro-drug or polymorph thereof.

Preferred embodiments include compounds according to formula II below:

II wherein:

A is —$C_1$-$C_6$ branched or un-branched alkyl, which may be un-substituted or substituted, a $C_3$-$C_7$ cycloalkyl which may be un-substituted or substituted;

n is 0, 1, 2, or 3;

B is C—$R^a$, O or C=O;

$R^a$ is H, F, —OH or alkyl and

D is absent (when B is O), is H or OH when $R^a$ is H or alkyl, or is F when $R^a$ is F, or a pharmaceutically acceptable salt, solvate, or polymorph thereof.

A preferred embodiment includes compounds according to formula III below:

III wherein:

A is a $C_1$-$C_6$ alkyl which may be substituted or un-substituted;

B is C—$R^a$, O or C=O;

$R^a$ is H, F, —OH or alkyl and

D is absent (when B is O), is H or OH when $R^a$ is H or alkyl, or is F when $R^a$ is F, or a pharmaceutically acceptable salt, solvate, or polymorph thereof.

A further preferred embodiment includes compounds according to formula IV below:

IV wherein:

A is a $C_1$-$C_6$ alkyl which may be substituted or un-substituted, n is 0, 1 or 2, or a pharmaceutically acceptable salt, solvate, or polymorph thereof.

A further preferred embodiment includes compounds according to formula V below:

V wherein:

A is a $C_1$-$C_6$ alkyl which may be substituted or un-substituted, $R^1$ is H, F, or $C_1$-$C_4$ alkyl, $R^2$ is H, F, CN, a heterocycle which may be substituted or un-substituted or $OR^3$, $R^3$ is H, $C_1$-$C_6$ alkyl which may be substituted or un-substituted, or a pharmaceutically acceptable salt, solvate, or polymorph thereof.

A further preferred embodiment includes compounds according to formula VI below:

VI wherein:

A is a $C_1$-$C_6$ alkyl which may be substituted or un-substituted,

R is H, or $C_1$-$C_4$ alkyl, or a pharmaceutically acceptable salt, solvate, or polymorph thereof.

A yet further preferred embodiment includes compounds according to formula VII below:

VII wherein:

B is C—$R^a$, O or C=O;

$R^a$ is H, F, —OH or alkyl and

D is absent (when B is O), is H or OH when $R^a$ is H or alkyl, or is F when $R^a$ is F, or a pharmaceutically acceptable salt, solvate, or polymorph thereof.

In a yet further preferred embodiment compounds are included according to formula VIII below:

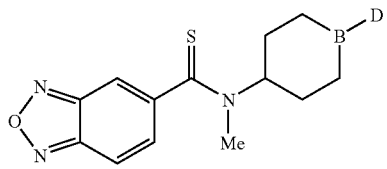

wherein:
B is C—R$^a$, O or C=O;
R$^a$ is H, F, —OH or alkyl and
D is absent (when B is O), is H or OH when R$^a$ is H or alkyl, or is F when R$^a$ is F, or a pharmaceutically acceptable salt, solvate, or polymorph thereof.

A yet further preferred embodiment includes compounds according to formula IX below:

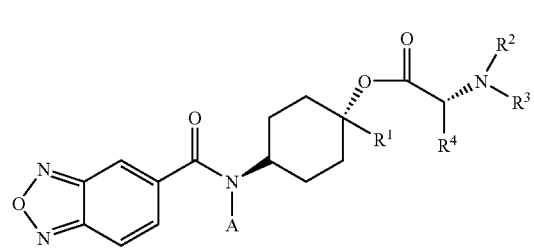

wherein:
A is a $C_1$-$C_6$ alkyl which may be substituted or un-substituted,
R$^1$ is H, or $C_1$-$C_4$ alkyl,
R$^2$ is H, or a $C_1$-$C_6$ alkyl which may be substituted or un-substituted,
R$^3$ is H, or a $C_1$-$C_6$ alkyl which may be substituted or un-substituted,
R$^4$ is H, or a $C_1$-$C_6$ alkyl which may be substituted or un-substituted, or a pharmaceutically acceptable salt, solvate, or polymorph thereof.

In a further aspect, the present invention provides compounds of Formulas I-IX selected from:
N-Cycloheptyl-N-methyl-[2,1,3]-benzoxadiazole-5-carboxamide
N-(4,4-Dimethylcyclohexyl-N-methyl-[2,1,3]-benzoxadiazole-5-carboxamide
N-Methyl-N-spiro[2.5]oct-6-yl[2,1,3]-benzoxadiazole-5-carboxamide
N-Cyclohexyl-N-methyl-[2,1,3]-benzoxadiazole-5-carboxamide
N-Cyclopentyl-N-methyl-[2,1,3]-benzoxadiazole-5-carboxamide
N-Cyclobutyl-N-methyl-[2,1,3]-benzoxadiazole-5-carboxamide
N-Cyclohexyl-[2,1,3]-benzoxadiazole-5-carboxamide
N-Cyclopentyl-[2,1,3]-benzoxadiazole-5-carboxamide
N-Cyclobutyl-[2,1,3]-benzoxadiazole-5-carboxamide
N-(cis-4-Cyanocyclohexyl)-N-methyl-[2,1,3]-benzoxadiazole-5-carboxamide
N-(trans-4-Cyanocyclohexyl)-N-methyl-[2,1,3]-benzoxadiazole-5-carboxamide
N-Methyl-N-tetrahydro-2H-pyran-4-yl[2,1,3]-benzoxadiazole-5-carboxamide
N-D$_3$-Methyl-N-tetrahydro-2H-pyran-4-yl-[2,1,3]-benzoxadiazole-5-carboxamide
N-(Tetrahydro-2H-pyran-4-yl)-[2,1,3]-benzoxadiazole-5-carboxamide
N-(Tetrahydro-2H-pyran-3-yl)-[2,1,3]-benzoxadiazole-5-carboxamide
N-Methyl-N-(tetrahydro-2H-pyran-3-yl)-[2,1,3]-benzoxadiazole-5-carboxamide
N-Ethyl-N-tetrahydro-2H-pyran-4-yl-[2,1,3]-benzoxadiazole-5-carboxamide
N-Cyclohexyl-N-ethyl-[2,1,3]-benzoxadiazole-5-carboxamide
N-(Cyclohexylmethyl)-N-methyl-[2,1,3]-benzoxadiazole-5-carboxamide
N-Benzyl-N-methyl-[2,1,3]-benzoxadiazole-5-carboxamide
N-Methyl-N-(tetrahydrofuran-2-ylmethyl)-[2,1,3]-benzoxadiazole-5-carboxamide
N-Methyl-N-pyridin-3-yl-[2,1,3]-benzoxadiazole-5-carboxamide
N-Methyl-N-phenyl-[2,1,3]-benzoxadiazole-5-carboxamide
N-Cyclopropyl-N-tetrahydro-2H-pyran-4-yl-[2,1,3]-benzoxadiazole-5-carboxamide
N-Tetrahydro-2H-pyran-4-yl-N-(2,2,2-trifluoroethyl)-[2,1,3]-benzoxadiazole-5-carboxamide tert-Butyl-4-[([2,1,3]-benzoxadiazol-5-ylcarbonyl)(methyl)amino]piperidine-1-carboxylate
N-Methyl-N-piperidin-4-yl-[2,1,3]-benzoxadiazole-5-carboxamide hydrochloride
N-Methyl-N-(1-methylpiperidin-4-yl)-[2,1,3]-benzoxadiazole-5-carboxamide
N-(1-Acetylpiperidin-4-yl)-N-methyl-[2,1,3]-benzoxadiazole-5-carboxamide
N-(1-Formylpiperidin-4-yl)-N-methyl-[2,1,3]-benzoxadiazole-5-carboxamide
N-Methyl-N-[1-(methylsulfonyl)piperidin-4-yl)-[2,1,3]-benzoxadiazole-5-carboxamide
N-Methyl-N-(tetrahydro-2H-pyran-4-yl)-[2,1,3]-benzothiadiazole-5-carboxamide
N-Methyl-N-(tetrahydro-2H-thiopyran-4-yl)-[2,1,3]-benzoxadiazole-5-carboxamide
N-Methyl-N-(1-oxidotetrahydro-2H-thiopyran-4-yl)-[2,1,3]-benzoxadiazole-5-carboxamide
N-Methyl-N-(1,1-dioxidotetrahydro-2H-thiopyran-4-yl)-[2,1,3]-benzoxadiazole-5-carboxamide
N-Methyl-N-tetrahydro-2H-pyran-4-ylquinoxaline-6-carboxamide
N-Methyl-N-(4-oxocyclohexyl)-[2,1,3]-benzoxadiazole-5-carboxamide
N-[4-(Hydroxyimino)cyclohexyl]-N-methyl-[2,1,3]-benzoxadiazole-5-carboxamide
N-[4-(Methoxyimino)cyclohexyl]-N-methyl-[2,1,3]-benzoxadiazole-5-carboxamide
N-(4,4-Difluorocyclohexyl)-N-methyl-[2,1,3]-benzoxadiazole-5-carboxamide
N-(4-fluorocyclohex-3-en-1-yl)-N-methyl-[2,1,3]-benzoxadiazole-5-carboxamide
N-(4-trans-Hydroxycyclohexyl)-[2,1,3]-benzoxadiazole-5-carboxamide
N-(trans-4-Hydroxy-4-methylcyclohexyl)-[2,1,3]-benzoxadiazole-5-carboxamide
N-(cis-4-Hydroxy-4-methylcyclohexyl)-N-methyl-[2,1,3]-benzoxadiazole-5-carboxamide
N-(trans-4-Hydroxy-4-methylcyclohexyl)-N-methyl-[2,1,3]-benzoxadiazole-5-carboxamide
N-(cis-4-Hydroxy-4-ethylcyclohexyl)-N-methyl-[2,1,3]-benzoxadiazole-5-carboxamide N-(trans-4-Hydroxy-4-ethylcyclohexyl)-N-methyl-[2,1,3]-benzoxadiazole-5-carboxamide
N-(cis-4-Ethynyl-4-hydroxycyclohexyl)-N-methyl-[2,1,3]-benzoxadiazole-5-carboxamide
N-(cis-4-But-3-en-1-yl-4-hydroxycyclohexyl)-N-methyl-[2,1,3]-benzoxadiazole-5-carboxamide
N-(trans-4-But-3-en-1-yl-4-hydroxycyclohexyl)-N-methyl-[2,1,3]-benzoxadiazole-5-carboxamide
N-(4-trans-Hydroxycyclohexyl)-N-methyl-[2,1,3]-benzoxadiazole-5-carboxamide
N-(4-trans-Hydroxycyclohexyl)-N-$D_3$-methyl-[2,1,3]-benzoxadiazole-5-carboxamide
N-(trans-4-Methoxycyclohexyl)-N-methyl-[2,1,3]-benzoxadiazole-5-carboxamide
N-(trans-4-Methoxycyclohexyl)-N-methyl-[2,1,3]-benzoxadiazole-5-carbothioamide
N-(4-cis-Hydroxycyclohexyl)-N-methyl-[2,1,3]-benzoxadiazole-5-carboxamide
N-Methyl-N-[trans-4-(2H-tetrazol-2-yl)cyclohexyl]-[2,1,3]-benzoxadiazole-5-carboxamide
N-(trans-4-Azidocyclohexyl)-N-methyl-[2,1,3]-benzoxadiazole-5-carboxamide
N-(trans-4-Aminocyclohexyl)-N-methyl-[2,1,3]-benzoxadiazole-5-carboxamide
N-(cis-3-Hydroxycyclohexyl)-N-methyl-[2,1,3]-benzoxadiazole-5-carboxamide
N-(trans-3-Hydroxycyclohexyl)-N-methyl-[2,1,3]-benzoxadiazole-5-carboxamide
N-Methyl-N-(3-oxocyclohexyl)-[2,1,3]-benzoxadiazole-5-carboxamide
N-Methyl-N-(3,3-difluorocyclohexyl)-[2,1,3]-benzoxadiazole-5-carboxamide
N-(2-Hydroxycyclohexyl)-N-methyl-[2,1,3]-benzoxadiazole-5-carboxamide
N-Methyl-N-(2-oxocyclohexyl)-[2,1,3]-benzoxadiazole-5-carboxamide
N-Methyl-N-(2,2-difluorocyclohexyl)-[2,1,3]-benzoxadiazole-5-carboxamide
N-(2-Hydroxytetrahydro-2H-pyran-4-yl)-[2,1,3]-benzoxadiazole-5-carboxamide
N-(2-oxotetrahydro-2H-pyran-4-yl)-[2,1,3]-benzoxadiazole-5-carboxamide
N-Methyl-N-(2-oxotetrahydro-2H-pyran-4-yl)-[2,1,3]-benzoxadiazole-5-carboxamide
N-(2-Hydroxytetrahydro-2H-pyran-4-yl)-N-methyl-[2,1,3]-benzoxadiazole-5-carboxamide
trans-4-[(2,1,3-Benzoxadiazol-5-ylcarbonyl)(methyl)amino]cyclohexyl N,N-dimethyl glycinate hydrochloride
trans-4-[(2,1,3-Benzoxadiazol-5-ylcarbonyl)(methyl)amino]cyclohexyl L-alaninate hydrochloride
N—(R)-Tetrahydrofuran-3-yl-[2,1,3]-benzoxadiazole-5-carboxamide
N-Methyl-N—(R)-tetrahydrofuran-3-yl-[2,1,3]-benzoxadiazole-5-carboxamide
trans-4-[(2,1,3-Benzoxadiazol-5-ylcarbonyl)(methyl)amino]cyclohexyl glycinate hydrochloride
N-2-(4-Morpholinyl)ethyl-[2,1,3]-benzoxadiazole-5-carboxamide
N-Methyl-N-2-(4-morpholinyl)ethyl-[2,1,3]-benzoxadiazole-5-carboxamide hydrochloride
N-Methyl-N-tetrahydro-2H-pyran-4-yl-[2,1,3]-benzoxadiazole-5-carbothioamide
trans-4-[(2,1,3-Benzoxadiazol-5-ylcarbonyl)(methyl)amino]cyclohexyl L-valinate hydrochloride
trans-4-[(2,1,3-Benzoxadiazol-5-ylcarbonyl)(methyl)amino]-1-methylcyclohexyl N,N-dimethyl glycinate hydrochloride
N-Methyl-N-tetrahydro-2H-pyran-4-ylmethyl-[2,1,3]-benzoxadiazole-5-carboxamide
trans-4-[(2,1,3-Benzoxadiazol-5-ylcarbonyl)(methyl)amino]-1-methylcyclohexyl glycinate hydrochloride III. Synthesis The synthesis of the compounds of the invention is preferably carried out by the following Scheme. Alternative syntheses by analogy relying on methodology that exists in the art also may be used.

In the Scheme, Steps A and B, used to produce the N-methylamines 4 (A=Me) are carried out using standard conditions, for example, amines 1 are dissolved in a suitable organic solvent, for example dichloromethane, a base (e.g. $NEt_3$ or $NaHCO_3$ in water) is added and then a solution of benzyloxycarbonyl chloride (Cbz-Cl) in an organic solvent e.g. dichloromethane is added, which results in the formation of the benzyl carbamates 2 (step A). The carbamates 2 are then reduced with for example lithium aluminium hydride ($LiAlH_4$) in a suitable organic solvent for example tetrahydrofuran (THF) to give amines 4 (A=Me, Step B). Amines 4, may be alternatively prepared by reductive amination of ketones 3 in the presence of an amine ($ANH_2$), using standard conditions, for example Pd/C in an appropriate solvent for example ethanol, as shown in Step C. Acid chloride 8a is synthesized starting with 4-amino-3-nitrobenzoic acid 5, by firstly oxidizing using sodium hypochlorite in ethanol in the presence of potassium hydroxide to give intermediate 6 (Step D) and then reducing 6 with triethyl phosphite ($P(OEt)_3$) in a suitable solvent, for example ethanol, to give benzofurazan carboxylic acid 7 as shown in Step E. The carboxylic acid 7 was transformed to the acid chloride 8a in Step F by refluxing with thionyl chloride in toluene. The benzofurazan carboxylic acid 7 can be transformed into amides 9a and 10a using amines 1 and 4, respectively, using standard amide coupling conditions for example 1-ethyl-3-(3-dimethylaminopropyl) carbodiimide (EDCI), O-benzotriazole-N,N,N',N'-tetramethyl-uronium-hexafluoro-phosphate (HBTU), N-hydroxybenzotriazole (HOBT), dimethylaminopyridine (DMAP) and triethylamine in a suitable solvent e.g. dichloromethane (Step G). Alternatively, acid chloride 8a can be transformed into amides 9a and 10a using standard coupling conditions with amines 1 and 4, respectively, in the presence of a base for example triethylamine in dichloromethane as solvent or aqueous sodium hydrogen carbonate in water and dichloromethane (Step H). The benzothiadiazole amides 9b and 10b are prepared from the commercially available benzothiadiazole acid chloride 8b using standard coupling conditions with amines 1 and 4, respectively, in the presence of a base for example triethylamine in dicholoromethane as solvent, or aqueous sodium hydrogen carbonate in water and dichloromethane (Step H). The quinoxaline-6-carboxylic acid chloride 8c is prepared by condensation of commercially available 3,4-diaminobenzoic acid with glyoxal followed by refluxing with thionyl chloride and a catalytic amount of DMF in toluene using standard procedures. 8c was converted to the amides 9c and 10c by coupling reaction with amines 1and 4 using the standard procedures described previously (Step H). Alternatively, amides 10a-c can be prepared from amides 9a-c by deprotonation with a suitable base for example sodium hydride in a solvent e.g. N,N-dimethylformamide (DMF) followed by treatment with an alkylating agent (RX) to yield 10a-c (Step I). The thioamides 11 can be prepared from amides 10 using standard procedures, for example, by reacting 10 with phosphorous pentoxide in a suitable solvent e.g. toluene (Step J).

IV. Method of Treatment

According to one aspect of the invention, a method is provided for treating a mammalian subject suffering from a hypoglutamatergic condition, or from deficiencies in the number or strength of excitatory synapses or in the number of AMPA receptors. In such a subject, memory or other cognitive functions may be impaired, or cortical/striatal imbalance may occur, leading to loss of memory, dementia, depression, attention disorders, sexual dysfunction, movement disorders, schizophrenia or schizophreniform behavior. Memory disorders and learning disorders, which are treatable according to the present invention include those disorders that result from, for example, aging, trauma, stroke and neurodegenerative disorders. Examples of neurodegenerative disorders include, but are not limited to, those associated with drug-induced states, neurotoxic agents, Alzheimer's disease, and aging. These conditions are readily recognized and diagnosed by those of ordinary skill in the art and treated by administering to the patient an effective amount of one or more compounds according to the present invention.

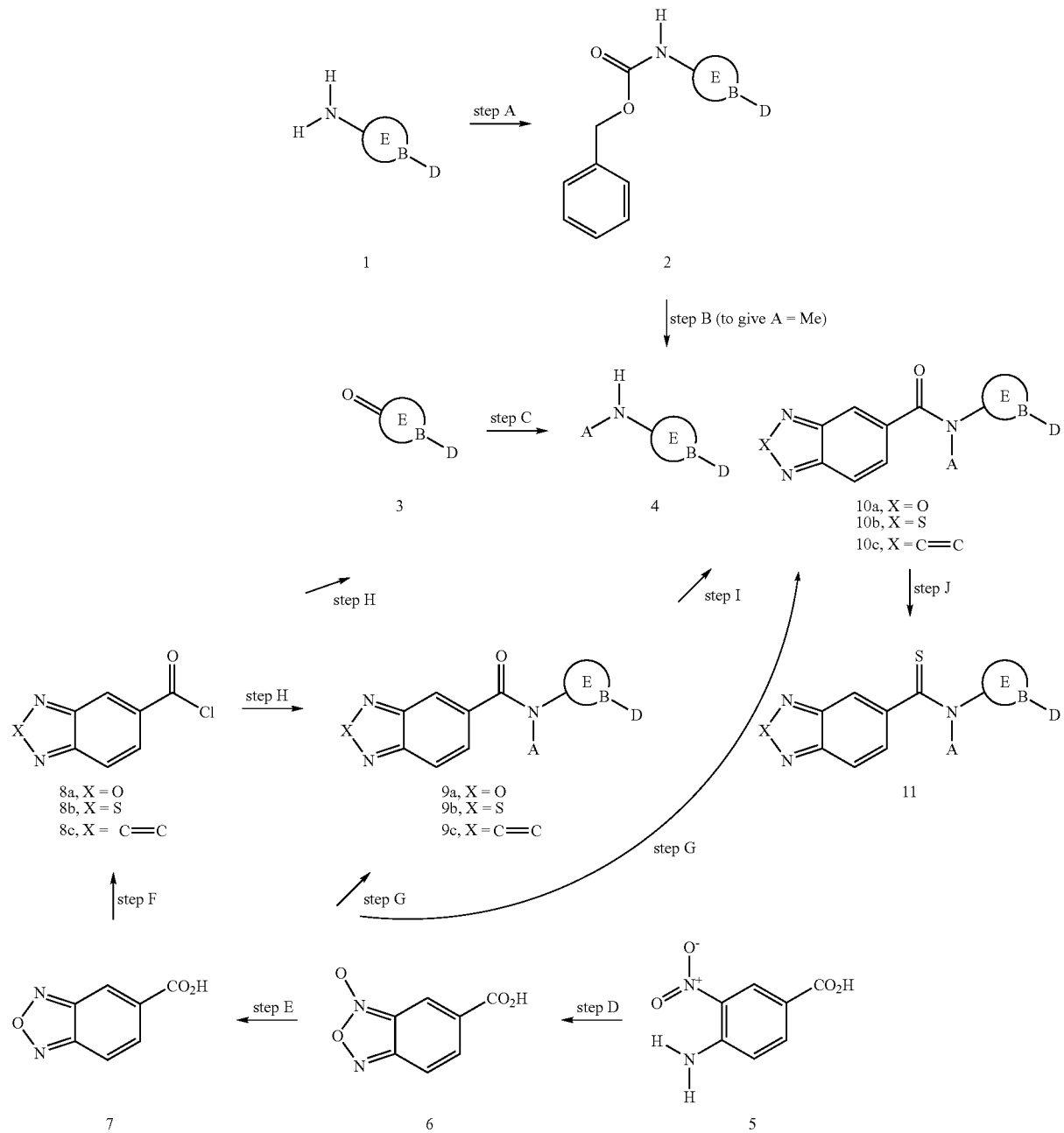

In another aspect, the invention provides a method for reducing or inhibiting respiratory depression in a subject having such a condition, comprising administering to the subject an amount of a compound of the invention, the amount being sufficient to reduce or inhibit respiratory depression. In a further aspect of the invention, a method is provided for reducing or inhibiting respiratory depression comprising administering to the subject an amount of a compound of the invention in combination with an opiate; examples of such opiates include but are not limited to, alfentanil and fentanyl.

In a further aspect, the invention provides a method for reducing or inhibiting breathing-related sleep disorders or sleep apnea in a subject having sleep apnea, comprising administering to the subject an amount of a compound of the invention, the amount being sufficient to reduce or inhibit the breathing related sleep disorder.

In the present invention, the method of treatment comprises administering to the subject in need of treatment, in a pharmaceutically acceptable carrier, an effective amount of a compound having the Formula I below:

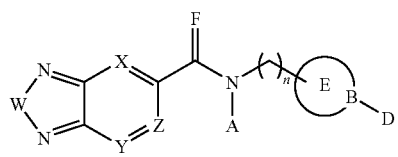

I wherein:
W is oxygen, sulfur or CH═CH;
X, Y and Z are independently selected from the group consisting of —N, or —CR, wherein:
R is H, —Br, —Cl, —F, —CN, —$NO_2$, —$OR^1$, —$NR^1_2$, —$C_1$-$C_6$ branched or un-branched alkyl, which may be un-substituted or substituted,
wherein:
$R^1$ is H, —$C_1$-$C_6$ branched or un-branched alkyl which, may be un-substituted or substituted, F═O or S
A is H, or —$C_1$-$C_6$ branched or un-branched alkyl, which may be un-substituted or substituted, —$C_2$-$C_6$ branched or un-branched alkenyl, which may be un-substituted or substituted, —$C_2$-$C_6$ branched or un-branched alkynyl, which may be un-substituted or substituted, —$C_3$-$C_7$ cycloalkyl which may be un-substituted or substituted, —$C_3$-$C_7$ alkylcycloalkyl which may be un-substituted or substituted, aryl or heterocycle which may be un-substituted or substituted, alkylaryl which may be un-substituted or substituted, alkylheterocycle which may be un-substituted or substituted
n=0, 1, 2, 3, 4, 5, or 6;

is a —$C_3$-$C_7$ cycloalkyl, which may be un-substituted or substituted, a —$C_4$-$C_7$ azacycloalkyl, which may be un-substituted or substituted, a $C_7$-$C_{10}$ bicycloalkyl which may be un-substituted or substituted, a —$C_7$-$C_{10}$ azabicycloalkyl, which may be un-substituted or substituted, aryl which may be un-substituted or substituted or a heterocycle which may be un-substituted or substituted;
B is —C═, C—$R^a$, O, N, S, C═O, S═O or $SO_2$,
$R^a$ is H, a halogen (preferably F), OH, O-alkyl, cyano, or a —$C_1$-$C_6$ alkyl group which is un-substituted or substituted and which optionally, forms a $C_3$-$C_7$ cycloalkyl group with D; and D is absent when B is O, S, C═O, S═O or $SO_2$, or if present, is bonded to B when B is —C═, C—$R^a$ or N, and is H, a halogen (preferably F), $OR^b$, a —$C_1$-$C_6$ branched or un-branched alkyl, which may be un-substituted or substituted, and which optionally, forms a $C_3$-$C_7$ cycloalkyl group with $R^a$, a —$C_2$-$C_6$ branched or un-branched alkenyl, which may be un-substituted or substituted, a —$C_2$-$C_6$ branched or un-branched alkynyl, which may be un-substituted or substituted, a —$C_3$-$C_7$ cycloalkyl which may be un-substituted or substituted, an aryl which may be un-substituted or substituted, a heterocycle which may be un-substituted or substituted, a —$C_2$-$C_7$ carboxyalkyl which may be un-substituted or substituted, a carboxyaryl which may be un-substituted or substituted, a carboxyheteroaryl which may be un-substituted or substituted, a —$C_1$-$C_7$ sulfonylalkyl which may be un-substituted or substituted, a sulfonylaryl which may be un-substituted or substituted or a sulfonylheteroaryl which may be un-substituted or substituted, or when B is —C—$R^a$, $R^a$ and D optionally form a ═N—$R^c$ or a ═N—$OR^c$ group with B, wherein $R^c$ is H or an unsubstituted or substituted $C_1$-$C_7$ alkyl group; and
$R^b$ is H, a —$C_1$-$C_7$ alkyl group which may be branched or un-branched, un-substituted or substituted or a —$C_2$-$C_7$ acyl group which may be un-substituted or substituted;
or a pharmaceutically acceptable salt, solvate, pro-drug or polymorph thereof, optionally in combination with a pharmaceutically acceptable carrier, additive or excipient.

In the present invention, the method of treatment comprises administering to the subject in need of treatment, in a pharmaceutically acceptable carrier, an effective amount of a compound having the Formulas II-IX as previously defined.

Compounds according to the present invention exhibit enhanced bioavailability in most instances due, at least in part, to enhanced pharmacokinetics exhibited by the present compounds. Accordingly, the present compounds may be favorably formulated into pharmaceutical compositions in a variety of dosage forms, and in particular, oral dosage forms.

As noted above, treatment of a subject according to the method of the invention is useful for enhancing AMPA receptor activity, and thus may be used to facilitate the learning of behaviors dependent upon AMPA receptors, and to treat conditions, such as memory impairment, in which AMPA receptors, or synapses utilizing these receptors, are reduced in numbers or efficiency. The method is also useful for enhancing excitatory synaptic activity in order to restore an imbalance between brain sub-regions, which may manifest itself in schizophrenia or schizophreniform behavior, or other behavior as described above. The compounds administered in accordance with the method have been found to be more effective than previously described compounds in enhancing AMPA receptor activity, as shown in the in vivo tests described below.

V. Biological Activity

A. Enhancement of AMPA Receptor Function In Vivo

Synaptic responses mediated by AMPA receptors are increased according to the method of the invention, using the compounds described herein.

The electrophysiological effects of the invention compounds were tested in vivo in anesthetized animals according to the following procedures. Animals are maintained under anesthesia by phenobarbital administered using a Hamilton syringe pump. Stimulating and recording electrodes are inserted into the perforant path and dentate gyrus of the hippocampus, respectively. Once electrodes are implanted, a stable baseline of evoked responses are elicited using single monophasic pulses (100 μs pulse duration) delivered at 3/min to the stimulating electrode. Field EPSPs are monitored until a stable baseline is achieved (about 20-30 min), after which a solution of test compound is injected intraperitoneally and evoked field potentials are recorded. Evoked potentials were recorded for approximately 2 h following drug administration or until the amplitude of the field EPSP returns to baseline. In the latter instance, it is common that an iv administration is also carried out with an appropriate dose of the same test compound. Invention compounds were assayed in the in vivo electrophysiology assay described above and data for representative test compounds is shown in column 1 in Table 1. Compounds of the invention are significantly more active in increasing the amplitude of the field EPSP in the rat dentate gyrus following i.p. dosing than CX516 (1-(quinoxalin-6-ylcarbonyl)piperidine; U.S. Pat. No. 5,773,434, US2002/0055508) which gave a 9% increase in amplitude of the field EPSP at 50 mg/kg i.p.

TABLE 1

| Compound Example Number | [1]In vivo Electrophysiology | [2]Inhibition of d-Amphetamine Stimulated Locomotion |
|---|---|---|
| 4 | 17% | 80% |
| 5 | 15% | NT |
| 6 | 10% | 37% |
| 11 | 12% | NT |
| 12 | 20% | 66% |
| 17 | 12% | 23% |
| 25 | 10%[3] | NT |
| 33 | 16%[3] | NT |
| 36 | 5%[3] | NT |
| 37 | 18% | 100% |
| 40 | 18% | 84% |
| 41 | 18% | 67% |
| 45 | 19% | 122% |
| 51 | 21% | 100% |
| 53 | 17% | 94% |
| 54 | 18%[3] | NT |
| 56 | 19% | NT |
| 73 | 13% | NT |

[1]% increase in the amplitude of the field EPSP in the dentate gyrus of rat @ 10 mpk i.p.
[2]% Inhibition of d-amphetamine stimulated locomotion in mice @ 18 mpk i.p.
[3]Dosed intravenously.
NT = Not tested B. Behavioral Testing: Inhibition of d-Amphetamine Stimulated Locomotion The ability of the invention compounds to inhibit d-Amphetamine stimulated locomotor activity was assayed according to the following procedure. Male CD1 mice, 25-30 gm body weight, were brought into the experimental room and allowed at least 30 min of acclimation. Each mouse was placed into the testing enclosure with an infrared beam array that automatically monitors the animal's activity. Mice were habituated in the testing enclosure for to 20 min, and then returned to their home cage. Mice were dosed intraperitoneally with test compound in appropriate vehicle 5 minutes before d-Amphetamine injection (2 mpk). Ten minutes after d-Amphetamine injection, mice were tested for locomotor activity for a total of 15 minutes. The data was computer collected and expressed as "arbitrary movement units." All data were analyzed by comparing the groups treated with the test compound to the vehicle control group. The data for test compounds is shown in Table 1, column 2. The data shown is the % inhibition of hyperactivity induced by acute administration of 2 mg/kg d-amphetamine in mice. The compounds tested produced a statistically significant inhibition of d-amphetamine stimulated locomotion.

VI. Administration, Dosages, and Formulation

As noted above, the compounds and method of the invention increase glutamatergic synaptic responses mediated by AMPA receptors, and are useful for the treatment of hypoglutamatergic conditions. They are also useful for treatment of conditions such as impairment of memory or other cognitive functions, brought on by a deficiency in the number or strength of excitatory synapses, or in the number of AMPA receptors. They may also be used in the treatment of schizophrenia or schizophreniform behavior resulting from a cortical/striatal imbalance, and in facilitation of learning of behaviors dependent upon AMPA receptors.

In subjects treated with the present compounds, pharmaceutical compositions and methods memory or other cognitive functions may be impaired or cortical/striatal imbalance may occur, leading to loss of memory, dementia, depression, attention disorders, sexual dysfunction, movement disorders, schizophrenia or schizophreniform behavior. Memory disorders and learning disorders, which are treatable according to the present invention, include those disorders that result from aging, trauma, stroke and neurodegenerative disorders. Examples of neurodegenerative disorders include, but are not limited to, those associated with drug-induced states, neurotoxic agents, Alzheimer's disease, and aging. These conditions are readily recognized and diagnosed by those of ordinary skill in the art and treated by administering to the patient an effective amount of one or more compounds according to the present invention.

Generally, dosages and routes of administration of the compound will be determined according to the size and condition of the subject, according to standard pharmaceutical practices. Dose levels employed can vary widely, and can readily be determined by those of skill in the art. Typically, amounts in the milligram up to gram quantities are employed. The composition may be administered to a subject by various routes, e.g. orally, transdermally, perineurally or parenterally, that is, by intravenous, subcutaneous, intraperitoneal, or intramuscular injection, among others, including buccal, rectal and transdermal administration. Subjects contemplated for treatment according to the method of the invention are animals, especially mammals, including humans, companion animals, domesticated animals, laboratory animals, and the like.

Formulations containing the compounds according to the present invention may take the form of solid, semi-solid, lyophilized powder, or liquid dosage forms, such as, for example, tablets, capsules, powders, sustained-release formulations, solutions, suspensions, emulsions, suppositories, creams, ointments, lotions, aerosols, patches or the like, preferably in unit dosage forms suitable for simple administration of precise dosages.

Pharmaceutical compositions according to the present invention comprise an effective amount of one or more compounds according to the present invention and typically include a conventional pharmaceutical carrier or excipient and may additionally include other medicinal agents, carriers, adjuvants, additives and the like. Preferably, the composition will be about 0.5 to 75% by weight or more of a compound or compounds of the invention, with the remainder consisting essentially of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

Liquid compositions can be prepared by dissolving or dispersing the compounds (about 0.5% to about 20% by weight or more), and optional pharmaceutical adjuvants, in a carrier, such as, for example, aqueous saline, aqueous dextrose, glycerol, or ethanol, to form a solution or suspension. For use in oral liquid preparation, the composition may be prepared as a solution, suspension, emulsion, or syrup, being supplied either in liquid form or a dried form suitable for hydration in water or normal saline.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations.

An injectable composition for parenteral administration will typically contain the compound in a suitable i.v. solution, such as sterile physiological salt solution. The composition may also be formulated as a suspension in a lipid or phospholipid, in a liposomal suspension, or in an aqueous emulsion.

Methods for preparing such dosage forms are known or will be apparent to those skilled in the art; for example, see *Remington's Pharmaceutical Sciences* (17th Ed., Mack Pub. Co., 1985). The composition to be administered will contain a quantity of the selected compound in a pharmaceutically effective amount for effecting increased AMPA receptor currents in a subject.

The following examples illustrate but are not intended in any way to limit the invention.

Unless otherwise stated, all temperatures are given in degrees Celsius. Unless otherwise stated, all NMR spectra are $^1$H NMR spectra and were obtained in deuterochloroform or deuterated DMSO as solvent using tetramethylsilane as an internal standard. All names of Example compounds conform to IUPAC nomenclature as provided by the computer software ChemSketch by ACD Labs.

I. Chemical Methods

Intermediate 1

[2,1,3]-Benzoxadiazole-5-carboxylic acid

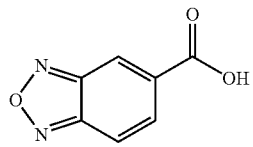

In a 3 L reactor fitted with mechanical stirring, reflux condenser, thermometer and nitrogen inlet, KOH (72.46 g) was dissolved in ethanol (250 ml) and water (250 ml). 4-Amino-3-nitrobenzoic acid (100 g) was added and the orange suspension was heated to 65-70° C. within 30 minutes. The resulting suspension was stirred at the same temperature for 45 minutes and cooled to 0° C.±5° C. within 30 minutes. A commercially available (13% w/w) solution of sodium hypochlorite (448.93 g) was added drop wise within 1.5 hours at 0° C.±5° C. The reaction mixture was stirred at the same temperature for 2 hours and controlled by TLC (CHCl$_3$ 100/acetone 2/acetic acid 1). Water (350 ml) was added within 15 minutes at 0° C. ±5° C. to give a fine yellow suspension. The reaction mixture was then acidified with a 6N HCl solution (239 ml) until 0.5<pH<1 was reached. Sodium chloride (58.44 g) was added and the resulting suspension was stirred at 0° C.±5° C. for 1.5 hours under nitrogen. The solid was collected by filtration, washed with 3×400 ml water and dried (40° C., 30 mbars, 12 hours) to yield 83.6 g (88.8% yield) of [2,1,3]-benzoxadiazole-5-carboxylic acid N-oxide.

In a 2 L reactor fitted with mechanical stirring, thermometer, addition funnel, reflux condenser and nitrogen inlet, [2,1,3]-benzoxadiazole-5-carboxylic acid N-oxide (80 g) was dissolved in absolute ethanol (800 ml). To this solution triethyl phosphite (114.05 g) was added within 10 minutes at 70° C.±2° C. The resulting mixture was heated to reflux (76-78° C.) and maintained for 2 hours. Monitoring the reaction by TLC(CHCl$_3$ 100/acetone 2/acetic acid 1) showed complete reaction. The solvent was removed under vacuum (30 mbars, 40° C.) which yielded a black oil (180 g). Water (400 ml) was added and the mixture was extracted with ethyl acetate (400 and 160 ml). The organic phase was extracted with 850 ml water containing NaOH (9.5<pH<10). The aqueous phase was separated and extracted with ethyl acetate (3×240 ml). The aqueous phase was acidified (78 ml 6 N HCl) to 1<pH<2 at 5° C.±2° C. which resulted in the crystallization of the yellow product, which was filtered off and dried (40° C., 30 mbars, 12 hours) to yield 65.56 g (90% yield) [2,1,3]-benzoxadiazole-5-carboxylic acid: mp=160-161° C., $^1$H NMR (300 MHz, DMSO) δ 13.8 (s, 1H); 8.57 (s, 1H); 8.56 (d, 1H, J=0.6 Hz); 7.87 ppm (d, 1H, J=0.6 Hz).

Intermediate 2

[2,1,3]-Benzoxadiazole-5-carbonylchloride

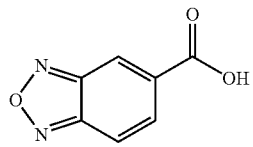

In a 500 ml reactor fitted with mechanical stirring, thermometer, addition funnel, reflux is condenser and nitrogen inlet, [2,1,3]-benzoxadiazole-5-carboxylic acid (28 g) was suspended in toluene (245 ml). To this suspension was added thionyl chloride (39.4 g) and DMF (0.35 ml). The resulting mixture was heated to reflux and maintained for 3 hours. A short pass column was installed and toluene was distilled (atmospheric pressure, 124 ml) off to remove excess reagent. After cooling the remaining toluene was distilled off, which resulted in a thick oil. This oil was distilled (90° C., 2 mm Hg) to remove impurities and the product crystallized on standing (79.8% yield), mp: 55-58° C.

EXAMPLE 1

N-Cycloheptyl-N-methyl-[2,1,3]-benzoxadiazole-5-carboxamide

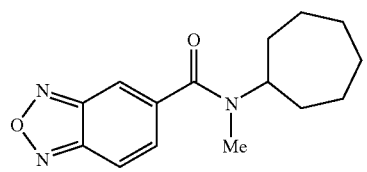

To a solution of cycloheptanone (1.12 g, 10 mmol) in 40 ml of ethanol was added a methylamine (2.5 ml of a 33% solution in ethanol) and 220 mg of Pd on C (10%) were added, and the mixture hydrogenated at 50 psi over night. The solids were filtered off and the mixture concentrated under vacuum to give a pale yellow oil. This material and 1.2 ml of triethylamine were dissolved in 10 ml of dichloromethane and a solution of [2,1,3]-benzoxadiazole-5-carbonylchloride (730 mg, 4 mmol) was added slowly. After stirring the mixture for 2 hours, the organic phase was washed with 1N HCl and conc. NaHCO$_3$ solution, dried over magnesium sulfate, and then concentrated under vacuum to give a white solid, after trituration with ether (405 mg, 37%). Mp: 80-81° C., $^1$H NMR (300 MHz, CDCl$_3$, rotamers) δ 7.93 (m, 1H); 7.80 (s, 1H); 7.43-7.37 (m, 1H); 4.75-4.60 and 3.70-3.55 (m+m, 1H); 3.01 and 2.87 (s+s, 3H); 2.00-1.20 ppm (m, 12H).

EXAMPLE 2

N-(4,4-Dimethylcyclohexyl-N-methyl-[2,1,3]-benzoxadiazole-5-carboxamide

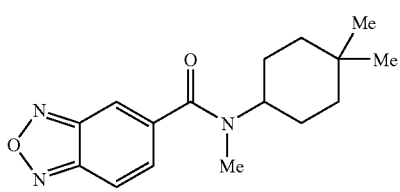

Methylamine, generated by heating a mixture of methylamine hydrochloride (10 g) and is sodium hydroxide pellets (18 g), was condensed (dry ice trap) into a solution of 4,4-dimethylcyclohexanone (1.0 g, 7.9 mmol) in 40 ml of methanol and 20 ml of THF. 10% Pd on C (400 mg) was added and the mix was hydrogenated at room temperature over night. The solids were filtered off, and the mixture concentrated under vacuum. This material and triethylamine (2 ml) were dissolved in chloroform (50 ml) and a solution of [2,1,3]-benzoxadiazole-5-carbonylchloride (900 mg, 4.9 mmol), in chloroform (40 ml), was added slowly at room temperature. After stirring the mixture for 1 hour, the organic phase was washed with 1N HCl and conc. NaHCO$_3$ solution, dried over sodium sulfate, and concentrated under vacuum to yield an oil, which was purified using silica gel chromatography eluting with chloroform/ethyl acetate/hexane (10:20:70), to give a white solid, after crystallization from methyl-t-butyl ether (MTBE)/hexane (38 mg). Mp=143-5° C., $^1$H NMR (300 MHz, CDCl$_3$, rotamers) δ 7.91 (d, 1H, J=8.7 Hz); 7.81 (sb, 1H); 7.45-7.36 (m, 1H); 4.52-4.35 and 3.45-3.30 (m+m, 1H); 3.04 and 2.89 (s+s, 3H) and 1.95-0.80 ppm (m, 14H).

EXAMPLE 3

N-Methyl-N-spiro[2.5]oct-6-yl-[2,1,3]-benzoxadiazole-5-carboxamide

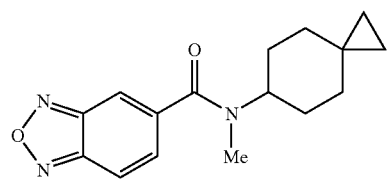

A solution of benzyl spiro[2.5]oct-6-yl carbamate (1.1 g, 3.85 mmol) in THF (40 ml) was slowly added to LiAlH$_4$ (1.0 g) in THF (40 ml), at room temperature, and the mixture stirred for 2 hours. The mixture was then cooled with ice/water and hexane (35 ml) was added, followed by careful addition of a solution of sodium hydroxide (1 g) in water (4 ml). Celite was added, the mixture was filtered and the filtrate concentrated under vacuum. A solution of triethylamine (2 ml) in chloroform (60 ml) was added to the residue followed by a solution of [2,1,3]-benzoxadiazole-5-carbonylchloride (704 mg, 6 mmol), in chloroform (10 ml). After stirring the mixture for 1 hour, the organic phase was washed with 1N sulfuric acid and conc. NaHCO$_3$ solution, the aqueous phases were re-extracted with chloroform (100 ml), and the combined organic phases were dried over magnesium sulfate, concentrated under vacuum and chromatographed on silica gel eluting with ethyl acetate/hexane (30:70) to give a white solid (410 mg, 37% yield), after crystallization from dichloromethane/MTBE: Mp=107-109° C., $^1$H NMR (300 MHz, CDCl$_3$, rotamers) δ 7.91 (d, 1H, J=9.3 Hz); 7.82 (s, 1H); 7.47-7.35 (m, 1H); 4.66-4.50 and 3.55-3.40 (m+m, 1H); 3.05 and 2.91 (s+s, 3H); 2.10-1.55 and 0.99-0.86 (m, 8H) and 0.40-0.20 ppm (m, 4H).

EXAMPLE 4

N-Cyclohexyl-N-methyl-[2,1,3]-benzoxadiazole-5-carboxamide

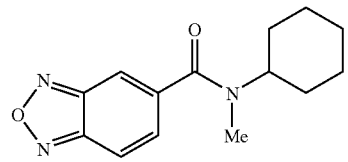

To a solution of cyclohexylamine (4 ml, 17.4 mmol) and triethylamine (3 ml) in 50 ml of dichloromethane was slowly added benzylchloroformate (2.4 ml, 17.4 mmol) and the mixture stirred at room temperature overnight. The solution was extracted with 1N HCl and conc. NaHCO$_3$ solution, the organic phase dried over magnesium sulfate, and concentrated under vacuum to yield 2.85 g of white solid. The solid was dissolved in THF (50 ml), slowly added to LiAlH$_4$ (1.09 g) in diethyl ether (50 ml) and the mixture heated to 70° C. for 1 hour. The mixture was then cooled with an ice/water bath, hexane (40 ml) was added, followed by careful addition of a solution of sodium hydroxide (5 g) in 10 ml of water. Celite was added and the mixture was filtered, followed by concentration under vacuum. To a solution of the resulting residue in triethylamine (3 ml) and dichloromethane (50 ml) was slowly added [2,1,3]-benzoxadiazole-5-carbonylchloride (1.095 g, 6 mmol). After stirring the mixture for 1 hour, the organic phase was washed with 1N HCl and conc. NaHCO$_3$ solution, dried over magnesium sulfate, and concentrated under vacuum to give a white solid (1.45 g). The material was chromatographed on a silica gel eluting with chloroform/ethyl acetate (4:1) to to give a white solid (406 mg, 26% yield). Mp=134-5° C., LC-MS, MH$^+$=260; $^1$H NMR (300 MHz, CDCl$_3$, 2 rotamers) δ 7.91 (d, 1H, J=9.3 Hz); 7.81 (s, 1H); 7.45-7.36 (m, 1H); 4.6-4.45 and 3.5-3.3 (m+m, 3H); 3.01 and 2.87 (s+s, 1H); 1.95-1.00 ppm (m, 10H).

EXAMPLE 5

N-Cyclopentyl-N-methyl-[2,1,3]-benzoxadiazole-5-carboxamide

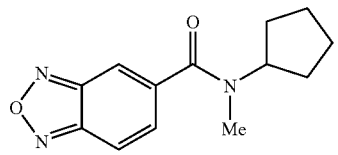

The title compound was prepared from cyclopentanone and [2,1,3]-benzoxadiazole-5-carbonylchloride using the procedures described for Example 2. Mp=110-111° C., LC-MS, MH$^+$=246; $^1$H NMR (300 MHz, CDCl$_3$, 2 rotamers) δ 7.91 (d, 1H, J=9.3 Hz); 7.83 (s, 1H); 7.42 (d, 1H, J=9.3 Hz); 5.1-4.9 and 4.15-3.95 (m+m, 1H); 2.995 (s, 3H); 2.1-1.40 ppm (m, 8H).

EXAMPLE 6

N-Cyclobutyl-N-methyl-[2,1,3]-benzoxadiazole-5-carboxamide

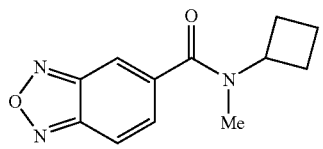

The title compound was prepared from cyclobutylamine hydrochloride and [2,1,3]-benzoxadiazole-5-carbonylchloride according to the procedures described for Example 4. Mp=51-2° C., LC-MS, MH$^+$=232; $^1$H NMR (300 MHz, CDCl$_3$, 2 rotamers) δ 7.91 (d, 1H, J=9.0 Hz); 7.81 (s, 1H); 7.42 (d, 1H, J=9.0 Hz); 5.1-4.9 and 4.35-4.15 (m+m, 1H); 3.110 (s, 3H); 2.40-1.40 ppm (m, 6H).

EXAMPLE 7

N-Cyclohexyl-[2,1,3]-benzoxadiazole-5-carboxamide

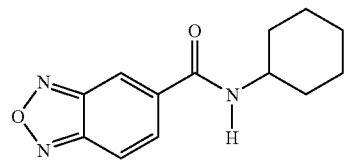

To a solution of cyclohexylamine (1 ml) and triethylamine (1.7 ml) in dichloromethane (20 ml) was added a solution of [2,1,3]-benzoxadiazole-5-carbonylchloride (730 mg, 4 mmol) in dichloromethane (10 ml). After stirring the mixture for 1 hour, the organic phase was washed with 1N HCl and conc. NaHCO$_3$ solution, dried over magnesium sulfate, and concentrated under vacuum. The residue was triturated with ether to give a white solid (265 mg, yield=27%). Mp=172-173° C., $^1$H NMR (300 MHz, CDCl$_3$) δ 8.15 (s, 1H), 7.90 (d, 1H, J=9.0 Hz); 7.82 (d, J=9.0 Hz, 1H); 6.09 ("s", NH, 1H), 4.05-3.97 (m, 1H) and 2.09-1.18 ppm (m, 10H).

EXAMPLE 8

N-Cyclopentyl-[2,1,3]-benzoxadiazole-5-carboxamide

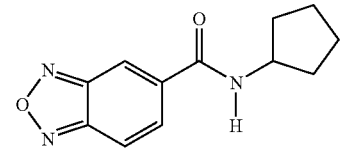

This compound was prepared from cyclopentylamine using the procedure described for Example 7. Mp: 169-170° C., $^1$H NMR (300 MHz, CDCl$_3$) δ 8.17-8.14 (m, 1H), 7.90 (dd, 1H, J=9.0 and 0.6 Hz); 7.81 (dd, J=9.0 and 0.9 Hz, 1H); 6.25 ("s", NH, 1H), 4.50-4.35 (m, 1H) and 2.16-1.45 ppm (m, 8H).

EXAMPLE 9

N-Cyclobutyl-[2,1,3]-benzoxadiazole-5-carboxamide

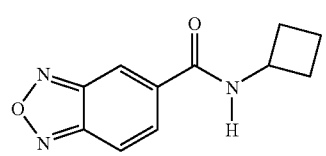

The title compound was prepared from cyclobutylamine using the procedure described for Example 7. Mp: 175-176° C., $^1$H NMR (300 MHz, CDCl$_3$) δ 8.20-8.17 (m, 1H), 7.90

(dd, J=9.0 and 0.9 Hz, 1H); 7.82 (dd, J=9.0 and 0.9 Hz, 1H); 6.46 ("s", NH, 1H), 4.70-4.50 (m, 1H) and 2.50-1.60 ppm (m, 6H).

EXAMPLE 10 and EXAMPLE 11

N-(cis-4-Cyanocyclohexyl)-N-methyl-[2,1,3]-benzoxadiazole-5-carboxamide and N-(trans-4-cyanocyclohexyl)-N-methyl-[2,1,3]-benzoxadiazole-5-carboxamide

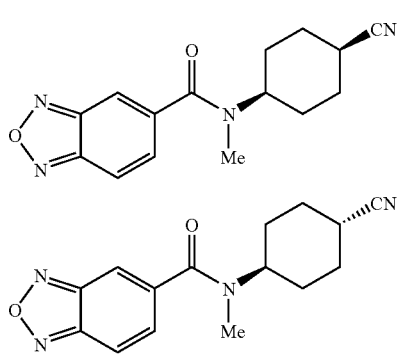

t-Butyl methyl-(4-oxocyclohexyl)carbamate (4.54 g, 20 mmol) and toluenesulphonylmethyl isocyanide (5.07 g, 26 mmol) were dissolved in dry tetrahydrofuran (100 ml) and cooled to 0° C. Potassium tert-butoxide (5.16 g, 46 mmol) was added slowly and the mixture was allowed to warm to 20° C. and stir for 3 hours. The reaction mixture was evaporated to dryness and partitioned between ethyl acetate (150 ml) and water (50 ml). The organic layer was separated, dried over magnesium sulfate and evaporated. The crude product was chromatographed on a silica gel eluting with ethyl acetate/hexane (66:34) to give 1.43 g of tert-butyl methyl-(4-cyanocyclohexyl)carbamate.

t-Butyl methyl-(4-cyanocyclohexyl)carbamate (710 mg, 3 mmol) was dissolved in dichloromethane (20 ml) and trifluoroacetic acid (3 ml) was added. The solvent was evaporated after 2 hours, the residue was re-dissolved in a 4N HCl (3 ml) solution in dioxane and the solvent evaporated. Dichloromethane (30 ml) and NEt$_3$ (2 ml) were added to the residue followed by a solution of [2,1,3]-benzoxadiazole-5-carbonylchloride (548 mg, 3 mmol) in dichloromethane (10 ml). After stirring the mixture for 1 hour at room temperature, the organic phase was washed with 1N HCl and conc. NaHCO$_3$ solution, dried over magnesium sulfate, and concentrated under vacuum. The material was purified on a silica gel column eluting with ethyl acetate/chloroform (1:1) to give 170 mg of N-(cis-4-cyanocyclohexyl)-N-methyl-[2,1,3]-benzoxadiazole-5-carboxamide as a white solid and as the less polar isomer. Mp=222-223° C., $^1$H NMR (300 MHz, CDCl$_3$, rotamers) δ 7.93 (d, 1H, J=9.0 Hz); 7.85 (s, 1H), 7.42 (d, J=9.0 Hz, 1H); 4.65-4.50 and 3.55-3.40 and 3.15-2.80 (m, 5H) and 2.20-1.30 ppm (m, 8H).

The more polar N-(trans-4-cyanocyclohexyl)-N-methyl-[2,1,3]-benzoxadiazole-5-carboxamide was obtained as a white solid after crystallization from diethyl ether (180 mg). Mp=180-181° C., $^1$H NMR (300 MHz, CDCl$_3$, rotamers) δ 7.93 (d, 1H, J=8.7 Hz); 7.83 (s, 1H), 7.42 (d, J=8.7 Hz, 1H); 4.60-4.45 and 3.60-3.40 and 3.05-2.80 (m, 5H) and 2.50-1.40 ppm (m, 8H).

EXAMPLE 12

N-Methyl-N-tetrahydro-2H-pyran-4-yl-[2,1,3]-benzoxadiazole-5-carboxamide

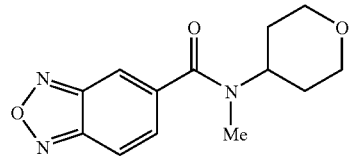

Methylamine, generated by heating a mixture of methylamine hydrochloride (10 g) and sodium hydroxide pellets (18 g), was condensed (dry ice trap) into a solution of tetrahydro-4H-pyran-4-one (1.0 g, 10 mmol) in methanol (50 ml). 10% Pd on C (350 mg) was added and the mixture was hydrogenated at room temperature for 7 hours. The solids were filtered off and the filtrate concentrated under vacuum. The residue was dissolved in chloroform (70 ml) and triethylamine (2 ml) and a solution of [2,1,3]-benzoxadiazole-5-carbonylchloride (500 mg, 2.73 mmol) in chloroform (10 ml) was added slowly. After stirring the reaction mixture for 30 minutes, the organic phase was extracted with 100 ml of water and sulfuric acid (→pH 2) and the aqueous phase re-extracted with chloroform (100 ml), dried over magnesium sulfate, and concentrated under vacuum to give an oil. The crude product was purified by silica gel chromatography eluting ethyl acetate/hexane (75:25) and chloroform/acetone (85:15) to give the title product as a white solid after crystallization from ethyl acetate. Mp=160-2° C., LC-MS, MH$^+$=262; $^1$H NMR (300 MHz, CDCl$_3$, 2 rotamers) δ 7.93 (d, 1H, J=9.0 Hz); 7.84 (s, 1H); 7.42 (d, 1H, J=9.0 Hz); 4.90-4.70 and 4.20-3.10 (m+m, 5H); 2.927 (s, 3H); 2.1-1.5 ppm (m, 4H).

EXAMPLE 13

N-D$_3$-Methyl-N-tetrahydro-2H-pyran-4-yl-[2,1,3]-benzoxadiazole-5-carboxamide

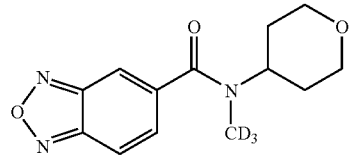

The compound was prepared according to the procedure for Example 12 from D$_3$-methylamine and tetrahydro-4H-pyran-4-one. Mp=165-166° C., $^1$H NMR (300 MHz, CDCl$_3$, 2 rotamers) δ 7.93 (d, 1H, J=9.0 Hz); 7.84 (s, 1H); 7.42 (d, 1H, J=9.0 Hz); 4.90-4.70 and 4.20-3.10 (m+m, 5H) and 2.1-1.5 ppm (m, 4H).

EXAMPLE 14

N-(Tetrahydro-2H-pyran-4-0)-[2,1,3]-benzoxadiazole-5-carboxamide

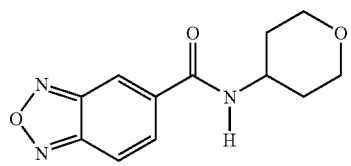

A mixture of hydroxylamine hydrochloride (5.56 g), sodium acetate (6.56 g) and tetrahydro-4H-pyran-4-one (4 g, 40 mmol) in ethanol (100 ml) was refluxed over night. The solids were filtered off and the solvent evaporated. The remaining material was suspended in 100 ml of dry THF and decanted. LiAlH$_4$ (6.07 g) was slowly added and the mixture was refluxed for 1 hour. The cooled mixture was quenched with 10% sodium hydroxide solution, celite was added, and the solids were filtered off. The solvent was evaporated and the residue re-dissolved in dichloromethane (10 ml) and triethylamine (1 ml). This mixture was slowly added to a solution of [2,1,3]-benzoxadiazole-5-carbonylchloride (365 mg, 2.0 mmol) in dichloromethane (10 ml) and stirred at room temperature for 0.5 h. The mixture was washed with 1N HCl (100 ml) and NaHCO$_3$ (100 ml) solution and the aqueous re-extracted with dichloromethane (100 ml). The combined organics were dried over magnesium sulfate, and concentrated under vacuum to give a white solid (410 mg). Mp=204-205° C., $^1$H NMR (300 MHz, CDCl$_3$) δ 8.20-8.18 (m, 1H), 7.92 (dd, 1H, J=9.3 and 1.2 Hz); 7.82 (dd, 1H, J=9.3 and 1.2 Hz); 6.25-6.10 (m, NH, 1H); 4.33-4.17 (m, 1H), 4.07-4.00 (m, 2H), 3.59-3.51 (m, 2H), 2.07-2.03 (m, 2H) and 1.69-1.58 ppm (m, 2H).

EXAMPLE 15

N-(Tetrahydro-2H-pyran-3-yl)-[2,1,3]-benzoxadiazole-5-carboxamide

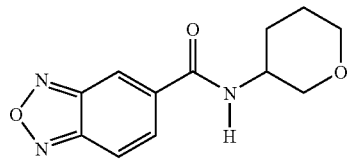

N-(Tetrahydro-2H-pyran-3-yl)-[2,1,3]-benzoxadiazole-5-carboxamide was prepared from 3-aminotetrahydropyran hydrochloride and [2,1,3]-benzoxadiazole-5-carbonylchloride using the procedure described for Example 7. Mp=204-205° C., $^1$H NMR (300 MHz, CDCl$_3$) δ 8.24-8.10 (m, 1H), 7.93 (dd, 1H, J=9.0 and 0.9 Hz); 7.84 (dd, 1H, J=9.0 and 1.2 Hz); 6.70-6.60 (m, NH, 1H); 4.24-4.22 (m, 1H), 3.86-3.60 (m, 4H) and 1.97-1.61 ppm (m, 4H).

EXAMPLE 16

N-Methyl-N-(tetrahydro-2H-pyran-3-yl)-[2,1,3]-benzoxadiazole-5-carboxamide

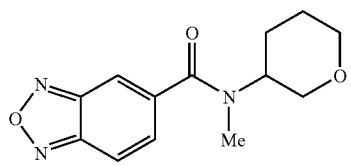

N-(Tetrahydro-2H-pyran-3-yl)-[2,1,3]-benzoxadiazole-5-carboxamide (371 mg, 1.5 mmol) was added to a suspension of sodium hydride (216 mg, 9 mmol) in dry DMF (5 ml), followed by methyl iodide (1.0 ml) and the mixture was stirred at 20° C. for 1 hour. The solvent was evaporated under vacuum, dichloromethane (30 ml) was added and the organic phase was washed with 1N HCl (100 ml) and NaHCO$_3$ solution (100 ml). The aqueous was re-extracted with dichloromethane (100 ml), the organics dried over magnesium sulfate and concentrated under vacuum to give the title compound as a white solid after trituration with diethyl ether (186 mg). Mp: 134-135° C., $^1$H NMR (300 MHz, CDCl$_3$) δ 7.93 (d, 1H, J=9.0 Hz); 7.83 (s, 1H); 7.40 (d, 1H, J=9.0 Hz); 4.70-3.20 (m, 4H), 3.01 (sb, 3H) and 2.10-1.50 ppm (m, 4H).

EXAMPLE 17

N-Ethyl-N-tetrahydro-2H-pyran-4-[2,1,3]-benzoxadiazole-5-carboxamide

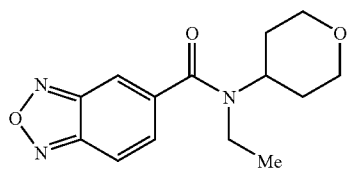

To a solution of tetrahydro-4H-pyran-4-one (1.0 g, 10 mmol) in methanol (60 ml) was added ethylamine hydrochloride (815 mg, 10 mmol), 1 ml of NEt$_3$, and 10% Pd on C (350 mg). The mixture was hydrogenated at room temperature over night (18 hours). The solids were filtered, washed with methanol (20 ml) and concentrated under vacuum. The residue was dissolved in chloroform (70 ml) and NEt$_3$ (2 ml) and a solution of [2,1,3]-benzoxadiazole-5-carbonylchloride (600 mg, 3.28 mmol) in chloroform (10 ml) was added slowly. After stirring for 0.5 h, the mixture was washed with water (100 ml) and H$_2$SO$_4$ (→pH 2) and NaHCO$_3$ solution (100 ml). The aqueous was extracted with chloroform (100 ml) and the combined organics were dried over MgSO$_4$ and concentrated under vacuum to give an oil.

Chromatography on silica gel eluting with ethyl acetate/hexane (75:25) and chloroform/acetone (85:15), gave white solid after crystallization from diethyl ether (470 mg). Mp=102-4° C., LC-MS, MH$^+$=276; $^1$H NMR (300 MHz, CDCl$_3$, 2 rotamers) δ 7.93 (d, 1H, J=9.0 Hz); 7.80 (s, 1H);

7.38 (d, 1H, J=9.0 Hz); 4.75-4.45 and 4.15-3.90 and 3.75-3.05 (m+m+m, 7H); 2.04-1.05 ppm (m, 7H).

EXAMPLE 18

N-Cyclohexyl-N-ethyl-[2,1,3]-benzoxadiazole-5-carboxamide

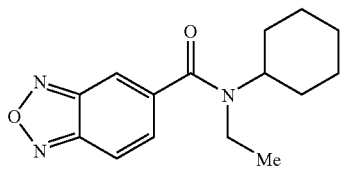

The title compound was prepared from ethylamine hydrochloride and cyclohexanone using the procedures described for Example 17. After silica gel chromatography the product was isolated as a white solid. Mp=51-2° C., LC-MS, MH+=274; $^1$H NMR (300 MHz, CDCl$_3$, 2 rotamers) δ 7.91 (d, 1H, J=9.0 Hz); 7.78 (s, 1H); 7.76 (d, 1H, J=9.0 Hz); 4.4-4.3 and 3.55-3.2 (m+m, 3H); 1.95-0.95 ppm (m, 13H).

EXAMPLE 19

N-(Cyclohexylmethyl)-N-methyl-[2,1,3]-benzoxadiazole-5-carboxamide

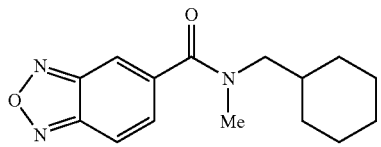

The title compound was prepared from cyclohexyl-4-methylamine using the methods described for Example 4 and was isolated as a white solid. Mp=71-2° C., LC-MS, MH+=274; $^1$H NMR (300 MHz, CDCl$_3$, 2 rotamers) δ 7.94-7.78 (m, 2H); 7.48-7.38 (m, 1H); 3.43+3.16 (d+d, 2H); 3.10 and 3.01 (s+s, 3H); 1.90-1.55 and 1.47-0.95 and 0.73-0.57 ppm (m+m+m, 11H).

EXAMPLE 20

N-Benzyl-N-methyl-[2,1,3]-benzoxadiazole-5-carboxamide

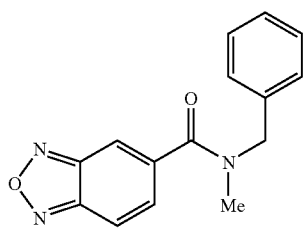

Prepared from N-benzyl-N-methylamine and [2,1,3]-benzoxadiazole-5-carbonylchloride according to the procedure previously described. N-Benzyl-N-methyl-[2,1,3]-benzoxadiazole-5-carboxamide was isolated as a white solid. Mp=105-106° C., LC-MS, MH+=268; $^1$H NMR (300 MHz, CDCl$_3$, 2 rotamers) δ 7.96-7.86 (m, 1H); 7.90 (d, 1H, J=9.6 Hz); 7.43-7.30 (m, 5H); 7.19-7.13 (m, 1H); 4.78+4.56 (s+s, 2H); 3.11 and 2.94 ppm (s+s, 3H).

EXAMPLE 21

N-Methyl-N-(tetrahydrofuran-2-ylmethyl)-[2,1,3]-benzoxadiazole-5-carboxamide

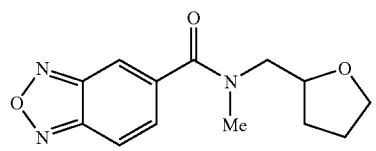

Prepared by N-methylation of the product of the reaction of tetrahydrofuran-2-methylamine and [2,1,3]-benzoxadiazole-5-carbonylchloride as described for the preparation of Examples 7 and 16. N-Methyl-N-(tetrahydrofuran-2-ylmethyl)-[2,1,3]-benzoxadiazole-5-carboxamide Was isolated as a pale yellow oil. LC-MS, MH+=262; $^1$H NMR (300 MHz, CDCl$_3$, 2 rotamers) δ 7.94-7.85 (m, 2H); 7.51-7.44 (m, 1H); 4.31-3.22 (m, 5H); 3.18 and 3.14 (s+s, 3H); 2.18-1.25 ppm (m, 4H).

EXAMPLE 22

N-Methyl-N-pyridin-3-yl-[2,1,3]-benzoxadiazole-5-carboxamide

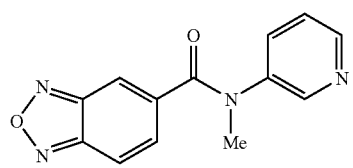

Prepared from 3-aminopyridine using the experimental procedures described for Example 4. N-Methyl-N-pyridin-3-yl-[2,1,3]-benzoxadiazole-5-carboxamide was isolated as a yellow oil. LC-MS, MH+=255; $^1$H NMR (300 MHz, CDCl$_3$) δ 8.44 (d, 1H, J=4.8 Hz); 8.39 (d, 1H, J=2.1 Hz); 7.74 (s, 1H); 7.72 (d, 1H, J=9 Hz); 7.51 (dd, 1H, J=8.4 and 2.1 Hz); 7.35 (d, 1H, J=9 Hz); 7.27 (dd, 1H, J=8.4 and 4.8 Hz); 3.56 ppm (s, 3H).

EXAMPLE 23

N-Methyl-N-phenyl-[2,1,3]-benzoxadiazole-5-carboxamide

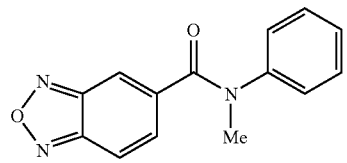

Prepared from N-methylaniline and [2,1,3]-benzoxadiazole-5-carbonylchloride using the procedure described for Example 7. N-Methyl-N-phenyl-[2,1,3]-benzoxadiazole-5-carboxamide was isolated as a yellow oil. LC-MS, MH$^+$=254; $^1$H NMR (300 MHz, CDCl$_3$) δ 7.74 (s, 1H); 7.64 (d, 1H, J=9.6 Hz); 7.34 (d, 1H, J=9.6 Hz); 7.29-7.09 (m, 5H); 3.54 ppm (s, 3H).

EXAMPLE 24

N-Cyclopropyl-N-tetrahydro-2H-pyran-4-yl-[2,1,3]-benzoxadiazole-5-carboxamide

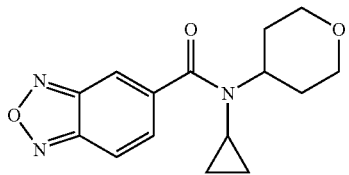

N-Cyclopropyl-N-tetrahydro-2H-pyran-4-yl-[2,1,3]-benzoxadiazole-5-carboxamide was prepared from tetrahydro-4H-pyran-4-one and cyclopropylamine using the procedures described for Example 17 and was isolated as a white solid. Mp=108-109° C., LC-MS, MH$^+$=288; $^1$H NMR (300 MHz, CDCl$_3$) δ 7.91 (t, 1H, J=1.0 and 1.0 Hz, 1H); 7.76 (dd, J=9.2 and 1.0 Hz, 1H); 7.51 (dd, J=9.2 and 1.0 Hz, 1H); 4.50-4.39 (m, 1H); 4.11-4.06 (m, 2H); 3.58-3.49 (m, 2H); 2.70-2.60 (m, 1H); 2.28-2.12 (m, 2H); 1.90-1.85 (m, 2H); 0.75-0.53 ppm (m, 4H).

EXAMPLE 25

N-Tetrahydro-2H-pyran-4-yl-N-(2,2,2-trifluoroethyl)-[2,1,3]-benzoxadiazole-5-carboxamide

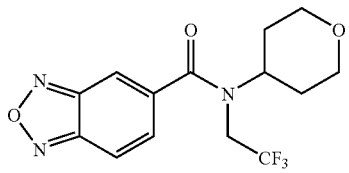

The title compound was prepared from tetrahydro-4H-pyran-4-one and 2,2,2-trifluoroethylamine using the procedures described for Example 17 and was isolated as a white solid. Mp=134-135° C., LC-MS, MH$^+$=330; $^1$H NMR (300 MHz, CDCl$_3$) δ 7.79 (dd, J=9.2 and 1.0 Hz, 1H); 7.91-7.85 (m, 1H); 7.40 (dd, J=9.2 and 1.0 Hz, 1H); 4.20-3.85 (m, 5H); 3.35-3.15 (m, 2H); 2.02-1.65 ppm (m, 4H).

EXAMPLE 26 tert-Butyl-4-[([2,1,3]-benzoxadiazol-5-ylcarbonyl)(methyl)amino]piperidine-1-carboxylate

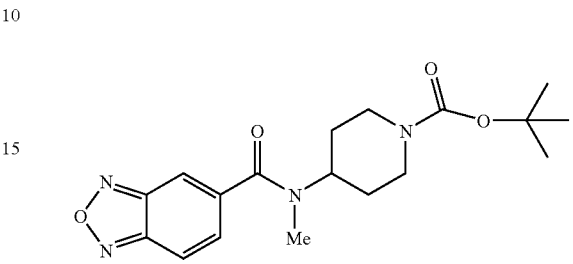

Methylamine (generated by heating a mixture of 10 g of methylamine hydrochloride and 18 g of sodium hydroxide) was condensed into a solution of Boc-4-piperidone (3.5 g, 17.6 mmol) in methanol (30 ml) and THF (30 ml). 10% Pd on C (600 mg) was added and the mixture was hydrogenated at room temperature for 18 hours. The solids were filtered off, washed with methanol (20 ml) and concentrated under vacuum. The residue was dissolved in chloroform (50 ml) and NEt$_3$ (4 ml), and a solution of [2,1,3]-benzoxadiazole-5-carbonylchloride (2.1 g, 11.5 mmol) in dichloromethane (20 ml) was added slowly. After stirring the mixture for 1 h, the organic phase was washed with water (100 ml) and H$_2$SO$_4$ (→pH 2) and NaHCO$_3$ solution (100 ml). The aqueous was extracted with chloroform (100 ml), the organics combined, dried (MgSO$_4$) and concentrated under vacuum to give an oil. The crude product was purified by silica gel chromatography eluting with ethyl acetate/hexane (40:60) →(60:40) to give a white solid after crystallization from MTBE/hexane (3.14 g). Mp=98-100° C., LC-MS, MH$^+$=361; $^1$H NMR (300 MHz, CDCl$_3$) δ 7.93 (d, J=9.0 Hz, 1H); 7.84 (s, 1H); 7.42 (d, J=9.0 Hz, 1H); 4.80-3.40 (m, 5H); 3.10-2.85 (m, 3H); 1.90-1.60 (m, 4H); 1.47 ppm (s, 9H).

EXAMPLE 27

N-Methyl-N-piperidin-4-yl-[2,1,3]-benzoxadiazole-5-carboxamide. Hydrochloride

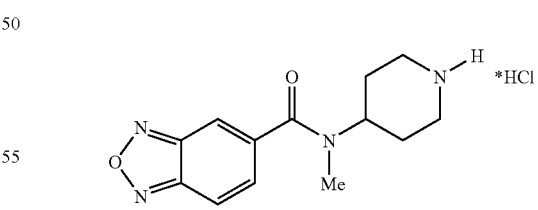

tert-Butyl-4-[([2,1,3]-benzoxadiazol-5-ylcarbonyl)(methyl)amino)]piperidine-1-carboxylate (1.2 g, 3.33 mmol) was dissolved in chloroform (30 ml) and TFA (3 ml) was added and the mixture was stirred at room temperature for 2 hours. The mixture was concentrated under vacuum and the residue was dissolved in chloroform (30 ml) ethanol (30 ml) and conc. HCl (1 ml). The mixture was concentrated under vacuum to give a solid that was washed with a mixture of chloroform, ethanol and THF to yield an off white solid (920 mg). Mp>260° C., $^1$H NMR (300 MHz, DMSO) δ 9.04-8.78 (m, 2H); 8.20-8.05 (m, 2H); 7.62-7.52 (m, 1H); 4.70-4.50 and 3.88-3.72 (m, 1H); 3.30-2.70 (m, 7H) and 2.20-1.80 ppm (m, 4H).

EXAMPLE 28

N-Methyl-N-(1-methylpiperidin-4-yl)-[2,1,3]-benzoxadiazole-5-carboxamide

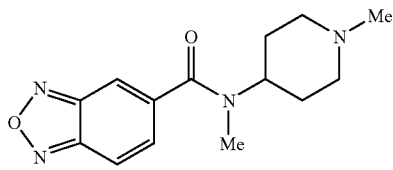

Prepared by N-methylation of N-methyl-N-piperidin-4-yl-[2,1,3]-benzoxadiazole-5-carboxamide as described for Example 16 and isolated as a beige solid after crystallization from ethyl acetate/dichloromethane. Mp>260° C., LC-MS, MH$^+$=275.2; $^1$H NMR (300 MHz, CDCl$_3$) δ 7.28-7.20 (m, 2H); 6.67 (d, J=9.6 Hz, 1H); 3.70-6.57 and 2.90-2.70 (m, 1H); 3.70-1.95 ppm (m, 14H).

EXAMPLE 29

N-(1-Acetylpiperidin-4-yl)-N-methyl-[2,1,3]-benzoxadiazole-5-carboxamide

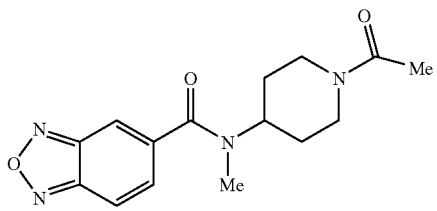

N-Methyl-N-piperidin-4-yl-[2,1,3]-benzoxadiazole-5-carboxamide hydrochloride (0.58 g, 1.9 mmol) was suspended in chloroform (50 ml), and acetic anhydride (2 ml) and triethylamine (4 ml), were added. After stirring for 1 h, the mixture was washed with water (100 ml) and H$_2$SO$_4$ (→pH 2) and NaHCO$_3$ solution (100 ml). The aqueous was extracted with chloroform (2×100 ml) and the combined organics dried (MgSO$_4$) and concentrated under vacuum. The residue was purified by silica gel chromatography eluting with ethyl acetate/chloroform/methanol (50:45:5) to give a white solid after crystallization from ethyl acetate/MTBE/hexane (470 mg). Mp=173-175° C., $^1$H NMR (300 MHz, CDCl$_3$) δ 7.93 (d, J=9.0 Hz, 1H); 7.85 (s, 1H); 7.42 (d, J=9.0 Hz, 1H); 4.90-4.70 and 4.05-3.80 (m, 5H); 2.89 (sb, 3H); 2.13 (sb, 3H), 1.95-1.60 ppm (m, 4H).

EXAMPLE 30

N-(1-Formylpiperidin-4-yl)-N-methyl-[2,1,3]-benzoxadiazole-5-carboxamide

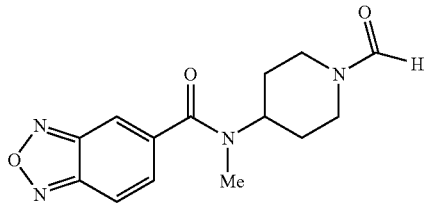

N-Methyl-N-piperidin-4-yl-[2,1,3]-benzoxadiazole-5-carboxamide hydrochloride (0.5 g, 1.7 mmol) was suspended in chloroform (20 ml) and THF (20 ml) and triethylamine (6 ml), was added. A mixture of formic acid (1 ml) and acetic anhydride (1 ml) was stirred for 1.5 h at room temperature and then slowly added to the suspension. After stirring the mixture for 1 h, it was washed with water (100 ml) and H$_2$SO$_4$ (→pH 2) and NaHCO$_3$ solution (100 ml). The aqueous was extracted with chloroform (2×100 ml) and the combined organics were dried (MgSO$_4$), concentrated under vacuum, and purified by silica gel chromatography, eluting with ethyl acetate/chloroform/methanol (50:45:5) to give a white solid (341 mg). Mp=163-165° C., $^1$H NMR (300 MHz, CDCl$_3$) δ 8.05 (s, 1H), 7.93 (d, J=9.3 Hz, 1H); 7.86 (s, 1H); 7.42 (d, J=9.3 Hz, 1H); 4.90-4.45 and 3.85-2.60 (m, 5H); 2.88 (sb, 3H); and 1.95-1.60 ppm (m, 4H).

EXAMPLE 31

N-Methyl-N-[1-(methylsulfonyl]piperidin-4-yl)-[2,1,3]-benzoxadiazole-5-carboxamide

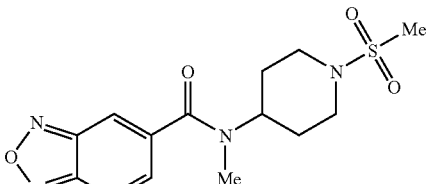

N-Methyl-N-piperidin-4-yl-[2,1,3]-benzoxadiazole-5-carboxamide hydrochloride (0.38 g, 1.3 mmol) was suspended in chloroform (70 ml) and triethylamine (2 ml) was added. A solution of methane sulfonyl chloride (0.14 g, 1.26 mmol) in chloroform (10 ml) was added and the mixture was stirred at 20° C. for 2 h. The mixture was washed with water (50 ml) and H$_2$SO$_4$ (→pH 2) and NaHCO$_3$ solution (50 ml) and the aqueous re-extracted with dichloromethane (2×50 ml). The combined organics were dried (MgSO$_4$), concentrated under vacuum, and the crude product was purified on a silica gel column eluting with dichloromethane/THF (85:15) to give a white crystalline product, after crystallization from MTBE/hexane (204 mg). Mp=177-179° C., $^1$H NMR (300 MHz, CDCl$_3$) δ 7.93 (d, J=9.3 Hz, 1H); 7.85 (s, 1H); 7.42 (d, J=9.3 Hz, 1H); 4.75-4.46 and 4.10-3.90 and 3.10-2.40 (m, 5H); 2.92 (s, 3H), 2.83 (s, 3H) and 2.10-1.70 ppm (m, 4H).

EXAMPLE 32

N-Methyl-N-(tetrahydro-2H-pyran-4-yl)-[2,1,3]-benzothiadiazole-5-carboxamide

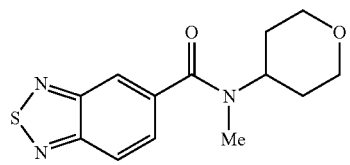

N-Methyltetrahydro-2H-pyran-4-amine (0.4 g, 3.4 mmol), [2,1,3]-benzothiadiazole-5-carboxylic acid (0.23 g, 1.4 mmol), DMAP (0.2 g: 1.6 mmol), HOBT (0.2 g, 1.5 mmol), triethylamine (1.0 ml) and EDCI (1 g, 6.4 mmol) were dissolved in DMF (30 ml). The mixture was stirred at room temperature for 18 h and then concentrated under vacuum. Chloroform (100 ml) was added and the mixture washed with water (100 ml) and $H_2SO_4$ (→pH 2) and $NaHCO_3$ solution (100 ml). The aqueous was extracted with chloroform (100 ml) and the combined organics were dried ($MgSO_4$), concentrated under vacuum, and the crude product was purified on a silica gel column eluting with chloroform/THF (90:10), to give the product as an oil which crystallized on standing. Mp=106-108° C., $^1$H NMR (300 MHz, CDCl$_3$, rotamers) δ 8.06 (d, J=9.0 Hz, 1H); 8.01 (s, 1H); 7.60 (d, J=9.0 Hz, 1H); 4.92-4.75 and 4.15-3.10 (m, 5H); 3.10-2.80 (m, 3H) and 2.05-1.50 ppm (s, 4H).

EXAMPLE 33

N-Methyl-N-(tetrahydro-2H-thiopyran-4-yl)-[2,1,3]-benzoxadiazole-5-carboxamide

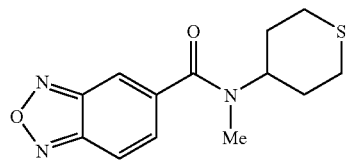

Tetrahydro-2H-thiopyran-4-one (1.0 g, 8.6 mmol) was dissolved in methanol (40 ml), and methylamine in ethanol (3.3 ml of a 33% solution) was added and the mixture stirred at room to temperature for 1 h. The mixture was cooled to −78° C. and a suspension of LiBH$_4$ (0.34 g) in THF (10 ml) was added and stirred for 18 h whilst warming up to room temperature. Water (1 ml) was added and then evaporated and the residue dissolved in chloroform (20 ml). Triethylamine (2 ml) was added and the mixture cooled to 0° C. before adding slowly a solution of [2,1,3]-benzoxadiazole-5-carbonylchloride (1.28 g, 7 mmol) in chloroform (15 is ml). The mixture was stirred for 0.5 h and then washed with water (100 ml) and HCl (→pH 2) and NaHCO$_3$ solution (100 ml). The aqueous was extracted with chloroform (100 ml) and the combined organics were dried (MgSO$_4$) and concentrated under vacuum to give a white solid after trituration with diethyl ether (1.6 g). Mp=155-156° C., $^1$H NMR (300 MHz, CDCl$_3$, rotamers) δ 7.92 (d, J=9.3 Hz, 1H); 7.83 (sb, 1H); 7.40 (d, J=9.3 Hz, 1H); 4.60-4.45 and 3.50-3.30 (m, 1H); 3.10-2.40 (m, 7H) and 2.20-1.85 ppm (s, 4H).

EXAMPLE 34

N-Methyl-N-(1-oxidotetrahydro-2H-thiopyran-4-yl)-[2,1,3]-benzoxadiazole-5-carboxamide

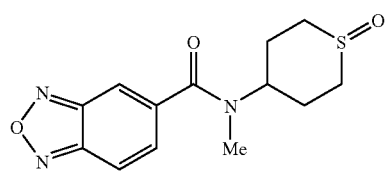

N-Methyl-N-(tetrahydro-2H-thiopyran-4-yl)-[2,1,3]-benzoxadiazole-S-carboxamide (0.83 mg, 3 mmol) was dissolved in THF (30 ml) and methanol (20 ml). A solution of sodium periodate (0.71 g) in water (30 ml) was added and the mixture stirred over night. The solvents were evaporated and the product was purified by silica gel chromatography eluting with chloroform/THF/methanol (60:20:20), to give two sulfone isomers. The less polar isomer was isolated as a white solid (0.35 g). Mp=172-173° C., $^1$H NMR (300 MHz, CDCl$_3$, rotamers) δ 7.94 (d, J=9.3 Hz, 1H); 7.87 (sb, 1H); 7.43 (d, J=9.3 Hz, 1H); 4.80-4.65 and 3.70-3.50 (m, 1H); 3.0 (s, 3H), 3.30-1.60 ppm (m, 8H). The more polar isomer was isolated as a 2:1 mixture with the less polar isomer (0.45 g). Mp=145-146° C., $^1$H NMR (300 MHz, CDCl$_3$, rotamers) δ 7.96-7.85 (m, 2H); 7.45-7.39 (m, 1H); 4.80-4.65 and 3.70-3.40 (m, 1H); 3.0 (s, 3H), 3.30-1.70 ppm (m, 8H).

EXAMPLE 35

N-Methyl-N-(1,1-dioxidotetrahydro-2H-thiopyran-4-yl)-[2,1,3]-benzoxadiazole-5-carboxamide

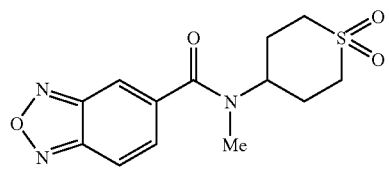

N-Methyl-N-(tetrahydro-2H-thiopyran-4-yl)-[2,1,3]-benzoxadiazole-5-carboxamide (0.5 g, 1.8 mmol) was dissolved in chloroform (40 ml) and m-chloroperbenzoic acid (0.93 g) was added and stirred for 1 h. The mixture was washed with Na$_2$CO$_3$ solution (100 ml), dried over MgSO$_4$ and evaporated and the residue crystallized from dichloromethane/diethyl ether to give a white solid (44 mg). Mp=238-239° C., $^1$H NMR (300 MHz, CDCl$_3$) δ 7.95 (d, J=9.0 Hz, 1H); 7.87 (sb, 1H); 7.41 (d, J=9.0 Hz, 1H); 4.90-4.70 (m, 1H); 3.35-3.10 (m, 4H); 2.97 (s, 3H); 2.60-2.10 ppm (m, 4H).

EXAMPLE 36

N-Methyl-N-tetrahydro-2H-pyran-4-ylquinoxaline-6-carboxamide

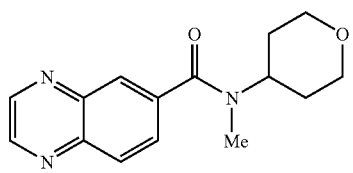

To a suspension of quinoxaline-6-carboxylic acid (0.7 g, 4 mmol) and N-methyltetrahydro-2H-pyran-4-amine (0.7 g, 6 mmol), in DMF (6 ml) and dichloromethane (6 ml), were added DMAP (0.49 g, 4 mmol), HOBT (0.54 g, 4 mmol), NEt$_3$ (1.6 ml) and EDCI (1.26 g). The reaction mixture was stirred at room temperature for 4 h and then concentrated under vacuum. The crude product was purified on a silica gel column eluting with chloroform/methanol/triethylamine (95:5:0.5) to give an oil (1.5 g) which formed a beige solid upon trituration with dichloromethane/diethyl ether. Mp=130-131° C., LC-MS, MH$^+$=272; $^1$H NMR (300 MHz, CDCl$_3$) δ 8.91 (s, 2H); 8.18 (d, J=8.4 Hz, 1H); 8.11 (s, 1H); 7.79 (d, J=8.4 Hz, 1H); 4.95-3.50 (m, 5H); 3.07 and 2.91 (s+s, 3H); 2.02-1.65 ppm (m, 4H).

EXAMPLE 37

N-Methyl-N-(4-oxocyclohexyl)-[2,1,3]-benzoxadiazole-5-carboxamide

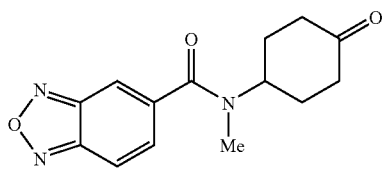

1,4-Cyclohexanedione mono-ethylene ketal (3.12 g, 20 mmol), methylamine hydrochloride (1.35 g, 20 mmol) and triethylamine (2.42 g) were dissolved in methanol (80 ml) and 10% Pd on C (1 g) was added and the mix hydrogenated at room temperature at 50 PSI for 2 h. The solids were filtered off, washed with methanol (40 ml) and the mixture concentrated under vacuum. The product was dissolved in chloroform (75 ml) and triethylamine (4 ml) was added followed by slow addition of a solution of [2,1,3]-benzoxadiazole-5-carbonylchloride (2.74 g, 15 mmol) in chloroform (15 ml). After stirring the mixture for 1 h it was washed with water (100 ml) and HCl (→pH 2) and NaHCO$_3$ solution (100 ml). The aqueous was extracted with chloroform (100 ml) and the combined organics were dried (MgSO$_4$) and concentrated under vacuum to give the product as a yellow solid (4.2 g). This material was dissolved in THF (30 ml), and 2N HCl (40 ml) was added and the mixture stirred overnight. The THF was evaporated and the remaining aqueous was extracted with dichloromethane (100 ml), washed with water (100 ml) and sat. NaHCO$_3$ solution (100 ml), and dried over MgSO$_4$. The solvent was evaporated under vacuum to give a beige solid (3.5 g) which was crystallized from dichloromethane/diethyl ether to give a white solid. Mp=183-184° C., LC-MS, MH$^+$=274; $^1$H NMR (300 MHz, CDCl$_3$, rotamers) δ 7.95 (d, J=9.0 Hz, 1H); 7.87 (m, 1H); 7.40 ("d", J=9.0 Hz, 1H); 5.10-4.95 and 4.10-3.90 (m, 1H); 2.93 ("s", 3H); 2.70-1.95 ppm (s, 8H).

EXAMPLE 38

N-[4-(Hydroxyimino)cyclohexyl]-N-methyl-[2,1,3]-benzoxadiazole-5-carboxamide

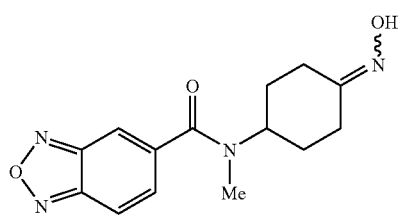

N-Methyl-N-(4-oxocyclohexyl)-[2,1,3]-benzoxadiazole-5-carboxamide (0.41 g, 1.5 mmol) was dissolved in chloroform (10 ml), hydroxylamine hydrochloride (0.63 g) and triethylamine (1.6 ml) were added, and the mixture stirred overnight. Evaporation of the solvent and to chromatography of the residue on silica gel, eluting with chloroform/ethyl acetate (3:2), gave a white solid (0.37 g). Mp=197-198° C., NMR (300 MHz, CDCl$_3$) δ 8.49 (s, 1H); 7.93 (d, J=9.0 Hz, 1H); 7.86 (m, 1H); 7.43 (d, J=9.0 Hz, 1H); 4.90-4.70 and 3.80-3.35 (m, 1H); 2.99 and 2.88 (s+s, 3H); 2.80-1.50 ppm (s, 8H).

EXAMPLE 39

N-[4-(Methoxyimino)cyclohexyl]-N-methyl-[2,1,3]-benzoxadiazole-5-carboxamide

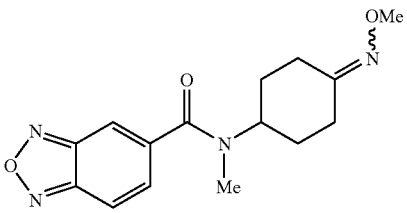

N-Methyl-N-(4-oxocyclohexyl)-[2,1,3]-benzoxadiazole-5-carboxamide (0.41 g, 1.5 mmol) was dissolved in chloroform (10 ml), methoxylamine hydrochloride (0.75 g) and triethylamine (1.6 ml) were added, and the mixture stirred overnight. Evaporation of the solvent and chromatography of the residue on silica gel, eluting with chloroform/ethyl acetate (3:2), gave a white solid (0.32 g). Mp=167-168° C., NMR (300 MHz, CDCl$_3$) δ 7.93 (d, J=9.3 Hz, 1H); 7.84 (m, 1H); 7.42 (d, J=9.3 Hz, 1H); 4.85-4.70 and 3.80-3.30 (m, 1H); 3.83 (s, 3H); 2.99 and 2.88 (s+s, 3H); 2.60-1.60 ppm (s, 8H).

EXAMPLE 40 and EXAMPLE 41

N-(4,4-Difluorocyclohexyl)-N-methyl-[2,1,3]-benzoxadiazole-5-carboxamide and N-(4-fluorocyclohex-3-en-1-yl)-N-methyl-[2,1,3]-benzoxadiazole-5-carboxamide

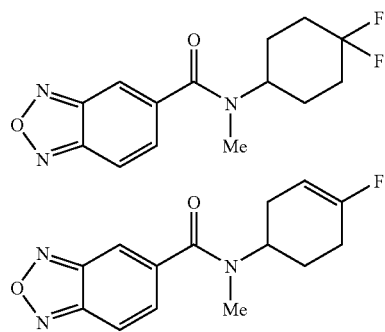

N-Methyl-N-(4-oxocyclohexyl)-[2,1,3]-benzoxadiazole-5-carboxamide (1.5 g, 5.5 mmol) was dissolved in dichloromethane (50 ml) and cooled to 0° C. Diethylaminosulfur trifluoride, "DAST" (1.8 ml, 2.4 equivalents) was added slowly and the mixture stirred at room temperature for 3 h. The solution was diluted with dichloromethane (100 ml) and NaHCO$_3$ solution was added slowly until pH 9 was reached. The organic phase was washed with brine, dried over MgSO$_4$ and evaporated. The crude product was chromatographed on a silica gel eluting with hexane/ethyl acetate (65:35) to give N-(4,4-difluorocyclohexyl)-N-methyl-[2,1,3]-benzoxadiazole-5-carboxamide (0.32 g) as a white solid after trituration with ether. Mp=137-138° C., LC-MS, MH$^+$=296; $^1$H NMR (300 MHz, CDCl$_3$, rotamers) δ 7.93 (d, J=9.0 Hz, 1H); 7.84 (s, 1H); 7.41 (d, J=9.0 Hz, 1H); 4.75-4.60 and 3.65-3.55 (m, 1H); 3.01 and 2.91 (s+s, 3H); 2.30-1.60 ppm (s, 8H).

A second product was isolated as N-(4-fluorocyclohex-3-en-1-yl)-N-methyl-[2,1,3]-benzoxadiazole-5-carboxamide (0.1 g) as a white solid after trituration with diethyl ether. Mp=117-118° C., LC-MS, MH$^+$=276; $^1$H NMR (300 MHz, CDCl$_3$, rotamers) δ 7.93 (d, J=9.0 Hz, 1H); 7.84 (s, 1H); 7.41 (d, J=9.0 Hz, 1H); 5.30-5.00 (m, 1H); 4.90-4.70 and 3.80-3.65 (m, 1H); 3.02 and 2.92 (s+s, 3H); 2.60-1.80 ppm (s, 6H).

EXAMPLE 42

N-(4-trans-Hydroxycyclohexyl)-[2,1,3]-benzoxadiazole-5-carboxamide

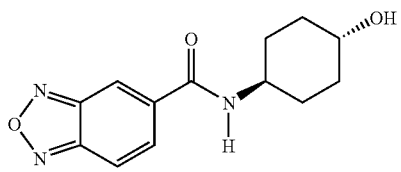

To a mixture of trans 4-aminocyclohexanol hydrochloride (0.46 g, 3.0 mmol) and [2,1,3]-benzoxadiazole-5-carboxylic acid (0.33 g, 2.0 mmol) in chloroform (10 ml), were added DMAP (0.24 g, 2.0 mmol), HOBT (0.27 g, 2.0 mmol) and triethylamine (1.6 ml). After stirring for 10 minutes, EDCI (1.26 g, 6.6 mmol) in DMF (3 ml) was added and the mixture was heated to 45° C. for 2 h. The solvents were removed under vacuum and the crude product was purified by silica gel chromatography eluting with ethyl acetate/chloroform (3:1) to give a white solid after trituration with ethyl acetate (0.4 g). Mp=242-243° C., $^1$H NMR (300 MHz, DMSO+CDCl$_3$) δ 8.41-8.39 (m, 1H), 7.95 (dd, J=9.3 and 1.2 Hz, 1H); 7.85 (d, J=9.3 Hz, 1H); 7.82 ("s", NH, 1H), 4.00-3.88 (m, 1H), 3.70-3.50 (m, 2H); 2.15-1.95 (m, 4H); 1.55-1.35 ppm (m, 4H).

EXAMPLE 43

N-(trans-4-Hydroxy-4-methylcyclohexyl)-[2,1,3]-benzoxadiazole-5-carboxamide

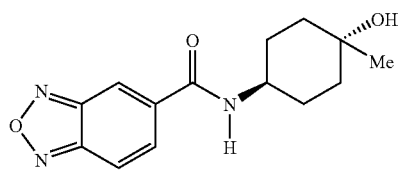

Prepared from trans-4-amino-1-methylcyclohexanol using the method described for Example 42. The product was isolated as a white solid. Mp=208-209° C., $^1$H NMR (300 MHz, DMSO+CDCl$_3$) δ 8.18-8.16 (m, 1H), 7.91 (d, J=9.6 Hz, 1H); 7.82 (dd, J=9.6 and 0.9 Hz, 1H); 6.10 ("s", NH, 1H), 4.05-3.90 (m, 1H), 2.00-1.50 (m, 8H); 1.29 ppm (s, 3H).

EXAMPLE 44 and EXAMPLE 45

N-(cis-4-Hydroxy-4-methylcyclohexyl)-N-methyl-[2,1,3]-benzoxadiazole-5-carboxamide and N-(trans-4-hydroxy-4-methylcyclohexyl)-N-methyl-[2,1,3]-benzoxadiazole-5-carboxamide

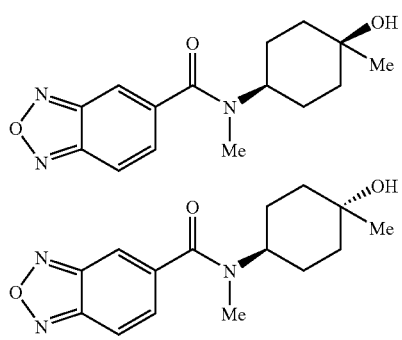

To a mixture of 1,4-cyclohexanedione mono-ethylene ketal (5.0 g, 32 mmol), methylamine hydrochloride (2.16 g, 32 mmol) and triethylamine (6.7 ml), in methanol (100 ml), was added 10% Pd on C (1 g) and the mixture was hydrogenated at room temperature (50 PSI) for 2 h. The solids were filtered off, washed with methanol (40 ml) and concentrated under vacuum. The residue was dissolved in methanol (10 ml), THF (50 ml) and 2N HCl (65 ml) and stirred for 18 h. Sodium hydroxide solution (concn) was added to pH 10, the aqueous extracted with dichloromethane (5×100 ml), the combined organics dried (MgSO$_4$) and concentrated under vacuum to give 4-N-methylaminocyclohexanone (4.97 g).

This material was slowly added to a solution of di-tert-butyl dicarbonate (8.38 g) in dichloromethane (80 ml) and the mixture stirred for 2 h. The mixture was washed with water, dried over MgSO₄, evaporated under vacuum and the residue chromatographed on silica gel eluting with ethyl acetate/hexane (30:70) to give tert-butyl-(4-cyclohexanone)methylcarbamate as a white solid (6.14 g). To a solution of the preceding ketone (0.91 g, 4.0 mmol) in anhydrous THF (100 ml) at −70° C. was added methyl magnesium bromide (6 mmol) and the mixture stirred for 1 h. The mixture was poured into 2N NH₄Cl solution and the pH was adjusted to 7 using citric acid. The aqueous was extracted with dichloromethane (5×100 ml), the combined organics dried (MgSO₄) and evaporated to give an oil (1 g) which was chromatographed on silica gel eluting with ethyl acetate/hexane (1:1) to give tert-butyl(cis-4-hydroxy-4-methylcyclohexyl)methylcarbamate (0.42 g) as a colorless oil and as the less polar isomer, and tert-butyl(trans-4-hydroxy-4-methylcyclohexyl)methylcarbamate (0.4 g) as a white solid. tert-Butyl(cis-4-hydroxy-4-methylcyclohexyl)methylcarbamate (0.42 g) was dissolved in dichloromethane (10 ml) and TFA (2 ml) added, and stirred for 3 h. The solvent was evaporated under vacuum and the residue dissolved in dichloromethane (10 ml) and conc. HCl (1 ml). The solvent was evaporated and the material was dried over night under high vacuum. The residue was dissolved in DMF (5 ml) and chloroform (3 ml), and [2,1,3]-benzoxadiazole-5-carboxylic acid (0.28 g, 1.7 mmol), DMAP (0.21 g 1.7 mmol), HOBT (0.23 g 1.7 mmol) and triethylamine (1.4 ml) were added. After 0.1 h, EDCI (1.07 g, 5.6 mmol) was added and after stirring for 2 h at 45° C., the solvents were evaporated. The residue was chromatographed on silica gel eluting with ethyl acetate/chloroform (3:1) to give N-(cis-4-hydroxy-4-methylcyclohexyl)-N-methyl-[2,1,3]-benzoxadiazole-5-carboxamide as a white solid (0.34 g) after trituration with diethyl ether. Mp=154-155° C., ¹H NMR (300 MHz, CDCl₃) δ 7.91 (d, J=9.3 Hz, 1H), 7.82 (sb, 1H); 7.46-7.37 (m, 1H); 4.60-4.45 and 3.50-3.30 (m, 1H), 3.05 and 2.91 (s+s, 3H); 2.10-1.00 (m, 8H) and 1.29 and 1.16 ppm (s+s, 3H).

N-(trans-4-Hydroxy-4-methylcyclohexyl)-N-methyl-[2,1,3]-benzoxadiazole-5-carboxamide was prepared using the procedures above from tert-butyl(trans-4-hydroxy-4-methylcyclohexyl)methyl carbamate and isolated as a white solid. Mp=175-176° C., ¹H NMR (300 MHz, CDCl₃) δ 7.92 (d, J=9.0 Hz, 1H), 7.82 (s, 1H); 7.40 (d, J=9.0 Hz, 1H); 4.60-4.45 and 3.60-3.40 (m, 1H), 3.02 and 2.90 (s+s, 3H); 1.90-1.20 (m, 8H) and 1.31 ppm (s, 3H).

EXAMPLE 46 and EXAMPLE 47

N-(cis-4-Hydroxy-4-ethylcyclohexyl)-N-methyl-[2,1,3]-benzoxadiazole-5-carboxamide and N-(trans-4-hydroxy-4-ethylcyclohexyl)-N-methyl-[2,1,3]-benzoxadiazole-5-carboxamide

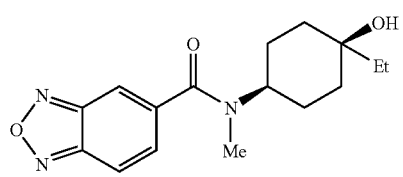

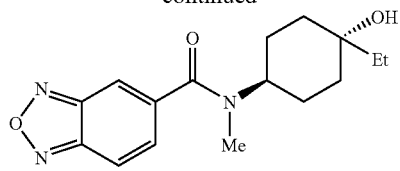

These compounds were prepared using the methods described for Examples 44 and 45 using ethyl magnesium bromide.

N-(cis-4-Hydroxy-4-ethylcyclohexyl)-N-methyl-[2,1,3]-benzoxadiazole-5-carboxamide was isolated as a white solid. Mp=145-146° C., ¹H NMR (300 MHz, CDCl₃) δ 7.91 (d, J=9.0 Hz, 1H), 7.82 (sb, 1H); 7.46-7.37 (m, 1H); 4.60-4.45 and 3.50-3.30 (m, 1H), 3.05 and 2.91 (s+s, 3H) and 2.10-0.80 ppm (m, 13H).

N-(trans-4-Hydroxy-4-ethylcyclohexyl)-N-methyl-[2,1,3]-benzoxadiazole-5-carboxamide was isolated as a white solid. Mp=110-111° C., ¹H NMR (300 MHz, CDCl₃) δ 7.92 (d, J=9.0 Hz, 1H), 7.82 (s, 1H); 7.40 (d, J=9.0 Hz, 1H); 4.60-4.45 and 3.60-3.40 (m, 1H), 3.00 and 2.89 (s+s, 3H) and 1.95-0.90 ppm (m, 13H).

EXAMPLE 48

N-(cis-4-Ethynyl-4-hydroxycyclohexyl)-N-methyl-[2,1,3]-benzoxadiazole-5-carboxamide

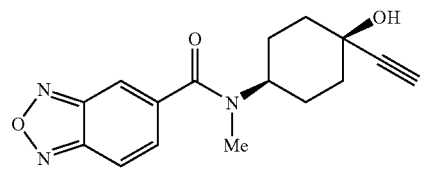

Prepared using the methods described for Examples 44 and 45 using ethynyl magnesium bromide and isolated as a white solid. Mp=160-161° C., ¹H NMR (300 MHz, CDCl₃) δ 7.92 (d, J=9.0 Hz, 1H), 7.83 (sb, 1H); 7.46-7.36 (m, 1H); 4.65-4.50 and 3.60-3.40 (m, 1H), 3.03 and 2.90 (s+s, 3H); 2.60 (s, 1H) and 2.30-1.35 ppm (m, 8H).

EXAMPLE 49 and EXAMPLE 50

N-(cis-4-But-3-en-1-yl-4-hydroxycyclohexyl)-N-methyl-[2,1,3]-benzoxadiazole-5-carboxamide and N-(trans-4-but-3-en-1-yl-4-hydroxycyclohexyl)-N-methyl-[2,1,3]-benzoxadiazole-5-carboxamide

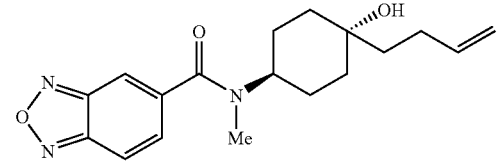

-continued

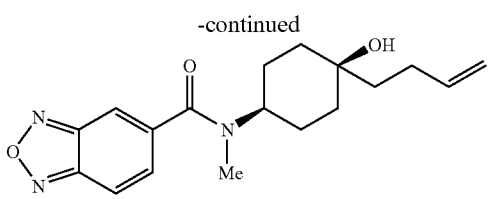

Title compounds were prepared using the methods described for Examples 44 and 45 using but-3-en-1-yl magnesium bromide.

N-(cis-4-But-3-en-1-yl-4-hydroxycyclohexyl)-N-methyl-[2,1,3]-benzoxadiazole-5-carboxamide was isolated as a white solid. Mp=143-144° C., $^1$H NMR (300 MHz, CDCl$_3$) δ 7.91 (d, J=9.3 Hz, 1H), 7.82-7.79 (m, 1H); 7.46-7.37 (m, 1H); 5.95-5.70 (m, 1H); 5.15-4.90 (m, 2H); 4.60-4.45 and 3.50-3.30 (m, 1H), 3.05 and 2.91 (s+s, 3H) and 2.60-1.10 ppm (m, 12H).

N-(trans-4-But-3-en-1-yl-4-hydroxycyclohexyl)-N-methyl-[2,1,3]-benzoxadiazole-5-carboxamide was isolated as a white solid. Mp=145-146° C., $^1$H NMR (300 MHz, CDCl$_3$) δ 7.92 (d, J=9.0 Hz, 1H), 7.82 (s, 1H); 7.40 (d, J=9.0 Hz, 1H); 5.95-5.80 (m, 1H); 5.12-4.98 (m, 2H); 4.60-4.45 and 3.60-3.40 (m, 1H), 3.01 and 2.90 (s+s, 3H) and 2.25-1.20 ppm (m, 12H).

EXAMPLE 51

N-(4-trans-Hydroxycyclohexyl)-N-methyl-[2,1,3]-benzoxadiazole-5-carboxamide

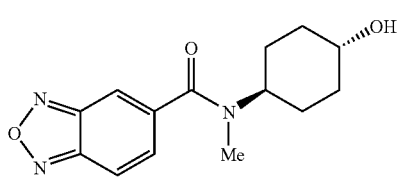

Trans-4-aminocyclohexanol hydrochloride (60.6 g, 0.40 mol) and NaHCO$_3$ (140 g) were dissolved in water (700 ml). Ethyl acetate (500 ml) was added and the mixture stirred rapidly using a mechanical stirrer whilst a solution of ethyl chloroformate (48 ml) in ethyl acetate (200 ml) was added slowly. The mixture was stirred overnight and then ethyl acetate (1 l) and water (500 ml) were added to dissolve the precipitate. The aqueous was extracted with ethyl acetate (2×500 ml) and the combined organic phases were washed with 2N HCl, dried over Na$_2$SO$_4$, and the solvent evaporated, to give a white solid (73.7 g). This material was dissolved in dry THF (600 ml) and the solution slowly (~1 h) added to a suspension of LiAlH$_4$ (29.6 g) in THF (600 ml). After stirring overnight at 20° C. the mixture was cooled in an ice bath and a solution of sodium hydroxide (77 g) in water (50 ml) was slowly added. After 1 h, some celite was added and the mixture was filtered and washed with dichloromethane. The filtrate was dried (MgSO$_4$) and evaporated under vacuum to give trans-4-methylaminocyclohexanol a white solid (45.9 g).

trans-4-Methylaminocyclohexanol (37.1 g, 0.28 mol), [2,1,3]-benzoxadiazole-5-carboxylic acid (42.7 g, 0.26 mol), DMAP (32 g, 0.26 mol), HOBT (11 g, 0.08 mol) and triethylamine (54 ml) were dissolved in dichloromethane (750 ml) and after 15 minutes, EDCI (100 g, 0.52 mol) was added and the mixture refluxed for 2 h. The mixture was washed with 2N HCl (500 ml) and NaHCO$_3$ solution (500 ml), dried over MgSO$_4$ and then concentrated under vacuum. The residue was chromatographed on silica gel using ethyl acetate/chloroform (3:1) as eluant to is give the title product as a white solid (37 g) after trituration with ethyl acetate. Mp=170-171° C., LC-MS, MH$^+$=276; $^1$H NMR (300 MHz, CDCl$_3$, rotamers) δ 7.92 (d, J=9.0 Hz, 1H); 7.82 (s, 1H); 7.40 (d, J=9.0 Hz, 1H); 4.60-4.40 and 3.70-3.40 (m, 2H); 2.99 and 2.87 (s+s, 3H); 2.20-1.05 ppm (s, 8H).

EXAMPLE 52

N-(4-trans-Hydroxycyclohexyl)-N-D$_3$-methyl-[2,1,3]-benzoxadiazole-5-carboxamide

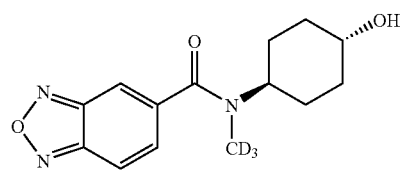

Title compound was prepared using the procedure described for Example 51 replacing LiAlD$_4$ for LiAlH$_4$. Mp=170-171° C., $^1$H NMR (300 MHz, CDCl$_3$, rotamers) δ 7.92 (d, J=9.0 Hz, 1H); 7.82 (s, 1H); 7.40 (d, J=9.0 Hz, 1H); 4.60-4.40 and 3.70-3.40 (m, 2H) and 2.20-1.05 ppm (s, 8H).

EXAMPLE 53

N-(trans-4-Methoxycyclohexyl)-N-methyl-[2,1,3]-benzoxadiazole-5-carboxamide

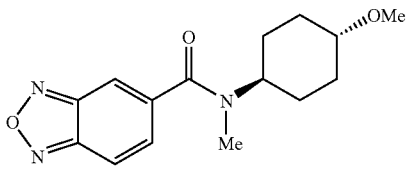

Sodium hydride (0.12 g, 4.8 mmol) followed by methyl iodide (1.1 ml) were added to a solution of N-(4-trans-hydroxycyclohexyl)-N-methyl-[2,1,3]-benzoxadiazole-5-carboxamide (0.55 g, 2.0 mmol), in DMF (5 ml), and the mixture stirred at 40° C. for 2 h. The DMF was evaporated and the residue was chromatographed on silica gel eluting with ethyl acetate/chloroform (3:1) to give a white solid (0.42 g). Mp=143-144° C., NMR (300 MHz, CDCl$_3$, rotamers) δ 7.92 (d, J=9.0 Hz, 1H); 7.82 (s, 1H); 7.40 (d, J=9.0 Hz, 1H); 4.60-4.40 and 3.60-3.00 (m, 2H); 3.37 and 3.29 (s+s, 3H); 2.99 and 2.88 (s+s, 3H); 2.30-0.95 ppm (s, 8H).

EXAMPLE 54

N-(trans-4-Methoxycyclohexyl)-N-methyl-[2,1,3]-benzoxadiazole-5-carbothioamide

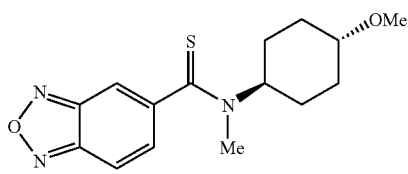

N-(trans-4-Methoxycyclohexyl)-N-methyl-[2,1,3]-benzoxadiazole-5-carboxamide (0.91 g, 3.2 is mmol) and phosphorus pentasulfide (1.42 g) were refluxed in toluene (40 ml) for 3 h. The mixture was cooled, filtered through a 2 cm layer of silica gel and washed with dichloromethane. Evaporation of the solvent and trituration with diethyl ether gave a yellow solid (0.11 g). Mp=137-138° C., $^1$H NMR (300 MHz, CDCl$_3$, rotamers) δ 7.89-7.83 (m, 1H); 7.58-7.55 (m, 1H); 7.36-7.30 (m, 1H); 5.50-5.40 and 3.90-3.75 and 3.50-3.00 (m, 2H); 3.44 and 3.38 (s+s, 3H); 3.27 and 3.04 (s+s, 3H); 2.30-0.95 ppm (s, 8H).

EXAMPLE 55

N-(4-cis-Hydroxycyclohexyl)-N-methyl-[2,1,3]-benzoxadiazole-5-carboxamide

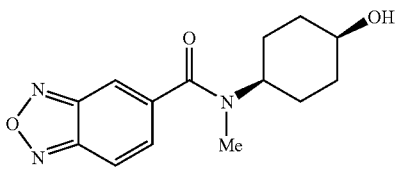

N-(4-trans-Hydroxycyclohexyl)-N-methyl-[2,1,3]-benzoxadiazole-5-carboxamide (1.26 g, 4.57 mmol), 4-nitrobenzoic acid (1.50 g, 9 mmol) and triphenyl phosphine (2.36 g, 9 mmol) were dissolved in THF (60 ml). A solution of diethylazodicarboxylate (DIAD, 1.82 g, 9 mmol) in THF (3 ml) was added slowly and the mixture stirred overnight. The mixture was washed with NaHCO$_3$ solution (100 ml), the aqueous extracted with ethyl acetate (2×100 ml), dried over Na$_2$SO$_4$ and concentrated. The residue was purified on a silica gel column using ethyl acetate/hexane (3:1 →1:1) as eluant to give the 4-nitrobenzoate ester as a white solid (1.4 g). This material was suspended in anhydrous methanol (150 ml) and a solution of sodium (0.4 g) in anhydrous methanol (50 ml) was added. After stirring at 20° C. for 1 h, the mixture was acidified with conc. HCl and evaporated onto silica gel (10 g). The crude product was chromatographed on silica gel eluting with chloroform/THF/methanol (80:17:3) to give a white solid after crystallization from dichloromethane/MTBE (0.67 g). Mp=177-179° C., LC-MS, MH$^+$=276; $^1$H NMR (300 MHz, CDCl$_3$, rotamers) δ 7.91 (d, J=9.6 Hz, 1H); 7.82 (s, 1H); 7.40 (d, J=9.6 Hz, 1H); 4.65-4.48 and 4.17-3.92 and 3.55-3.37 (m, 2H); 3.05 and 2.91 (s+s, 3H); 2.22-1.25 ppm (s, 8H).

EXAMPLE 56

N-Methyl-N-[trans-4-(2H-tetrazol-2-yl)cyclohexyl]-[2,1,3]-benzoxadiazole-5-carboxamide

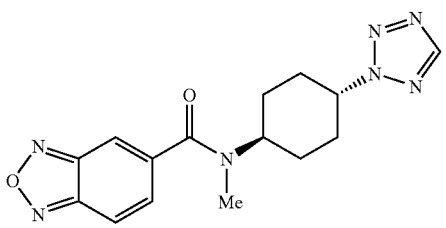

N-(4-cis-Hydroxycyclohexyl)-N-methyl-[2,1,3]-benzoxadiazole-5-carboxamide (0.28 g, 1.0 mmol), 1H-tetrazole (0.14 g. 2 mmol) and triphenyl phosphine (0.52 g, 2 mmol) were dissolved in THF (25 ml) and a solution of DIAD (0.40 g, 2 mmol), in THF (5 ml), was added slowly and the mixture stirred for 3 h. The mixture was evaporated under vacuum and the residue was purified on a silica gel column using ethyl acetate/hexane/chloroform (35:50:15) as eluant, followed by chromatography eluting with toluene/acetone (80:20), to give a white crystalline product after crystallization from dichloromethane/MTBE/hexane (0.06 g). Mp=172-175° C., $^1$H NMR (300 MHz, CDCl$_3$, rotamers) δ 8.49 (sb, 1H), 7.94 (d, J=9.3 Hz, 1H); 7.86 (s, 1H); 7.43 (d, J=9.3 Hz, 1H); 4.85-4.60 and 3.75-3.60 (m, 2H); 3.10-2.90 (m, 3H); 2.50-1.80 ppm (s, 8H).

EXAMPLE 57

N-(trans-4-Azidocyclohexyl)-N-methyl-[2,1,3]-benzoxadiazole-5-carboxamide

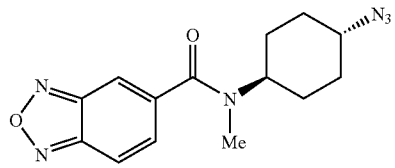

To a cooled (−25° C.) solution of N-(4-cis-hydroxycyclohexyl)-N-methyl-[2,1,3]-benzoxadiazole-5-carboxamide (0.55 g, 2.0 mmol), diphenylphosphorylazide (2.2 ml, 10 mmol) and triphenyl phosphine (2.62 g, 10 mmol), in THF (50 ml), was slowly added a solution of DIAD (2.0 ml, 10 mmol), in THF (5 ml), and the mixture stirred for 2 h at −25° C. and for 3 h at 20° C. Water (40 ml) was added and extracted with ethyl acetate (2×100 ml). The combined organics were dried over MgSO$_4$, concentrated under vacuum, and the residue chromatographed on silica gel eluting with ethyl acetate/hexane/chloroform (2:1:1) to give the product as a white solid after trituration with diethyl ether (0.29 g). Mp=149-150° C., $^1$H NMR (300 MHz, CDCl$_3$, rotamers) δ 7.92 (d, J=9.3 Hz, 1H); 7.82 (s, 1H); 7.40 (d, J=9.3 Hz, 1H); 4.60-4.40 and 3.60-3.10 (m, 2H); 2.99 and 2.88 (s+s, 3H); 2.20-1.10 ppm (s, 8H).

EXAMPLE 58

N-(trans-4-Aminocyclohexyl)-N-methyl-[2,1,3]-benzoxadiazole-5-carboxamide

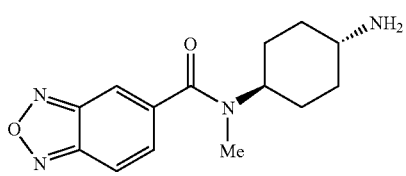

N-(trans-4-Azidocyclohexyl)-N-methyl-[2,1,3]-benzoxadiazole-5-carboxamide (0.18 g, 0.6 mmol) was dissolved in pyridine (4 ml), Ph$_3$P (0.26 g, 1.0 mmol) was added, and the mixture stirred for 1 hour at room temperature. Conc. ammonia solution (6 ml) was slowly added and the mixture stirred for 2 h at 20° C. before evaporating under vacuum and purifying the crude product on silica gel, eluting with chloroform/methanol/triethylamine (90:10:1), to give a white solid after trituration with diethyl ether (0.067 g). Mp=145-146° C., $^1$H NMR (300 MHz, DMSO+CDCl$_3$, rotamers) δ 7.93 (d, J=8.7 Hz, 1H); 7.82 (s, 1H); 7.41 (d, J=8.7 Hz, 1H); 4.60-4.50 and 3.55-3.35 and 2.80-2.55 (m, 2H); 3.00 and 2.88 (s+s, 3H); 2.10-0.90 ppm (s, 8H).

EXAMPLE 59 and EXAMPLE 60

N-(cis-3-Hydroxycyclohexyl)-N-methyl-[2,1,3]-benzoxadiazole-5-carboxamide and N-(trans-3-hydroxycyclohexyl)-N-methyl-[2,1,3]-benzoxadiazole-5-carboxamide

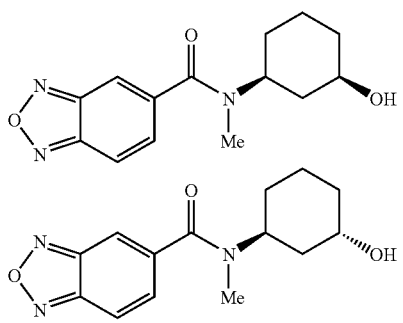

The title compounds were prepared from benzyl (3-oxocyclohexyl)carbamate using the procedures described for Example 51. The cis- and trans-isomers were separated by silica gel chromatography eluting with ethyl acetate/chloroform (3:1). Less polar isomer, mp=159-160° C., $^1$H NMR (300 MHz, CDCl$_3$, rotamers) δ 7.90 (d, J=9.3 Hz, 1H); 7.83 (s, 1H); 7.41 (d, J=9.3 Hz, 1H); 4.95-4.80 and 4.37-3.95 (m, 2H); 2.99 and 2.87 (s+s, 3H); 2.20-1.25 ppm (s, 8H). More polar isomer, mp=131-132° C., $^1$H NMR (300 MHz, CDCl$_3$, rotamers) δ 7.92 (d, J=9.0 Hz, 1H); 7.83 (s, 1H); 7.41 (d, J=9.0 Hz, 1H); 4.65-4.50 and 3.90-3.37 (m, 2H); 3.02 and 2.89 (s+s, 3H); 2.20-1.00 ppm (s, 8H).

EXAMPLE 61

N-Methyl-N-(3-oxocyclohexyl)-[2,1,3]-benzoxadiazole-5-carboxamide

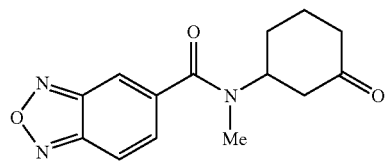

N-(3-Hydroxycyclohexyl)-N-methyl-[2,1,3]-benzoxadiazole-5-carboxamide (0.38 g, 1.38 mmol) was dissolved in dichloromethane (10 ml) and PCC (3 g) was added and the mixture stirred for 3 h at 20° C. The solvent was evaporated onto silica gel and the product chromatographed on silica gel eluting with ethyl acetate/chloroform (3:1) to give the title product as a white solid after trituration with diethyl ether (0.19 g). Mp=164-165° C., $^1$H NMR (300 MHz, CDCl$_3$, rotamers) δ 7.93 (d, J=9.3 Hz, 1H); 7.84 (s, 1H); 7.40 (d, J=9.3 Hz, 1H); 4.90-4.67 and 4.00-3.75 (m, 1H); 3.00 (sb, 3H); 2.71-1.30 ppm (s, 8H).

EXAMPLE 62

N-Methyl-N-(3,3-difluorocyclohexyl)-[2,1,3]-benzoxadiazole-5-carboxamide

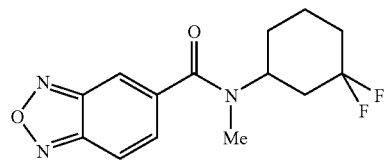

Prepared using the methods described for the preparation of Example 40. Mp=119-120° C., $^1$H NMR (300 MHz, CDCl$_3$, rotamers) δ 7.93 (d, J=9.0 Hz, 1H); 7.84 (s, 1H); 7.41 (d, J=9.0 Hz, 1H); 4.80-4.60 and 3.85-3.70 (m, 1H); 2.94 (sb, 3H); 2.40-1.25 ppm (s, 8H).

EXAMPLE 63

N-(2-Hydroxycyclohexyl)-N-methyl-[2,1,3]-benzoxadiazole-5-carboxamide

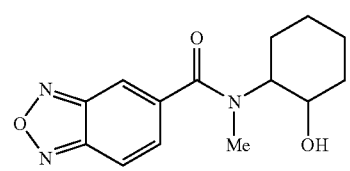

Prepared from benzyl (2-oxocyclohexyl)carbamate using the procedures described for Example 51. Only one isomer was observed. Mp=148-149° C., $^1$H NMR (300 MHz, CDCl$_3$, rotamers) δ 7.92-7.86 (m, 2H); 7.51-7.46 (m, 1H); 4.50-4.38 and 3.75-3.35 (m, 2H); 3.05 and 2.94 (s+s, 3H); 2.42-1.00 ppm (s, 8H).

EXAMPLE 64

N-Methyl-N-(2-oxocyclohexyl)-[2,1,3]-benzoxadiazole-5-carboxamide

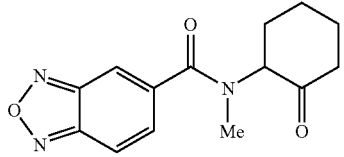

Prepared from N-(2-hydroxycyclohexyl)-N-methyl-[2,1,3]-benzoxadiazole-5-carboxamide using the method described from Example 61. Mp=144-145° C., $^1$H NMR (300 MHz, CDCl$_3$, rotamers) δ 7.94-7.74 (m, 2H); 7.53-7.30 (m, 1H); 5.30-5.20 and 4.20-4.10 (m, 1H); 3.04 and 2.94 (s+s, 3H); 2.62-1.50 ppm (s, 8H).

EXAMPLE 65

N-Methyl-N-(2,2-difluorocyclohexyl)-[2,1,3]-benzoxadiazole-5-carboxamide

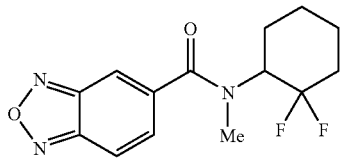

Prepared using the methods described for the preparation of Example 40. Mp=101-102° C., $^1$H NMR (300 MHz, CDCl$_3$, rotamers) δ 7.95-7.77 (m, 2H); 7.48 (m 1H); 5.10-4.90 and 3.80-3.60 (m, 1H); 3.17 and 3.03 (s+s, 3H); 2.30-1.10 ppm (s, 8H).

EXAMPLE 66 and EXAMPLE 67

N-(2-Hydroxytetrahydro-2H-pyran-4-yl-[2,1,3]-benzoxadiazole-5-carboxamide and N-(2-oxotetrahydro-2H-pyran-4-yl)-[2,1,3]-benzoxadiazole-5-carboxamide

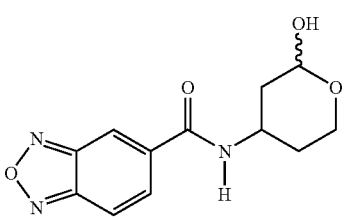

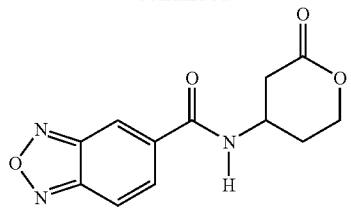

To a solution of 3-aminopentane-1,5-diol (2.38 g, 20 mmol) (*Helv. Chim. Acta* 1964, 47(8), 2145-2153) and triethylamine (4 ml), in dichloromethane (30 ml), was slowly added, at 0° C., a solution of [2,1,3]-benzoxadiazole-5-carboxylic acid chloride (1.82 g, 10 mmol), in dichloromethane (20 ml), and the mixture stirred for 1 h. A mixture of methanol (30 ml) and 4N potassium carbonate solution (20 ml) was added and stirred for 3 h. The mixture was evaporated onto silica gel and purified by silica gel chromatography eluting with ethyl acetate/chloroform/methanol (60:30:10) to give, after crystallization from dichloromethane/ethyl acetate/diethyl ether, N-(1,5-dihydroxypentan-3-yl)-[2,1,3]-benzoxadiazole-5-carboxamide as a white solid (Mp: 87-88° C.). N-(1,5-Dihydroxypentan-3-yl)-[2,1,3]-benzoxadiazole-5-carboxamide (0.5 g, 1.9 mmol), suspended in chloroform (20 ml), was warmed to 45° C. and periodinane (Dess Martin reagent; 1.6 g) added and stirred for 1 h. The reaction mixture was evaporated onto silica gel and purified by chromatography, eluting with ethyl acetate/chloroform (60:40) to give N-(2-hydroxytetrahydro-2H-pyran-4-yl)-[2,1,3]-benzoxadiazole-5-carboxamide (0.12 g) as a white solid after trituration with diethyl ether and as the less polar of two components (Rf: 0.55). Mp=91-92° C., $^1$H NMR (300 MHz, CDCl$_3$) δ 8.22 (s, 1H); 7.96-7.81 (m, 2H); 7.10-7.00 and 6.40-6.05 (m, 2H); 4.65-4.40 (m, 1H); 4.15-3.70 (m, 2H) and 2.15-0.60 ppm (m, 4H).

The more polar component (Rf: 0.45; 0.035 g) was identified as N-(2-oxotetrahydro-2H-pyran-4-yl)-[2,1,3]-benzoxadiazole-5-carboxamide. Mp=157-158° C., $^1$H NMR (300 MHz, CDCl$_3$) δ 8.42-8.36 (m, 1H); 7.95-7.86 (m, 2H); 7.74-7.66 (m, 1H); 4.77-4.36 (m, 3H); 3.02 (dd, J=7.2 and 17.7 Hz, 1H); 2.72 (dd, J=4.5 and 17.7 Hz, 1H) and 2.38-2.07 ppm (m, 2H).

EXAMPLE 68

N-Methyl-N-(2-oxotetrahydro-2H-pyran-4-yl)-[2,1,3]-benzoxadiazole-5-carboxamide

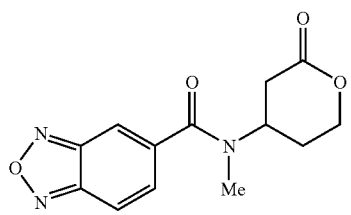

5,6-Dihydro-2H-pyran-2-one (1.0 g, 10.2 mmol) was dissolved in 3 ml of a 33% solution of methylamine in ethanol and heated to 55° C. overnight. The solvent was evaporated, the residue dissolved in methanol (20 ml) and conc. HCl (20 ml) and the mixture heated at 95° C. for 2.5 h. The mixture was evaporated to dryness, the residue dissolved in THF (20 ml), dichloromethane (20 ml) and triethylamine (3 ml) and a solution of [2,1,3]-benzoxadiazole-5-carboxylic acid chloride (2.0 g, 11 mmol), in dichloromethane (5 ml), added. After stirring is the mixture for 0.75 h, the mixture was washed with 1N HCl and conc. NaHCO₃ solution, dried over sodium sulfate, and concentrated under vacuum. The residue was purified on a silica gel column using ethyl acetate/hexane/dichloromethane (70:20:10), to give N-methyl-N-(2-oxotetrahydro-2H-pyran-4-yl)-[2,1,3]-benzoxadiazole-5-carboxamide as white solid after crystallization from dichloromethane/methanol (0.21 g). Mp=169-171° C., ¹H NMR (300 MHz, CDCl₃, rotamers) δ 7.97 (d, J=9.0 Hz, 1H); 7.90 (s, 1H); 7.40 (d, J=9.0 Hz, 1H); 5.10-4.40 (m, 3H); 3.01 (s, 3H); 3.00-2.74 (m, 2H) and 2.60-2.10 ppm (s, 2H).

EXAMPLE 69

N-(2-Hydroxytetrahydro-2H-pyran-4-yl)-N-methyl-[2,1,3]-benzoxadiazole-5-carboxamide

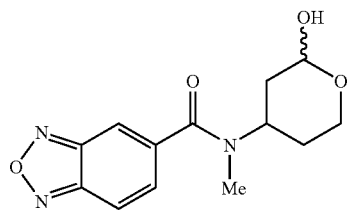

To a suspension of N-(1,5-dihydroxypentan-3-yl)-[2,1,3]-benzoxadiazole-5-carboxamide (see Example 66; 0.9 g, 3.4 mmol), in chloroform (20 ml), was added a solution of acetic anhydride (3 ml) and pyridine (3 ml), drop wise, at room temperature and the mixture stirred for 2 h. Chloroform (50 ml) was added and the mixture washed with 1N HCl and saturated sodium bicarbonate solution, dried (MgSO₄) and evaporated. The residue was chromatograhed on silica gel, eluting with ethyl acetate/chloroform (3:2), to give N-(1,5-diacetoxypentan-3-yl)-[2,1,3]-benzoxadiazole-5-carboxamide as a pale yellow solid.

To a solution of preceding di-acetate (2.4 g, 6.8 mmol), in DMF (40 ml), was added sodium hydride (0.49 g, 20 mmol) and the mixture stirred at room temperature for 0.25 h. Methyl iodide (1.0 ml) was added, the mixture heated at 60° C. for 0.5 h and the solvent evaporated. The residue was dissolved in chloroform (100 ml), washed with 1N HCl and saturated sodium bicarbonate solution, dried (MgSO₄) and evaporated. The residue was chromatograhed on silica gel to give N-(1,5-diacetoxypentan-3-yl)-N-methyl-[2,1,3]-benzoxadiazole-S-carboxamide as a pale brown oil.

To a solution of N-(1,5-diacetoxypentan-3-yl)-N-methyl-[2,1,3]-benzoxadiazole-5-carboxamide (1.37 g, 3.8 mmol), in methanol (10 ml), was added 10 ml of 3N potassium carbonate solution and the mixture stirred at room temperature for 2 h. The methanol was evaporated under vacuum and the residue dissolved in chloroform (100 ml), washed with 1N HCl and saturated sodium bicarbonate solution, dried (MgSO₄) and evaporated. The crude product was chromatographed on silica gel eluting with ethyl acetate/chloroform/methanol (1:1:8%) to give the diol as a pale yellow solid after trituration with diethyl ether (0.42 g). Mp=90-91° C.

N-(1,5-Dihydroxypentan-3-yl)-N-methyl-[2,1,3]-benzoxadiazole-5-carboxamide was reacted with periodinane as described for Examples 66 and 67 to give N-(2-hydroxytetrahydro-2H-pyran-4-yl)-N-methyl-[2,1,3]-benzoxadiazole-5-carboxamide as a pale yellow solid. Mp=<90° C., ¹H NMR (300 MHz, CDCl₃) δ 7.92 (d, J=9 Hz, 1H); 7.85 (s, 1H), 7.41 (d, J=9 Hz, 1H); 6.40-6.05 (m, 1H); 5.20-4.75 (m, 1H); 4.20-3.60 (m, 3H), 3.10-2.80 (m, 3H), and 2.25-1.50 ppm (m, 4H).

EXAMPLE 70 trans-4-[(2,1,3-Benzoxadiazol-5-ylcarbonyl)(methyl)amino]cyclohexyl N,N-dimethyl glycinate hydrochloride

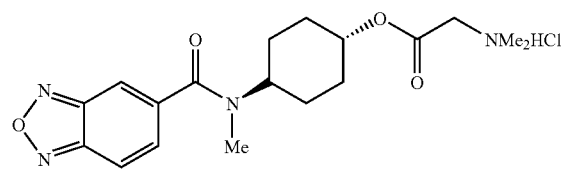

To a solution of N-(4-trans-hydroxycyclohexyl)-N-methyl-[2,1,3]-benzoxadiazole-5-carboxamide (0.55 g, 2.0 mmol) in DMF (10 ml) was added N,N-dimethyl glycine (0.52 g, 5.0 mmol), DMAP (0.244 g, 2.0 mmol), HOBT (0.27 g, 2.0 mmol) and EDCI (1.15 g, 6.1 mmol) and the mixture heated at 45° C. overnight. The solvent was evaporated under vacuum and the residue dissolved in chloroform (100 ml) washed with water, dried (MgSO₄) and evaporated. The crude product was chromatographed on silica gel eluting with ethyl acetate/chloroform/methanol (1:1:10%) to give as a white solid, mp=174-175° C. The product was dissolved in 4N HCl in dioxane and then evaporated to dryness to give the hydrochloride salt. Mp=252-253° C., ¹H NMR (300 MHz, D₂O, 2-rotamers) δ 8.03-7.99 (m, 2H), 7.52-7.49 (m, 1H), 4.43-4.34 (m, 0.5H), 4.10 and 4.03 (s, 3H), 3.60-3.40 (m, 0.5H), 3.02-2.91 (m, 9H), and 2.22-1.20 ppm (m, 8H).

EXAMPLE 71 trans-4-[(2,1,3-Benzoxadiazol-5-ylcarbonyl)(methyl)amino]cyclohexyl L-alaninate hydrochloride

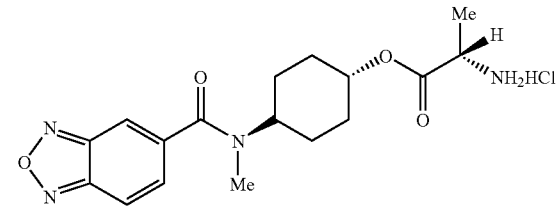

To a solution of N-(tert-butoxycarbonyl)-L-alanine (0.38 g, 2.0 mmol) in chloroform (20 ml) was added CDI (0.32 g, 2 mmol) and the mixture stirred at room temperature for 1.5 h. N-(4-trans-Hydroxycyclohexyl)-N-methyl-[2,1,3]-benzoxadiazole-5-carboxamide (0.55 g, 2.0 mmol) was added and the mixture stirred overnight. Water (50 ml) was added and sulfuric-acid (→pH 2) and extracted with dichloromethane (2×70 ml). The combined organics was washed with sodium bicarbonate solution (50 ml), dried (NaSO₄) and evaporated. The residue was chromatographed on silica gel eluting with ethyl acetate/hexane (70:30) to give the product as a foam (0.55 g). This material was dissolved in chloroform (20 ml), TFA (3 ml) added, and the mixture stirred for 1 h. The solvent was evaporated and chloroform (30 ml) and 4N HCl in dioxane (3 ml) were added. The solvent was evaporated to give the title compound as a colorless oil that solidified on standing to give a low melting solid (0.59 g). ¹H NMR (300 MHz, D₂O, 2-rotamers) δ 8.03-7.98 (m, 2H), 7.52-7.49 (m, 1H), 4.94-4.64 (m, 1H), 4.43-4.34 (m, 0.5H), 4.20-4.10 and 4.10-4.00 (q, J=7.2 Hz, 1H), 3.60-3.44 (m, 0.5H), 3.01 and 2.90 (s, 3H), and 2.20-1.20 (m, 8H), 1.55 and 1.45 ppm (d, J=7.2 Hz, 3H).

EXAMPLE 72

N—(R)-Tetrahydrofuran-3-yl-[2,1,3]-benzoxadiazole-5-carboxamide

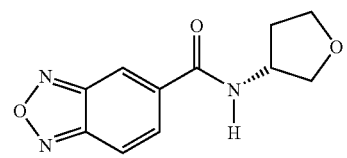

Prepared from Intermediate 2 and (R)-(+)-tetrahydro-3-furylamine p-toluenesulphonate in a similar manner to that described for the preparation of Example 1. The title compound was isolated as a white solid following re-crystallization from diethyl ether/ethyl acetate. Mp=157-158° C., ¹H NMR (300 MHz, CDCl₃) δ 8.20 (s, 1H), 7.92 (dd, J=1.2 and 9.3 Hz, 1H), 7.82 (dd, J=1.2 and 9.3 Hz, 1H), 6.48 (br s, 1H), 4.60-4.64 (m, 1H), 4.10-3.80 (m, 4H), 2.50-2.38 (m, 1H), 2.03-1.94 ppm (m, 1H).

EXAMPLE 73

N-Methyl-N—(R)-tetrahydrofuran-3-yl-[2,1,3]-benzoxadiazole-5-carboxamide

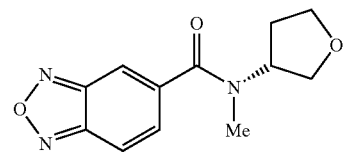

Prepared from N—(R)-tetrahydrofuran-3-yl-[2,1,3]-benzoxadiazole-5-carboxamide using the method described for Example 16. The title compound was isolated as a pale yellow oil. ¹H NMR (300 MHz, CDCl₃, rotamers) δ 7.93 (d, J=9.3 Hz, 1H), 7.84 (s, 1H), 7.42 (d, J=9.3 Hz, 1H), 5.5-5.25 (m, 0.5H), 4.56-4.30 (m, 0.5H), 4.18-3.5 (m, 4H), 3.16-2.90 (br s, 3H), 2.52-1.90 ppm (m, 2H).

EXAMPLE 74 trans-4-[(2,1,3-Benzoxadiazol-5-ylcarbonyl)(methyl)amino]cyclohexyl glycinate hydrochloride

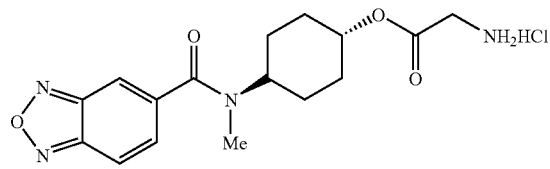

The title compound was prepared from N-(4-trans-hydroxycyclohexyl)-N-methyl-[2,1,3]-benzoxadiazole-5-carboxamide as described for Example 71 and isolated as an off white solid. Mp=245-246° C. (dec), ¹H NMR (300 MHz, D₂O, rotamers) δ 8.05 (d, J=9.3 Hz, 1H), 8.00 (s, 1H), 7.51 (dd, J=2.5 and 9.3 Hz, 1H), 4.98-4.64 (m, 1H), 4.48-4.37 and 3.60-3.44 (m, total 1H), 3.92 and 3.82 (s, total 2H), 3.02 and 2.92 (s, total 3H), 2.03-1.20 ppm (m, 8H).

EXAMPLE 75

N-2-(4-Morpholinyl)ethyl-[2,1,3]-benzoxadiazole-5-carboxamide

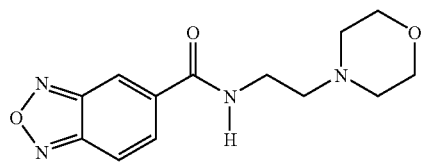

Prepared from Intermediate 1 and 4-(2-aminoethyl)morpholine using the method described for Example 1 and isolated as a white crystalline solid. Mp=145-148° C., ¹H NMR (300 MHz, CDCl₃) δ 8.19 (br s, 1H), 7.93 (dd, J=1.2 and 9.3 Hz, 1H), 7.85 (dd, J=1.5 and 9.3 Hz, 1H), 6.92 (br s, 1H), 3.77-3.73 (m, 4H), 3.62-3.56 (m, 2H), 2.64 (t, J=5.8 Hz, 2H), 2.55-2.51 ppm (m, 4H).

EXAMPLE 76

N-Methyl-N-2-(4-Morpholinyl)ethyl-[2,1,3]-benzoxadiazole-5-carboxamide hydrochloride

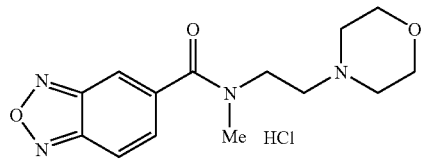

Prepared from N-2-(4-morpholinyl)ethyl-[2,1,3]-benzoxadiazole-5-carboxamide using the method described for Example 16. The hydrochloride salt was isolated as an off white solid. Mp=210-212° C., ¹H NMR (300 MHz, D₂O) δ 8.12 (s, 1H), 8.05 (d, J=9.4 Hz, 1H), 7.59 (d, J=7.4 Hz, 1H), 4.57-4.18 (m, 2H), 4.03 (t, J=6.3 Hz, 2H), 4.00-3.40 (m, 6H), 3.59 (t, J=6.3 Hz, 2H), 3.13 ppm (s, 3H).

EXAMPLE 77

N-Methyl-N-tetrahydro-2H-pyran-4-[2,1,3]-benzoxadiazole-5-carbothioamide

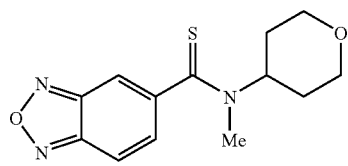

The title compound was prepared from N-methyl-N-tetrahydro-2H-pyran-4-yl-[2,1,3]-benzoxadiazole-5-carboxamide using the procedure described for Example 54 and isolated as a yellow solid. Mp=174-175° C., $^1$H NMR (300 MHz, CDCl$_3$, rotamers) δ 7.89 and 7.86 (dd, J=1.2 and 9.3 Hz, total 1H), 7.58 (d, J=1.2 Hz, 1H), 7.36 and 7.33 (dd, J=1.5 and 9.3 Hz, total 1H), 5.78-5.64 (m, 0.5H), 4.20-3.04 (m, 2.5H), 3.63-3.55 (m, 1H), 3.48 and 3.08 (s, total 3H), 3.20-3.14 (m, 1H), 2.17-1.54 ppm (m, 4H).

EXAMPLE 78 trans-4-[(2,1,3-Benzoxadiazol-5-ylcarbonyl)(methyl)amino]cyclohexyl L-valinate hydrochloride

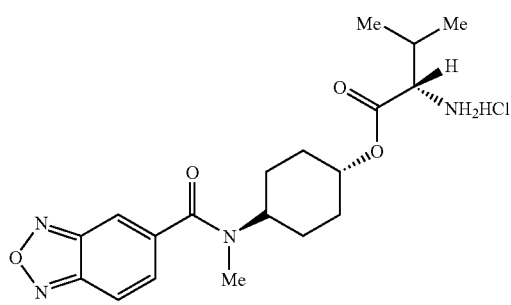

The title compound was prepared from N-(4-trans-hydroxycyclohexyl)-N-methyl-[2,1,3]-benzoxadiazole-5-carboxamide as described for Example 71 and isolated as a white solid. Mp=257-258° C. (dec), $^1$H NMR (300 MHz, D$_2$O, rotamers) δ 8.06-7.93 (m, 2H), 7.53-7.47 (m, 1H), 4.94-4.70 (m, 1H), 4.43-4.35 and 3.60-3.46 (m, total 1H), 4.00 and 3.89 (d, J=3.6 Hz, total 1H), 3.02 and 2.91 (s, total 3H), 2.43-1.62 (m, 8H), 1.40-1.20 (m, 1H), 1.10-0.92 ppm (m, 6H).

EXAMPLE 79 trans-4-[(2,1,3-Benzoxadiazol-5-ylcarbonyl)(methyl)amino]-1-methylcyclohexyl N,N-dimethyl glycinate hydrochloride

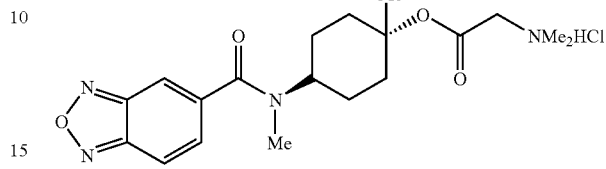

To a solution of N-(trans-4-hydroxy-4-methylcyclohexyl)-N-methyl-[2,1,3]-benzoxadiazole-5-carboxamide (0.7 g, 2.4 mmol) in chloroform (10 ml), at 0° C., was added dimethylaniline (0.44 g, 3.6 mmol) and then chloroacetyl chloride (0.23 ml, 2.9 mmol), and the mixture warmed to room temperature and stirred overnight. The reaction mixture was washed with 1N HCl and sodium bicarbonate solution, dried over MgSO$_4$ and evaporated. The residue was chromatographed on silica gel eluting with ethyl acetate/chloroform (5:2) to give the chloro acetyl adduct. Dimethylamine (3 ml of a 33% solution in methanol) was added to a solution of the preceding product (0.275 g, 0.75 mmol), in chloroform (15 ml), and the mixture stirred at room temperature overnight. The mixture was evaporated and the residue was partitioned between chloroform and water and the organic layer washed with sodium bicarbonate solution, dried (MgSO$_4$) and evaporated. The residue was purified by chromatography on silica gel eluting with ethyl acetate/chloroform/methanol (1:1.5: 7%). The hydrochloride salt was prepared by adding a mixture of 4N HCl in dioxane to a solution of the product in chloroform. The solvents were removed under vacuum and the product re-crystallized from methanol/diethyl ether to give the title compound (0.13 g) as an off white solid. Mp=201-202° C., $^1$H NMR (300 MHz, D$_2$O, 2-rotamers) δ 8.07 (d, J=9.3 Hz, 1H), 8.02 (s, 1H), 7.53 (d, J=9.3 Hz, 1H), 4.45-4.37 and 3.63-3.50 (both m, total 1H), 4.09 and 4.00 (both s, total 2H), 3.05, 3.00, 2.95 and 2.91 (all s, total 9H), 2.40-1.56 (m, 8H), 1.69 and 1.63 ppm (both s, total 3H).

EXAMPLE 80

N-Methyl-N-tetrahydro-2H-pyran-4-ylmethyl-[2,1,3]-benzoxadiazole-5-carboxamide

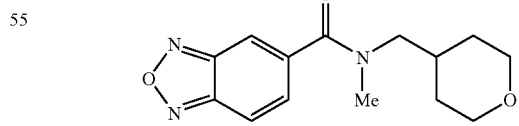

Methyl tetrahydro-2H-pyran-4-carboxylate (5 ml, 40.0 mmol) was added to a solution of methylamine (generated by heating a mixture of methylamine hydrochloride and sodium hydroxide pellets) in THF (30 ml) and the mixture heated at 110° C. in a bomb reactor overnight. The solvents were evaporated, the residue dissolved in THF (100 ml), and LiAlH$_4$ (4.6 g, 121 mmol) added, and the mixture heated at 70° C. for 1 h. The mixture was cooled to 0° C., concentrated NaOH solution added and the THF evaporated. Chloroform (100 ml) was added to the residue and the resulting solid was filtered off and the filtrate concentrated under vacuum to give N-methyl-N-tetrahydro-2H-pyran-4-ylmethylamine as a pale brown oil. The preceding amine (1 g, 7.8 mmol) was dissolved in dichloromethane (50 ml), and triethylamine (4 ml) and [2,1,3]-benzoxadiazole-5-carbonylchloride (1.7 g, 9.3 mmol), as a solution in dichloromethane (20 ml), were added, slowly. The mixture was stirred at room temperature for 1 h, the mixture washed with 1N HCl (20 ml), and saturated sodium bicarbonate solution (20 ml), dried (MgSO$_4$) and evaporated. The residue was purified by silica gel chromatography eluting with ethyl acetate/chloroform (3:1) to give the title compound as a pale brown oil. $^1$H NMR (300 MHz, CDCl$_3$, 2-rotamers) δ 7.93 (d, J=9.3 Hz, 1H), 7.83 (br s, 1H), 7.38-7.45 (m, 1H), 4.10-3.90 (m, 2H), 3.52-3.20 (m, 4H), 3.13 and 3.05 (both s, total 3H), 2.18-1.80 (m, 1H), 1.73-1.40 ppm (m, 4H).

EXAMPLE 81 trans-4-[(2,1,3-Benzoxadiazol-5-ylcarbonyl)(methyl) amino]-1-methylcyclohexyl glycinate hydrochloride

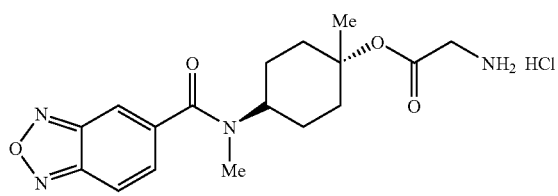

N-(trans-4-Hydroxy-4-methylcyclohexyl)-N-methyl-[2,1,3]-benzoxadiazole-5-carboxamide (0.49 g, 2.0 mmol) was suspended in THF (40 ml) and dimethylaniline (0.3 ml, 2.2 mmol)) was added. The mixture was heated at 70° C. for 0.1 h before adding bromoacetyl bromide (0.2 ml, 2.4 mmol) and stirring at 70° C. for 3 h. The mixture was cooled to room temperature before adding chloroform (50 ml) and washing with water (50 ml), 1 N HCl (25 ml) and saturated sodium bicarbonate solution (25 ml). The organic was dried over MgSO$_4$, evaporated and the residue purified by chromatography on silica gel eluting with ethyl acetate/chloroform (1:1) to give the bromo acetyl derivative as a white solid (0.63 g, 76%; Mp=133-134° C.).

To a solution of the preceding acetyl bromide (0.61 g, 1.5 mmol) in DMF (8 ml) was added sodium azide (0.59 g, 9 mmol) and the mixture heated at 50° C. for 3 h. The DMF was removed under vacuum and the residue partitioned between chloroform and water. The chloroform extract was washed with 1N HCl and saturated sodium bicarbonate solution, dried (MgSO$_4$) and evaporated to give the desired azide. To this material (0.56 g, 1.5 mmol) was added pyridine (5 ml) and triphenyl phosphine (0.63 g, 2.4 mmol) and the mixture stirred at room temperature for 0.5 h) before adding conc$^n$ ammonium hydroxide solution (10 ml) and stirring for a further 2 h at room temperature. The pyridine was removed under vacuum and the residue was purified by chromatography on silica gel eluting with ethyl acetate/hexane (1:1) followed by chloroform/methanol/triethylamine (90:10:3) to give trans-4-[(2,1,3-benzoxadiazol-5-ylcarbonyl)(methyl) amino]-1-methylcyclohexyl glycinate as a yellow solid (0.42 g). The hydrochloride salt was prepared as described previously and was isolated as a white solid. Mp=188-189° C. $^1$H NMR (300 MHz, D$_2$O, 2-rotamers) δ 8.05 (d, J=9.3 Hz, 1H), 7.99 (s, 1H), 7.50 (d, J=9.3 Hz, 1H), 4.45-4.37 and 3.63-3.50 (both m, total 1H), 3.84 and 3.71 (both s, total 2H), 3.03 and 2.93 (both s, total 3H), 2.40-1.56 (m, 8H), 1.66 and 1.59 ppm (both s, total 3H).

II. Biological Methods

EXAMPLE 82

In Vivo Electrophysiology

The electrophysiological effects of invention compounds were tested in vivo in anesthetized animals according to the following procedures.

Animals are maintained under anesthesia by phenobarbital administered using a Hamilton syringe pump. Stimulating and recording electrodes are inserted into the perforant path and dentate gyrus of the hippocampus, respectively. Once electrodes are implanted, a stable baseline of evoked responses are elicited using single monophasic pulses (100 μs pulse duration) delivered at 3/min to the stimulating electrode. Field EPSPs are monitored until a stable baseline is achieved (about 20-30 min), after which a solution of test compound is injected intraperitoneally and evoked field potentials are recorded. Evoked potentials are recorded for approximately 2 h following drug administration or until the amplitude of the field EPSP returns to baseline. In the latter instance, it is common that an iv administration is also carried out with an appropriate dose of the same test compound.

EXAMPLE 83

Inhibition of d-Amphetamine Stimulated Locomotion

Male CD1 mice, 25-30 gm body weight, were brought into the experimental room and allowed at least 30 min of acclimation. Each mouse was placed into the testing enclosure with an infrared beam array that automatically monitors the animal's activity. Mice were habituated in the testing enclosure for 20 min, and then returned to their home cage. Mice were dosed intraperitoneally with test compound in appropriate vehicle 5 minutes before d-Amphetamine injection. Ten minutes after d-Amphetamine injection, mice were tested for locomotor activity for a total of 15 minutes. The data was computer collected and expressed as "arbitrary movement units." All data were analyzed by comparing the groups treated with the test compound to the vehicle control group. Statistical analysis was performed by ANOVA followed by Dunnet's t-test where P less than 0.05 were considered to be significantly different.

While the invention has been described with reference to specific methods and embodiments, it will be appreciated that various modifications may be made without departing from the invention.

What is claimed is:

1. A compound according to the formula:

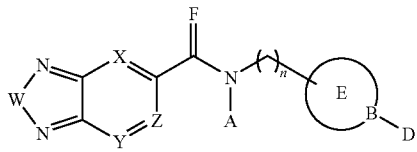

wherein:
W is oxygen;
X, Y and Z are each independently —CR,
wherein:
R is H, —Br, —Cl, —F, —CN, —NO₂, —OR¹, —SR¹, —NR¹₂, —C₁-C₆ branched or un-branched alkyl, which may be un-substituted or substituted,
wherein:
R¹ is H, —C₁-C₆ branched or un-branched alkyl which, may be un-substituted or substituted,
F=O or S,
A is H, or —C₁-C₆ branched or un-branched alkyl, which may be un-substituted or substituted, —C₂-C₆ branched or un-branched alkenyl, which may be un-substituted or substituted, —C₂-C₆ branched or un-branched alkynyl, which may be un-substituted or substituted, —C₃-C₇ cycloalkyl which may be un-substituted or substituted, —C₃-C₇ alkylcycloalkyl which may be un-substituted or substituted, aryl or heterocycle which may be un-substituted or substituted, alkylaryl which may be un-substituted or substituted, alkylheterocycle which may be un-substituted or substituted
n=0, 1, 2, 3, 4, 5, or 6;

is a —C₃-C₇ cycloalkyl which may be un-substituted or substituted, a —C₄-C₇ azacycloalkyl, which may be un-substituted or substituted, a —C₇-C₁₀ bicycloalkyl which may be un-substituted or substituted, a —C₇-C₁₀ azabicycloalkyl which may be un-substituted or substituted, aryl which may be un-substituted or substituted or a heterocycle which may be un-substituted or substituted;
B is —C=, C—Rᵃ, O, N, S, C=O, S=O or SO₂;
Rᵃ is H, a halogen (preferably F), OH, Oalkyl, cyano, or a —C₁-C₆ alkyl group which is un-substituted or substituted and which optionally, forms a C₃-C₇ cycloalkyl group with D; and
D is absent when B is O, S, C=O, S=O or SO₂, or if present, is bonded to B when B is —C=, —C—Rᵃ or N, and is H, a halogen (preferably F), ORᵇ, a —C₁-C₆ branched or un-branched alkyl, which may be un-substituted or substituted and which optionally, forms a C₃-C₇ cycloalkyl group with Rᵃ, a —C₂-C₆ branched or un-branched alkenyl, which may be un-substituted or substituted, a —C₂-C₆ branched or un-branched alkynyl, which may be un-substituted or substituted, a —C₃-C₇ cycloalkyl which may be un-substituted or substituted, an aryl which may be un-substituted or substituted, a heterocycle which may be un-substituted or substituted, a —C₂-C₇ carboxyalkyl which may be un-substituted or substituted, a carboxyaryl which may be un-substituted or substituted, a carboxyheteroaryl which may be un-substituted or substituted, a —C₁-C₇ sulfonylalkyl which may be un-substituted or substituted, a sulfonylaryl which may be un-substituted or substituted or a sulfonylheteroaryl which may be un-substituted or substituted, or when B is —C—Rᵃ, Rᵃ and D optionally form a =N—Rᶜ or a =N—ORᶜ group with B, wherein Rᶜ is H or an un-substituted or substituted C₁-C₇ alkyl group; and
Rᵇ is H, a —C₁-C₇ alkyl group which may be branched or un-branched, un-substituted or substituted or a —C₂-C₇ acyl group which may be un-substituted or substituted;
or a pharmaceutically acceptable salt or pro-drug thereof.

2. Compounds of claim 1 according to formula II:

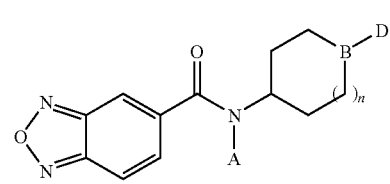

wherein:
A is —C₁-C₆ branched or un-branched alkyl, which may be un-substituted or substituted, a —C₃-C₇ cycloalkyl which may be un-substituted or substituted;
n is 0, 1, 2, or 3; and
B is C—Rᵃ, C=O or O;
Rᵃ is H, OH, alkyl or F; and
D is absent, is H or OH when Rᵃ is H or alkyl, or is F when Rᵃ is F, or a pharmaceutically acceptable salt thereof.

3. Compounds of claim 1 according to formula III:

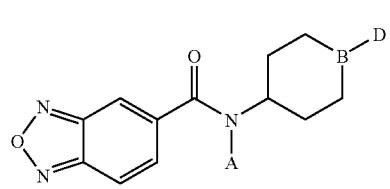

wherein:
A is a C₁-C₆ alkyl which may be substituted or un-substituted
B is C—Rᵃ, O or C=O;
Rᵃ is H, F, —OH or alkyl and
D is absent (when B is O), is H or OH when Rᵃ is H or alkyl, or is F when Rᵃ is F, or a pharmaceutically acceptable salt thereof.

4. Compounds of claim 1 according to formula IV:

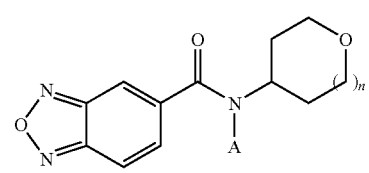

wherein:

A is a $C_1$-$C_6$ alkyl which may be substituted or un-substituted, n is 0, 1 or 2, or a pharmaceutically acceptable salt thereof.

5. Compounds of claim 1 according to formula V:

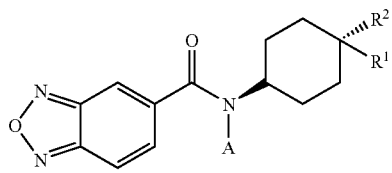

wherein:

A is a $C_1$-$C_6$ alkyl which may be substituted or un-substituted, $R^1$ is H, F, or $C_1$-$C_4$ alkyl, $R^2$ is H, F, CN, a heterocycle which may be substituted or un-substituted or $OR^3$, $R^3$ is H, $C_1$-$C_6$ alkyl which may be substituted or un-substituted, or a pharmaceutically acceptable salt thereof.

6. Compounds of claim 1 according to formula VI:

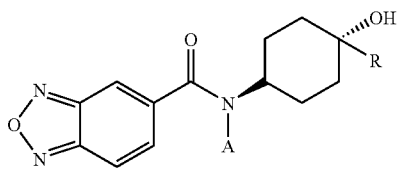

wherein:

A is a $C_1$-$C_6$ alkyl which may be substituted or un-substituted,

R is H, or $C_1$-$C_4$ alkyl, or a pharmaceutically acceptable salt thereof.

7. Compounds of claim 1 according to formula VII:

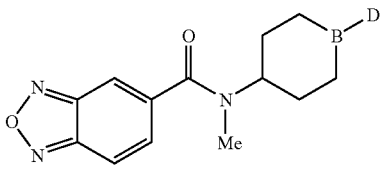

wherein:

B is C—$R^a$, O or C=O;

$R^a$ is H, F, —OH or alkyl and

D is absent (when B is O), is H or OH when $R^a$ is H or alkyl, or is F when $R^a$ is F, or a pharmaceutically acceptable salt thereof.

8. Compounds of claim 1 according to formula VIII:

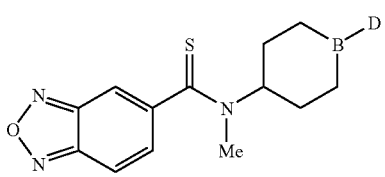

wherein:

B is C—$R^a$, O or C=O;

$R^a$ is H, F, —OH or alkyl and

D is absent (when B is O), is H or OH when $R^a$ is H or alkyl, or is F when $R^a$ is F, or a pharmaceutically acceptable salt thereof.

9. Compounds of claim 1 according to formula IX:

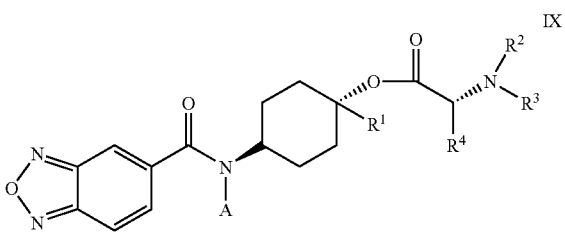

wherein:

A is a $C_1$-$C_6$ alkyl which may be substituted or un-substituted, $R^1$ is H, or $C_1$-$C_4$ alkyl, $R^2$ is H, or a $C_1$-$C_6$ alkyl which may be substituted or un-substituted, $R^3$ is H, or a $C_1$-$C_6$ alkyl which may be substituted or un-substituted, $R^4$ is H, or a $C_1$-$C_6$ alkyl which may be substituted or un-substituted, or a pharmaceutically acceptable salt thereof.

10. A compound according to claim 1 which is:
N-Cyclohexyl-N-methyl-[2,1,3]-benzoxadiazole-5-carboxamide
N-Cyclopentyl-N-methyl-[2,1,3]-benzoxadiazole-5-carboxamide
N-(trans-4-Cyanocyclohexyl)-N-methyl-[2,1,3]-benzoxadiazole-5-carboxamide
N-Methyl-N-tetrahydro-2H-pyran-4-yl-[2,1,3]-benzoxadiazole-5-carboxamide
N-Methyl-N-(4-oxocyclohexyl)-[2,1,3]-benzoxadiazole-5-carboxamide
N-(trans-4-Hydroxy-4-methylcyclohexyl)-N-methyl-[2,1,3]-benzoxadiazole-5-carboxamide or
N-(4-trans-Hydroxycyclohexyl)-N-methyl-[2,1,3]-benzoxadiazole-5-carboxamide.

11. A compound according to Formula IX of claim 9 which is:
trans-4-[(2,1,3-Benzoxadiazol-5-ylcarbonyl)(methyl)amino]cyclohexyl N,N-dimethyl glycinate hydrochloride
trans-4-[(2,1,3-Benzoxadiazol-5-ylcarbonyl)(methyl)amino]cyclohexyl L-alaninate hydrochloride
trans-4-[(2,1,3-Benzoxadiazol-5-ylcarbonyl)(methyl)amino]cyclohexyl L-valinate hydrochloride trans-4-[(2,1,3-Benzoxadiazol-5-ylcarbonyl)(methyl)amino]-1-methylcyclohexyl N,N-dimethyl glycinate hydrochloride
trans-4-[(2,1,3-Benzoxadiazol-5-ylcarbonyl)(methyl)amino]-1-methylcyclohexyl glycinate hydrochloride or
trans-4-[(2,1,3-Benzoxadiazol-5-ylcarbonyl)(methyl)amino]cyclohexyl glycinate hydrochloride.

12. A compound according to claim 1 which is:
N-Cycloheptyl-N-methyl-[2,1,3]-benzoxadiazole-5-carboxamide
N-(4,4-Dimethylcyclohexyl-N-methyl-[2,1,3]-benzoxadiazole-5-carboxamide
N-Methyl-N-spiro[2.5]oct-6-yl-[2,1,3]-benzoxadiazole-5-carboxamide
N-Cyclobutyl-N-methyl-[2,1,3]-benzoxadiazole-5-carboxamide
N-Cyclohexyl-[2,1,3]-benzoxadiazole-5-carboxamide
N-Cyclopentyl-[2,1,3]-benzoxadiazole-5-carboxamide
N-Cyclobutyl-[2,1,3]-benzoxadiazole-5-carboxamide
N-(cis-4-Cyanocyclohexyl)-N-methyl-[2,1,3]-benzoxadiazole-5-carboxamide
N-$D_3$-Methyl-N-tetrahydro-2H-pyran-4-yl-[2,1,3]-benzoxadiazole-5-carboxamide
N-(Tetrahydro-2H-pyran-4-yl)-[2,1,3]-benzoxadiazole-5-carboxamide
N-(Tetrahydro-2H-pyran-3-yl)-[2,1,3]-benzoxadiazole-5-carboxamide
N-Methyl-N-(tetrahydro-2H-pyran-3-yl)-[2,1,3]-benzoxadiazole-5-carboxamide
N-Ethyl-N-tetrahydro-2H-pyran-4-yl-[2,1,3]-benzoxadiazole-5-carboxamide
N-Cyclohexyl-N-ethyl-[2,1,3]-benzoxadiazole-5-carboxamide
N-(Cyclohexylmethyl)-N-methyl-[2,1,3]-benzoxadiazole-5-carboxamide
N-Benzyl-N-methyl-[2,1,3]-benzoxadiazole-5-carboxamide
N-Methyl-N-(tetrahydrofuran-2-ylmethyl)-[2,1,3]-benzoxadiazole-5-carboxamide
N-Methyl-N-pyridin-3-yl-[2,1,3]-benzoxadiazole-5-carboxamide
N-Methyl-N-phenyl-[2,1,3]-benzoxadiazole-5-carboxamide
N-Cyclopropyl-N-tetrahydro-2H-pyran-4-yl-[2,1,3]-benzoxadiazole-5-carboxamide
N-Tetrahydro-2H-pyran-4-yl-N-(2,2,2-trifluoroethyl)-[2,1,3]-benzoxadiazole-5-carboxamide tert-Butyl-4-[([2,1,3]-benzoxadiazol-5-ylcarbonyl)(methyl)amino]piperidine-1-carboxylate
N-Methyl-N-piperidin-4-yl-[2,1,3]-benzoxadiazole-5-carboxamide hydrochloride
N-Methyl-N-(1-methylpiperidin-4-yl)-[2,1,3]-benzoxadiazole-5-carboxamide
N-(1-Acetylpiperidin-4-yl)-N-methyl-[2,1,3]-benzoxadiazole-5-carboxamide
N-(1-Formylpiperidin-4-yl)-N-methyl-[2,1,3]-benzoxadiazole-5-carboxamide
N-Methyl-N-[1-(methylsulfonyl]piperidin-4-yl)-[2,1,3]-benzoxadiazole-5-carboxamide
N-Methyl-N-(tetrahydro-2H-pyran-4-yl)-[2,1,3]-benzothiadiazole-5-carboxamide
N-Methyl-N-(tetrahydro-2H-thiopyran-4-yl)-[2,1,3]-benzoxadiazole-5-carboxamide
N-Methyl-N-(1-oxidotetrahydro-2H-thiopyran-4-yl)-[2,1,3]-benzoxadiazole-5-carboxamide N-Methyl-N-(1,1-dioxidotetrahydro-2H-thiopyran-4-yl)-[2,1,3]-benzoxadiazole-5-carboxamide
N-Methyl-N-tetrahydro-2H-pyran-4-ylquinoxaline-6-carboxamide
N-[4-(Hydroxyimino)cyclohexyl]-N-methyl-[2,1,3]-benzoxadiazole-5-carboxamide
N-[4-(Methoxyimino)cyclohexyl]-N-methyl-[2,1,3]-benzoxadiazole-5-carboxamide
N-(4,4-Difluorocyclohexyl)-N-methyl-[2,1,3]-benzoxadiazole-5-carboxamide
N-(4-fluorocyclohex-3-en-1-yl)-N-methyl-[2,1,3]-benzoxadiazole-5-carboxamide
N-(4-trans-Hydroxycyclohexyl)-[2,1,3]-benzoxadiazole-5-carboxamide
N-(trans-4-Hydroxy-4-methylcyclohexyl)-[2,1,3]-benzoxadiazole-5-carboxamide
N-(cis-4-Hydroxy-4-methylcyclohexyl)-N-methyl-[2,1,3]-benzoxadiazole-5-carboxamide
N-(cis-4-Hydroxy-4-ethylcyclohexyl)-N-methyl-[2,1,3]-benzoxadiazole-5-carboxamide
N-(trans-4-Hydroxy-4-ethylcyclohexyl)-N-methyl-[2,1,3]-benzoxadiazole-5-carboxamide
N-(cis-4-Ethynyl-4-hydroxycyclohexyl)-N-methyl-[2,1,3]-benzoxadiazole-5-carboxamide
N-(cis-4-But-3-en-1-yl-4-hydroxycyclohexyl)-N-methyl-[2,1,3]-benzoxadiazole-5-carboxamide
N-(trans-4-But-3-en-1-yl-4-hydroxycyclohexyl)-N-methyl-[2,1,3]-benzoxadiazole-5-carboxamide
N-(4-trans-Hydroxycyclohexyl)-N-$D_3$-methyl-[2,1,3]-benzoxadiazole-5-carboxamide
N-(trans-4-Methoxycyclohexyl)-N-methyl-[2,1,3]-benzoxadiazole-5-carboxamide
N-(trans-4-Methoxycyclohexyl)-N-methyl-[2,1,3]-benzoxadiazole-5-carbothioamide
N-(4-cis-Hydroxycyclohexyl)-N-methyl-[2,1,3]-benzoxadiazole-5-carboxamide
N-Methyl-N-[trans-4-(2H-tetrazol-2-yl)cyclohexyl]-[2,1,3]-benzoxadiazole-5-carboxamide
N-(trans-4-Azidocyclohexyl)-N-methyl-[2,1,3]-benzoxadiazole-5-carboxamide
N-(trans-4-Aminocyclohexyl)-N-methyl-[2,1,3]-benzoxadiazole-5-carboxamide
N-(cis-3-Hydroxycyclohexyl)-N-methyl-[2,1,3]-benzoxadiazole-5-carboxamide
N-(trans-3-Hydroxycyclohexyl)-N-methyl-[2,1,3]-benzoxadiazole-5-carboxamide
N-Methyl-N-(3-oxocyclohexyl)-[2,1,3]-benzoxadiazole-5-carboxamide
N-Methyl-N-(3,3-difluorocyclohexyl)-[2,1,3]-benzoxadiazole-5-carboxamide
N-(2-Hydroxycyclohexyl)-N-methyl-[2,1,3]-benzoxadiazole-5-carboxamide
N-Methyl-N-(2-oxocyclohexyl)-[2,1,3]-benzoxadiazole-5-carboxamide
N-Methyl-N-(2,2-difluorocyclohexyl)-[2,1,3]-benzoxadiazole-5-carboxamide
N-(2-Hydroxytetrahydro-2H-pyran-4-yl)-[2,1,3]-benzoxadiazole-5-carboxamide
N-(2-oxotetrahydro-2H-pyran-4-yl)-[2,1,3]-benzoxadiazole-5-carboxamide
N-Methyl-N-(2-oxotetrahydro-2H-pyran-4-yl)-[2,1,3]-benzoxadiazole-5-carboxamide
N-(2-Hydroxytetrahydro-2H-pyran-4-yl)-N-methyl-[2,1,3]-benzoxadiazole-5-carboxamide
N—(R)-Tetrahydrofuran-3-yl-[2,1,3]-benzoxadiazole-5-carboxamide
N-Methyl-N—(R)-tetrahydrofuran-3-yl-[2,1,3]-benzoxadiazole-5-carboxamide N-2-(4-Morpholinyl)ethyl-[2,1,3]-benzoxadiazole-5-carboxamide N-Methyl-N-2-(4-morpholinyl)ethyl-[2,1,3]-benzoxadiazole-5-carboxamide hydrochloride N-Methyl-N-tetrahydro-2H-pyran-4-yl-[2,1,3]-benzoxadiazole-5-carbothioamide or N-Methyl-N-tetrahydro-2H-pyran-4-ylmethyl-[2,1,3]-benzoxadiazole-5-carboxamide.

13. A pharmaceutical composition comprising an effective amount of a compound according to any of claims 1-12 in combination with a pharmaceutically acceptable carrier, additive or excipient.

14. The composition according to claim 13 wherein said compound comprises about 0.5% to about 75% by weight of said composition and said carrier, additive or excipient comprises about 25% to about 95.5% of said composition.

15. The compound according to claim 10 which is N-Cyclohexyl-N-methyl-[2,1,3]-benzoxadiazole-5-carboxamide.

16. The compound according to claim 10 which is N-Cyclopentyl-N-methyl-[2,1,3]-benzoxadiazole-5-carboxamide.

17. The compound according to claim 10 which is N-(trans-4-Cyanocyclohexyl)-N-methyl-[2,1,3]-benzoxadiazole-5-carboxamide.

18. The compound according to claim 10 which is N-Methyl-N-tetrahydro-2H-pyran-4-yl-[2,1,3]-benzoxadiazole-5-carboxamide.

19. The compound according to claim 10 which is N-Methyl-N-(4-oxocyclohexyl)-[2,1,3]-benzoxadiazole-5-carboxamide.

20. The compound according to claim 10 which is N-(trans-4-Hydroxy-4-methylcyclohexyl)-N-methyl-[2,1,3]-benzoxadiazole-5-carboxamide.

21. The compound according to claim 10 which is N-(4-trans-Hydroxycyclohexyl)-N-methyl-[2,1,3]-benzoxadiazole-5-carboxamide.

* * * * *